United States Patent
Park et al.

(10) Patent No.: US 9,397,300 B2
(45) Date of Patent: Jul. 19, 2016

(54) COMPOUND AND ORGANIC LIGHT-EMITTING DIODE INCLUDING THE SAME

(71) Applicant: Samsung Display Co., Ltd., Yongin, Gyeonggi-Do (KR)

(72) Inventors: Jun-Ha Park, Yongin (KR); Seok-Hwan Hwang, Yongin (KR); Young-Kook Kim, Yongin (KR); Hye-Jin Jung, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 130 days.

(21) Appl. No.: 13/924,467

(22) Filed: Jun. 21, 2013

(65) Prior Publication Data
US 2014/0225070 A1  Aug. 14, 2014

(30) Foreign Application Priority Data
Feb. 14, 2013 (KR) .................. 10-2013-0016053

(51) Int. Cl.
| | |
|---|---|
| H01L 51/50 | (2006.01) |
| H01L 51/00 | (2006.01) |
| C07C 255/58 | (2006.01) |
| C07C 211/59 | (2006.01) |
| C07D 215/38 | (2006.01) |
| C07D 333/76 | (2006.01) |
| C07D 235/18 | (2006.01) |
| C07C 211/56 | (2006.01) |
| C07C 211/61 | (2006.01) |
| C07D 251/22 | (2006.01) |
| C07D 213/38 | (2006.01) |
| C07D 307/91 | (2006.01) |

(52) U.S. Cl.
CPC ............ *H01L 51/006* (2013.01); *C07C 211/56* (2013.01); *C07C 211/59* (2013.01); *C07C 211/61* (2013.01); *C07C 255/58* (2013.01); *C07D 213/38* (2013.01); *C07D 215/38* (2013.01); *C07D 235/18* (2013.01); *C07D 251/22* (2013.01); *C07D 307/91* (2013.01); *C07D 333/76* (2013.01); *H01L 51/0058* (2013.01); *C07C 2103/18* (2013.01); *C07C 2103/24* (2013.01); *C07C 2103/26* (2013.01); *H01L 51/506* (2013.01); *H01L 51/5012* (2013.01); *H01L 51/5072* (2013.01); *H01L 51/5092* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 5,645,948 A | 7/1997 | Shi et al. | |
| 6,465,115 B2 | 10/2002 | Shi et al. | |
| 6,596,415 B2 | 7/2003 | Shi et al. | |
| 6,878,469 B2 | 4/2005 | Yoon et al. | |
| 7,485,733 B2 | 2/2009 | Kim et al. | |
| 7,651,786 B2 | 1/2010 | Matsuura et al. | |
| 7,732,063 B2 | 6/2010 | Matsuura et al. | |
| 8,222,634 B2 | 7/2012 | Lee et al. | |
| 2005/0064233 A1 | 3/2005 | Matsuura et al. | |
| 2006/0124924 A1* | 6/2006 | Suh et al. ......................... | 257/40 |
| 2007/0018569 A1* | 1/2007 | Kawamura et al. ........... | 313/504 |
| 2008/0258615 A1* | 10/2008 | Begley et al. ................. | 313/504 |
| 2009/0267497 A1* | 10/2009 | Kawakami et al. ........... | 313/504 |
| 2011/0024725 A1* | 2/2011 | Lee ..................... | C07D 209/86 257/40 |
| 2011/0114934 A1 | 5/2011 | Kim et al. | |
| 2011/0240979 A1* | 10/2011 | Kim et al. ....................... | 257/40 |

FOREIGN PATENT DOCUMENTS

| | | |
|---|---|---|
| JP | 10-017860 A | 1/1998 |
| JP | 11-087067 A | 3/1999 |
| KR | 10-2004-0028954 A | 4/2004 |
| KR | 10-0691543 B1 | 2/2007 |
| KR | 10-2008-0101793 A | 11/2008 |
| KR | 10-2009-0111355 A | 10/2009 |
| KR | 10-2009-0111356 A | 10/2009 |

(Continued)

OTHER PUBLICATIONS

Adachi et al., "Confinement of charge carriers and molecular excitons within 5-nm-thick emitter layer in organic electroluminescent devices with a double heterostructure," *Appl. Phys. Lett.* 57, No. 6, 531-533 (Aug. 6, 1990).

(Continued)

*Primary Examiner* — Gregory Clark
(74) *Attorney, Agent, or Firm* — Knobbe, Martens, Olson & Bear LLP

(57) ABSTRACT

Provided is an organic light-emitting diode including a compound of Formula 1 below:

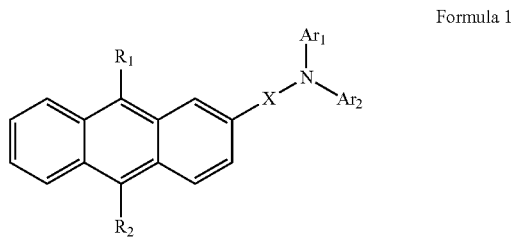

Formula 1

A detailed description of a substituent in Formula 1 above is defined as described in the detailed description.

20 Claims, 1 Drawing Sheet

(56) References Cited

FOREIGN PATENT DOCUMENTS

| KR | 10-2010-0006979 A | 1/2010 |
|---|---|---|
| KR | 10-2011-0047278 A | 5/2011 |

OTHER PUBLICATIONS

Johansson et al., Solid-State Amplified Spontaneous Emission in Some Spiro-Type Molecules: A New Concept for the Design of Solid-State Lasing Molecules, *Adv. Mater.* 10, No. 14, 1136-1141 (1998).

Sakamoto et al., "Synthesis, Characterization, and Electron-Transport Property of Perfluorinated Phenylene Dendrimers," *J. Am. Chem. Soc.* 122, No. 8, 1832-1833 (2000).

Tang et al., "Organic electroluminescent diodes," *Appl. Phys. Lett.* 51, No. 12, 913-915 (Sep. 21, 1987).

Tao et al., "Sharp green electroluminescence from 1*H*-pyrazolo[3,4-*b*]quinoline-based light-emitting diodes," *Appl. Phys. Lett.* 77, No. 11, 1575-1577 (2000).

Yamaguchi et al., "Diphenylamino-Substituted 2,5-Diarylsiloles for Single-Layer Organic Electroluminescent Devices," *Chemistry Letters 2001, The Chemical Society of Japan*, 98-99 (2001).

\* cited by examiner

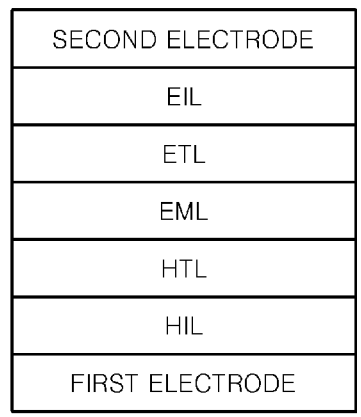

COMPOUND AND ORGANIC LIGHT-EMITTING DIODE INCLUDING THE SAME

CROSS-REFERENCE TO RELATED APPLICATIONS

This application claims the benefit of Korean Patent Application No. 10-2013-0016053, filed on Feb. 14, 2013, in the Korean Intellectual Property Office, the disclosure of which is incorporated herein in its entirety by reference.

BACKGROUND

1. Field

The present embodiments relate to a compound and an organic light-emitting diode including the same.

2. Description of the Related Technology

Organic light-emitting diodes (OLEDs), which are self-emitting diodes, have advantages such as wide viewing angles, excellent contrast, quick response, high brightness, and excellent driving voltage, and can provide multicolored images.

A typical diode has a structure including a substrate, an anode formed on the substrate, and a hole transport layer (HTL), an emission layer (EML), an electron transport layer (ETL), and a cathode which are sequentially stacked on the substrate. The HTL, the EML, and the ETL are organic thin films comprising organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons (carriers) recombine in the EML to generate excitons. When the excitons drop from an excited state to a ground state, light is emitted.

A conventional OLED using an organic monomolecular material as an HTL has problems of a short luminescence lifetime, low preservative durability, and low reliability. These problems arise due to physical or chemical changes of organic materials, photochemical or electrochemical changes of organic materials, oxidation of anodes, exfoliation, or a lack of durability.

SUMMARY OF CERTAIN INVENTIVE ASPECTS

The present embodiments provide a novel compound and an organic light-emitting diode (OLED) including the same. The compound has excellent electrical properties, high charge-transporting abilities, and high light-emitting abilities. The compound, which is a material having a high glass transition temperature and is capable of preventing crystallization, can be effectively used as an electron-transporting material that is suitable for a fluorescent and a phosphorescent diode of emitting all colors such as red, green, blue, and white. The compound can be also used as a light-emitting material for producing green, blue, and white. Therefore, the compound may have a better luminance efficiency and OLED lifetime compared to a conventional host material, and an OLED including the compound and having high efficiency, low voltage, high brightness, and long lifetime characteristics is provided.

According to an aspect of the present embodiments, there is provided a compound represented by Formula 1 below:

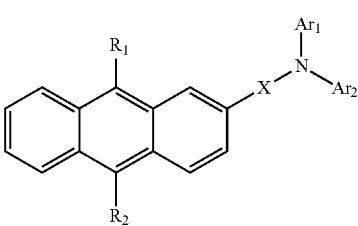

Formula 1 wherein, in Formula 1, $R_1$ and $R_2$ may be each independently a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group;

$Ar_1$ and $Ar_2$ may be each independently a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; and X may be a substituted or unsubstituted $C_6$-$C_{60}$ aryl group, a substituted or unsubstituted $C_2$-$C_{60}$ heteroaryl group, a substituted or unsubstituted $C_6$-$C_{60}$ condensed polycyclic group, or a divalent linking group with at least two of the aryl group, the heteroaryl group, and the condensed polycyclic group linked together.

According to another aspect of the present embodiments, there is provided an OLED including a first electrode; a second electrode; and an organic layer that is disposed between the first electrode and the second electrode and includes the compound of Formula 1 described above.

According to another aspect of the present embodiments, there is provided a flat panel display device including the above-described OLED, wherein the first electrode of the OLED is electrically connected to a source electrode or a drain electrode of a thin-film transistor (TFT).

BRIEF DESCRIPTION OF THE DRAWINGS

The above and other features and advantages of the present embodiments will become more apparent by describing in detail example embodiments thereof with reference to the attached drawings in which:

FIG. 1 is a schematic view of a structure of an organic light-emitting diode (OLED) according to an embodiment.

DETAILED DESCRIPTION OF CERTAIN INVENTIVE EMBODIMENTS

As used herein, the term "and/or" includes any and all combinations of one or more of the associated listed items. Expressions such as "at least one of," when preceding a list of elements, modify the entire list of elements and do not modify the individual elements of the list.

According to an aspect of the present embodiments, there is provided a compound represented by Formula 1 below:

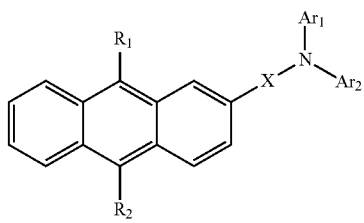

Formula 1 wherein, in Formula 1, $R_1$ and $R_2$ may be each independently a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group;

$Ar_1$ and $Ar_2$ may be each independently a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group; and X may be a substituted or unsubstituted $C_6$-$C_{60}$ aryl group, a substituted or unsubstituted $C_2$-$C_{60}$ heteroaryl group, a substituted or unsubstituted $C_6$-$C_{60}$ condensed polycyclic group, or a divalent linking group with at least two of the aryl group, the heteroaryl group, and the condensed polycyclic group linked together.

In some embodiments, the compound of Formula 1 may act as a light-emitting material and/or an electron-transporting material or an electron-injecting material for an organic light-emitting diode (OLED). In particular, a conventional compound used as an electron-transporting material is mostly a metal complex having a heterocyclic aromatic compound as a ligand, or is an aromatic compound having the heterocyclic aromatic compound as a substituent, wherein the heterocyclic aromatic compound is a relatively electron deficient compound.

However, a compound having both a naphtyl anthracene group and an arylamine group within a molecule, such as, the compound of Formula 1 according to the present embodiments, may have a rich structure with high electron mobility due to the introduction of an anthracene compound thereto. Also, since the compound of Formula 1 above has both a naphtyl anthracene group and an arylamine compound within a molecule, it may have a hole-transporting capability. When a molecule having the described-above structure is used in an electron transport layer, an OLED may have a good balance between electrons and holes within the molecules and a high durability in regard to the electrons and the holes. Therefore, in regard to electroluminescence, the compound of Formula 1 above increases its thermal resistance and high-temperature environment resistant against Joule's heat that is generated in an organic layer, between organic layers, or between an organic layer and a metal electrode. An OLED manufactured using the compound of Formula 1 above as an electron-transporting material has a large effect on increasing advantages such as high durability during storage or operation, and improvement in efficiency.

A substituent in the compound of Formula 1 will now be described in detail.

According to an embodiment, $R_1$ and $R_2$ in Formula 1 may be identical to each other.

According to another embodiment, $R_1$ and $R_2$ in Formula 1 may be each independently one of the following compounds represented by Formulas 2a to 2f below:

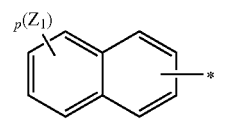

2a

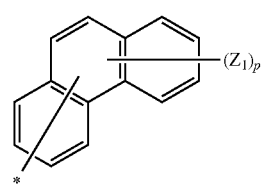

2b

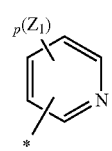

2c

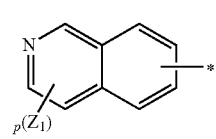

2d

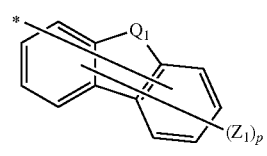

2e

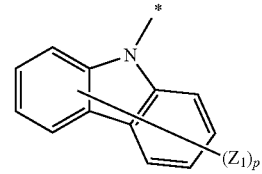

2f wherein, in Formulas 2a to 2e, $Q_1$ may be a linking group represented by —C($R_{30}$)($R_{31}$)— or —N($R_{32}$)—;

$Z_1$, $R_{30}$, $R_{31}$, and $R_{32}$ may be each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano atom, a nitro group, a hydroxyl group, or a carboxyl group;

p may be an integer from 1 to 9; and

* may be a binding site.

In some other embodiments, $Ar_1$ and $Ar_2$ in Formula 1 may be each independently a linking group with at least one of the following groups represented by Formulas 3a to 3e below:

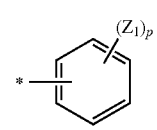

3a

-continued

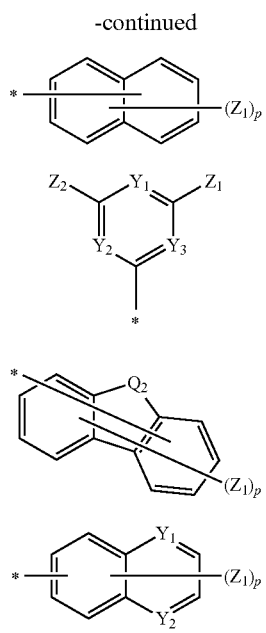

3b

3c

3d

3e wherein, in Formulas 3a to 3e, $Y_1$, $Y_2$, and $Y_3$ may be each independently a linking group represented by —N= or —C($R_{21}$)=;

$Q_2$ may be a linking group represented by —C($R_{30}$)($R_{31}$)—, —N($R_{32}$)—, —S—, or —O—;

$Z_1$, $Z_2$, $R_{21}$, $R_{30}$, $R_{31}$, and $R_{32}$ may be each independently a hydrogen group, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group; and

* may be a binding site.

$Z_1$ and $Z_2$ may be, for example, a cyano group or a halogen atom.

In some other embodiments, X in Formula 1 may be one of the following compounds represented by Formulas 4a to 4d below:

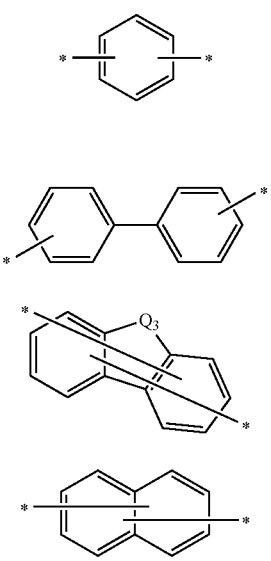

4a

4b

4c

4d wherein, in Formulas 4a to 4d, $Q_3$ may be a linking group represented by —C($R_{30}$)($R_{31}$)— or —S—;

$R_{30}$ and $R_{31}$ may be each independently a hydrogen group, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group; and

* may be a binding site.

Hereinafter, the definition of representative substituents used herein will now be described in detail. (In this regard, numbers of carbons limiting a substituent are non-limited, and thus the substituent characteristics are not limited).

The unsubstituted $C_1$-$C_{60}$ alkyl group used herein may be linear or branched. Non-limiting examples of the unsubstituted $C_1$-$C_{60}$ alkyl group are a methyl group, an ethyl group, a propyl group, an iso-butyl group, a sec-butyl group, a pentyl group, an iso-amyl group, a hexyl group, a heptyl group, an octyl group, a nonanyl group, and a dodecyl group. At least one hydrogen atom of the unsubstituted $C_1$-$C_{60}$ alkyl group may be substituted with a deuterium atom, a halogen atom, a hydroxyl group, a nitro group, a cyano atom, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsubstituted alkenyl group having at least one carbon-carbon double bond in the center or at a terminal thereof. Examples of the unsubstituted $C_2$-$C_{60}$ alkenyl group are an ethenyl group, a propenyl group, a butenyl group, and the like. At least one hydrogen atom of the unsubstituted alkenyl group may be substituted with the same substituent as used in the substituted alkyl group described above.

The unsubstituted $C_2$-$C_{60}$ alkynyl group indicates an unsubstituted alkynyl group having at least one carbon-carbon triple bond in the center or at a terminal of thereof. Examples of the unsubstituted $C_2$-$C_{60}$ alkynyl group are acetylene, propylene, phenylacetylene, naphthylacetylene, isopropylacetylene, t-butylacetylene, diphenylacetylene, and the like. At least one hydrogen atom of the unsubstituted $C_2$-$C_{60}$ alkynyl group may be substituted with the same substituent as used in the substituted alkyl group.

The unsubstituted $C_3$-$C_{60}$ cycloalkyl group indicates an alkyl group in the form of $C_{30}$-$C_{60}$ rings, and at least one hydrogen atom of the $C_{30}$-$C_{60}$ cycloalkyl group may be substituted with the same substituent with the same substituent as used in the $C_1$-$C_{60}$ alkyl group.

The unsubstituted $C_1$-$C_{60}$ alkoxy group has a structure of —OA (wherein, A is an unsubstituted $C_1$-$C_{60}$ alkyl group described above). Non-limiting examples of the unsubstituted $C_1$-$C_{60}$ alkoxy group are a methoxy group, an ethoxy group, a propoxy group, an isopropyloxy group, a butoxy group, a pentoxy group, and the like. At least one hydrogen atom of the unsubstituted alkoxy group may be substituted with the same substituent as used in the substituted alkyl group.

The unsubstituted $C_5$-$C_{60}$ aryl group indicates a carbocyclic aromatic system including at least one ring. When the unsubstituted $C_5$-$C_{60}$ aryl group has two or more of rings, the rings may be fused or linked to each other by a single bond. The term 'aryl' refers to an aromatic system such as phenyl, napthyl, and anthracenyl. Also, at least one hydrogen atom of the aryl group may be substituted with the same substituent as used in the $C_1$-$C_{60}$ alkyl group.

Examples of the substituted or unsubstituted $C_5$-$C_{60}$ aryl group are a phenyl group, a $C_1$-$C_{10}$ alkylphenyl group (e.g., an ethylphenyl group), a halophenyl group (e.g., an o-, m-, and p-fluorophenyl group and a dichlorophenyl group), a cyanophenyl group, a dicyanophenyl, a trifluoromethoxyphenyl group, a biphenyl group, a halobiphenyl group, a cyanobiphenyl group, a $C_1$-$C_{10}$ alkylbiphenyl group, a $C_1$-$C_{10}$ alkoxybiphenyl group, an o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphtyl group, a halonaphtyl group (e.g., a fluoronaphtyl group), a $C_1$-$C_{10}$ alkylnaphtyl group (e.g., a methylnaphtyl group), a $C_1$-$C_{10}$ alkoxynaphtyl group (e.g., a methoxynaphtyl group), a cyanonaphtyl group, an anthracenyl group, an azulenyl group, a heptalenyl group, an acenaphtylenyl group, a phenalenyl group, a fluorenyl group, an anthraquinolyl group, a methylanthryl group, a phenanthryl group, a triphenylene group, a pyrenyl group, a chrycenyl group, an ethylchrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphtylenyl group, a heptaphenyl group, a heptacenyl group, a pyranthrenyl group, an ovalenyl group, and the like.

The unsubstituted $C_3$-$C_{60}$ heteroaryl group used herein may include one, two, or three hetero atoms selected from N, O, P, or S. When the unsubstituted $C_3$-$C_{60}$ heteroaryl group has two or more of rings, the rings are fused or linked to each other by a single bond. Examples of the unsubstituted $C_4$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indolyl group, a quinolyl group, an isoquinolyl group, and a dibenzothiophene group, and the like. In addition, at least one hydrogen atom of the heteroaryl group may be substituted with the same substituent as used in the unsubstituted $C_1$-$C_{60}$ alkyl group.

The unsubstituted $C_5$-$C_{60}$ aryloxy group is a group represented by —$OA_1$, wherein $A_1$ is a $C_5$-$C_{60}$ aryl group. Examples of the aryloxy group are a phenoxy group, and the like. At least one hydrogen atom of the aryloxy group may be substituted with the same substituent as used in the unsubstituted $C_1$-$C_{60}$ alkyl group.

The unsubstituted $C_5$-$C_{60}$ arylthio group is a group represented by —$SA_1$, wherein $A_1$ is a $C_5$-$C_{60}$ aryl group. Examples of the arylthio group are a benzenethio group, a naphthylthio group, and the like. At least one hydrogen atom of the arylthio group may be substituted with the same substituent as used in the unsubstituted $C_1$-$C_{60}$ alkyl group.

The unsubstituted $C_6$-$C_{60}$ condensed polycyclic group used herein refers to a substituent including at least two rings wherein at least one aromatic ring and at least one non-aromatic ring are fused to each other, or a substituent having an unsaturated group within a ring but being unable to form a conjugated structure. Therefore, the unsubstituted $C_6$-$C_{60}$ condensed polycyclic group is distinct from the aryl or the heteroaryl groups in terms of being non-aromatic.

Examples of the compound of Formula 1 according to the present embodiments are the following compounds represented by Formulas 1 to 175 below, but are not limited thereto:

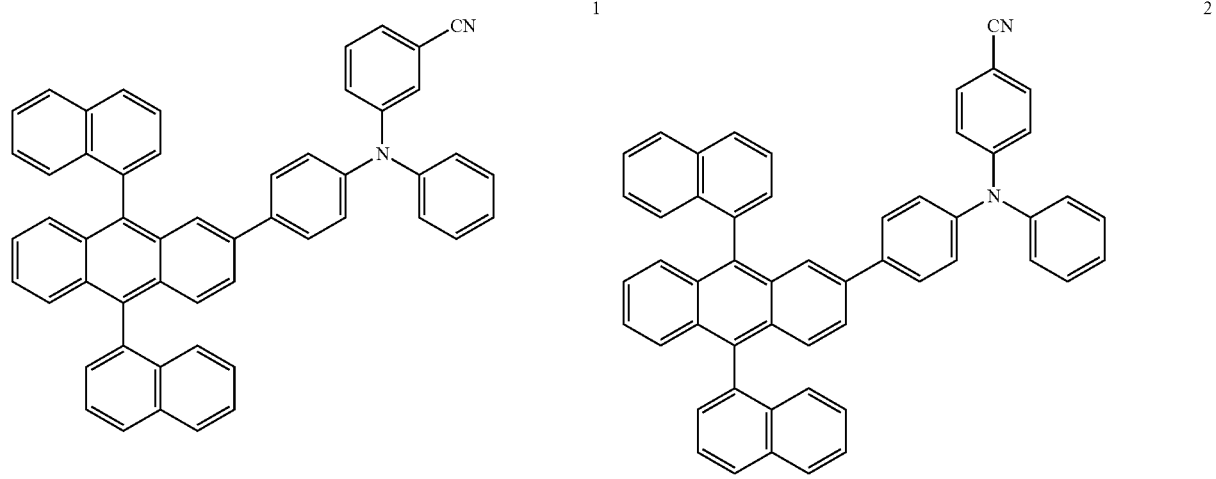

-continued
3
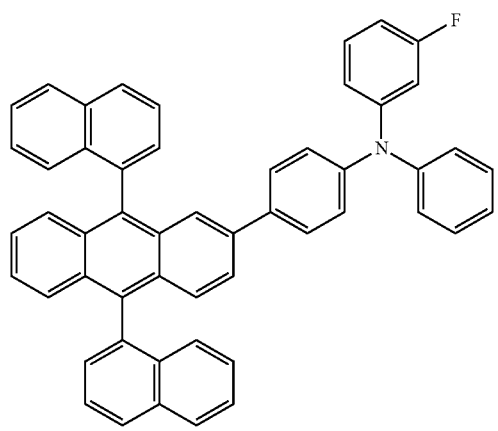
4
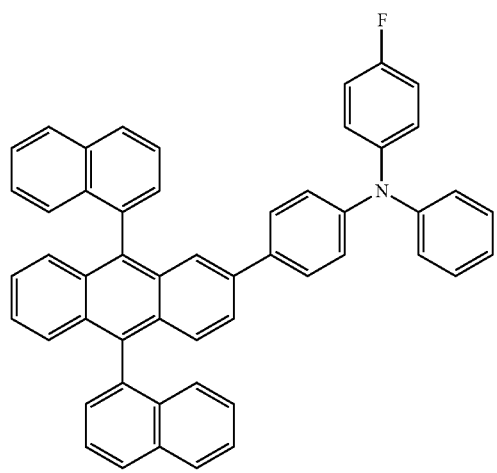
5
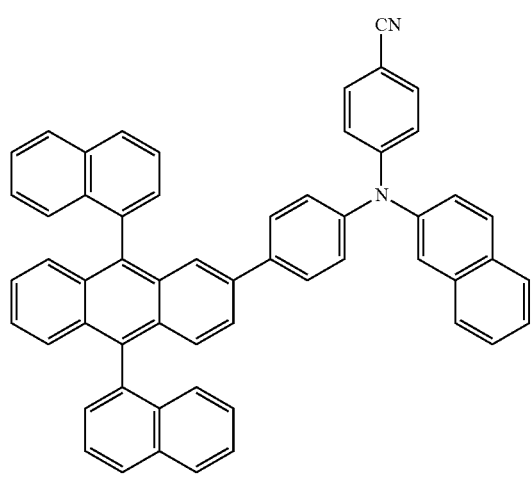
6
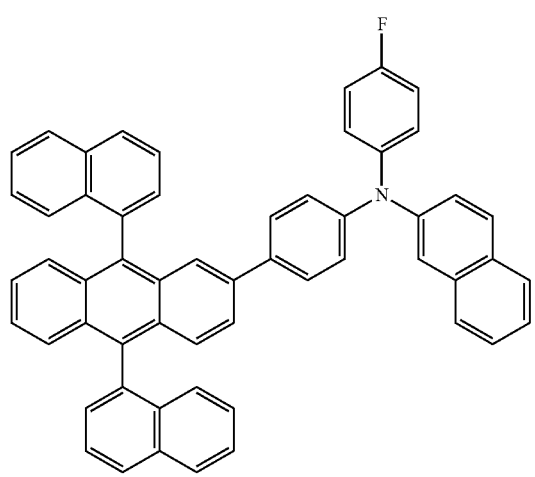
7
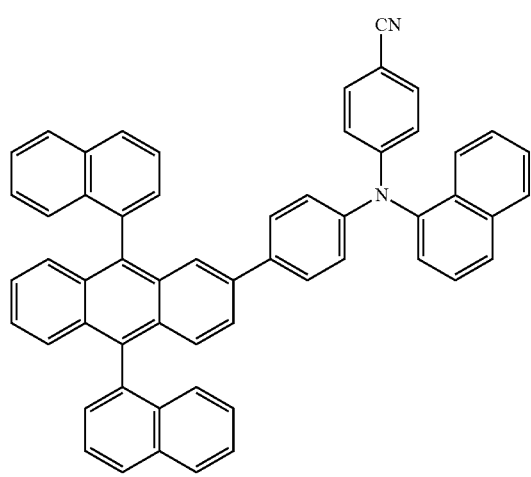
8
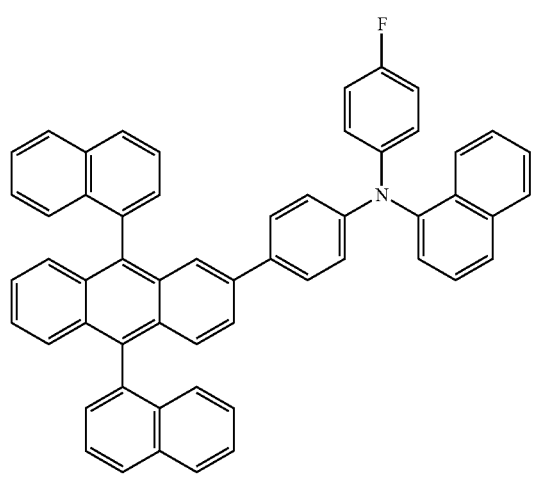

-continued
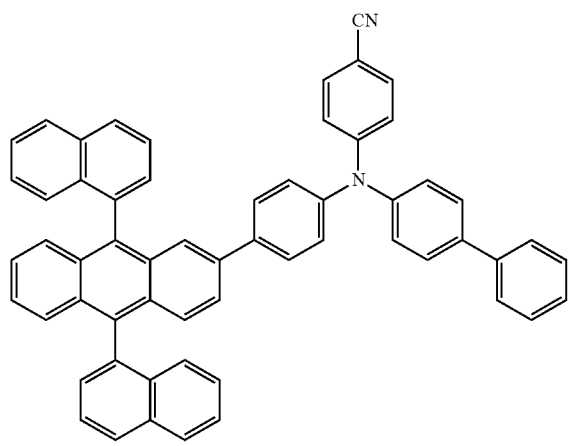
9
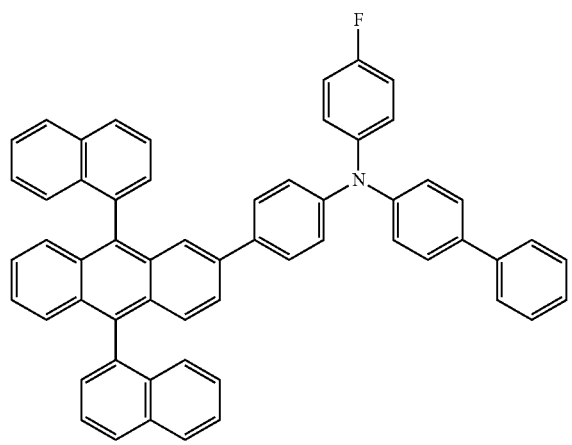
10
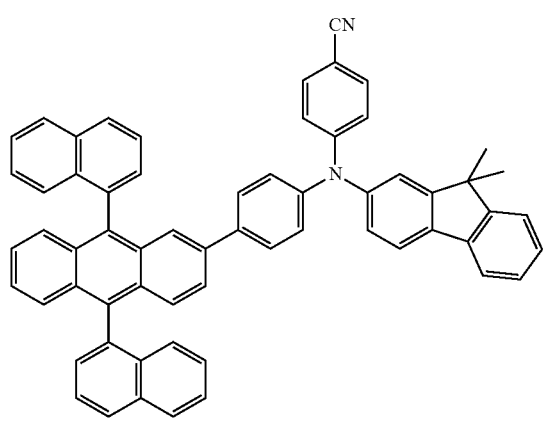
11
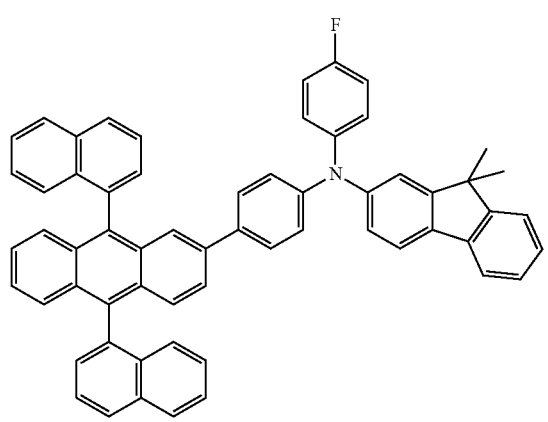
12
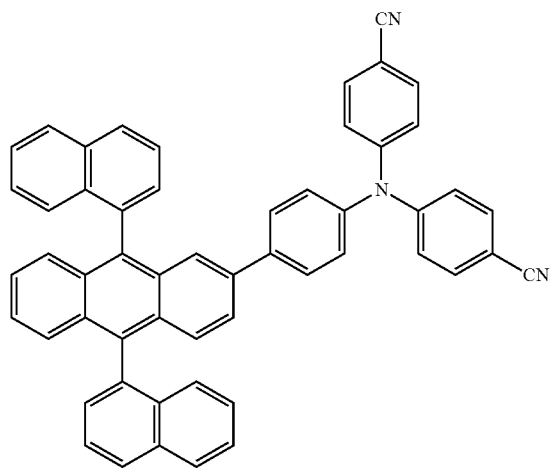
13
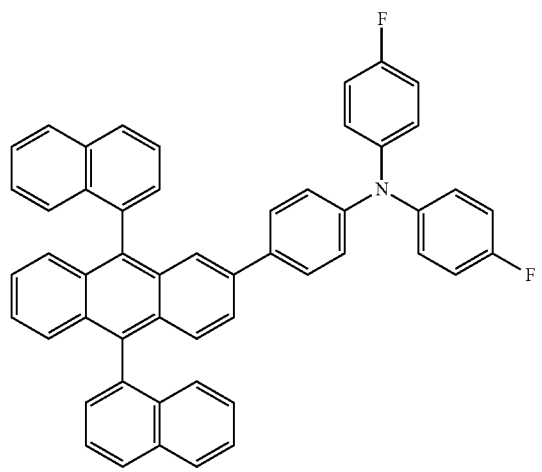
14

-continued
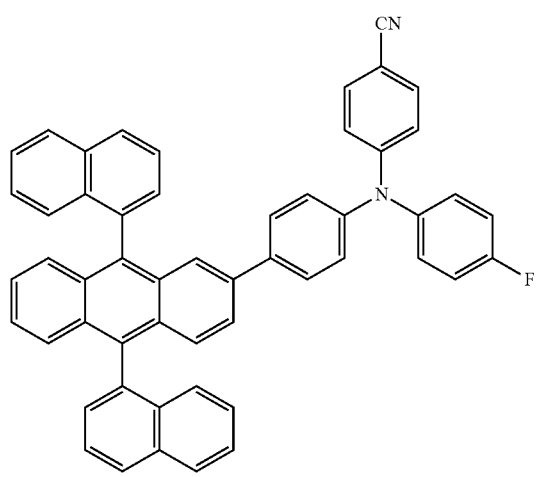
15
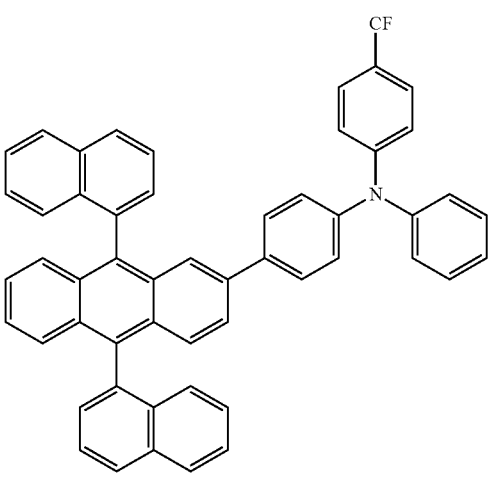
16
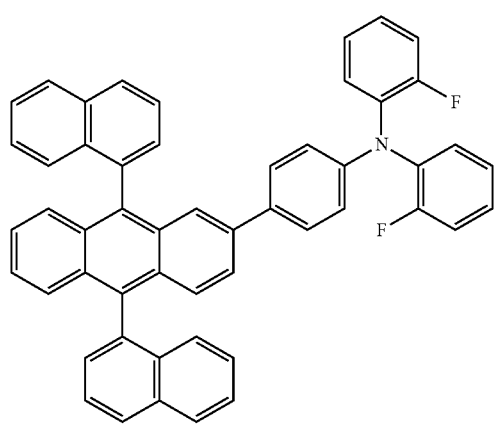
17
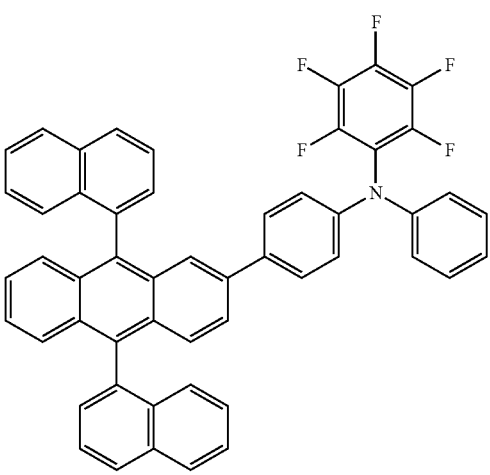
18
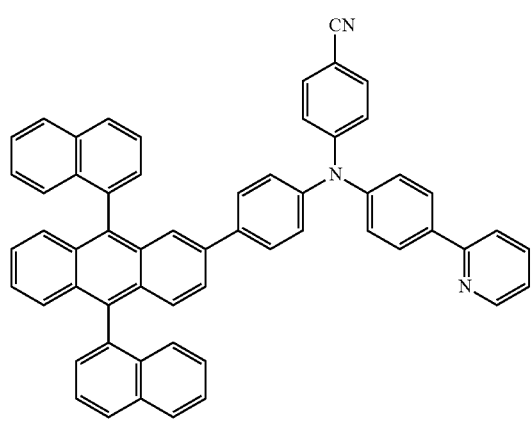
19
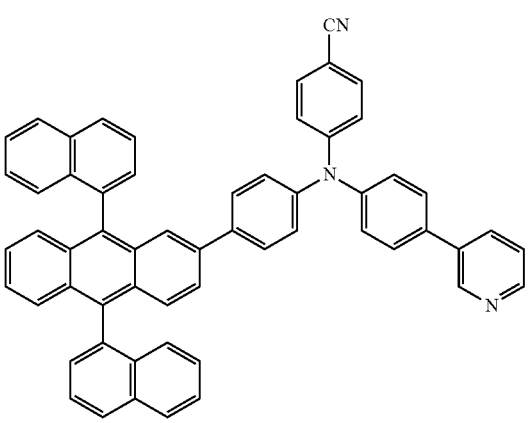
20

-continued
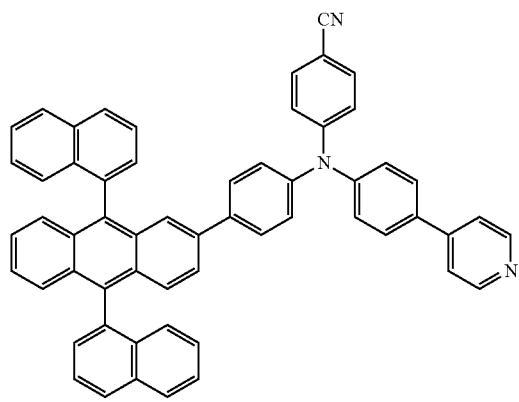
21
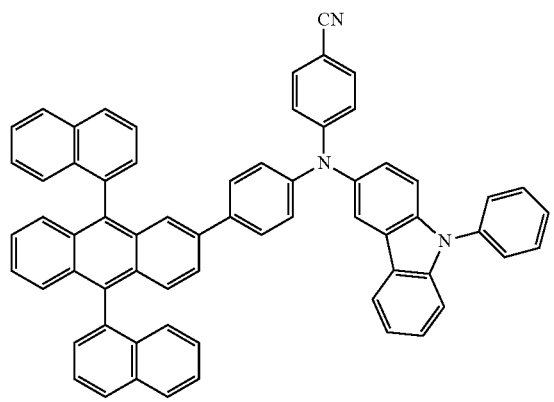
22
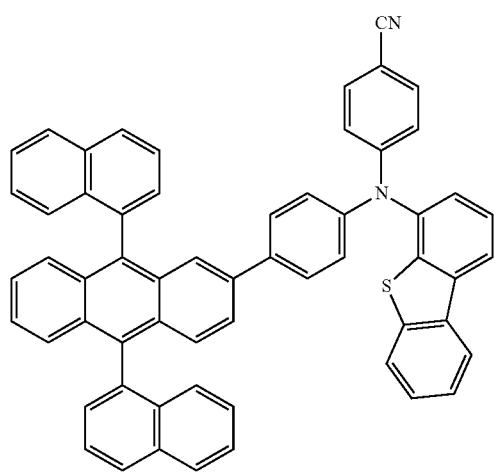
23
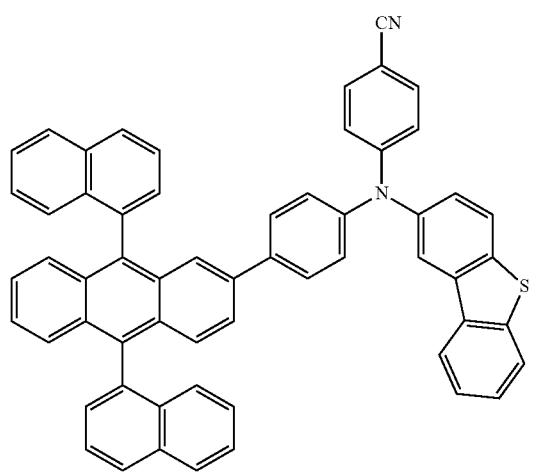
24
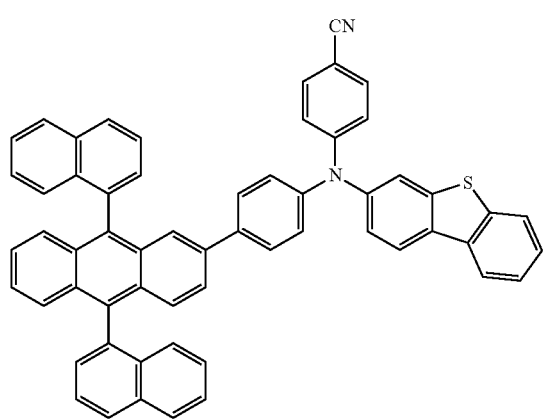
25
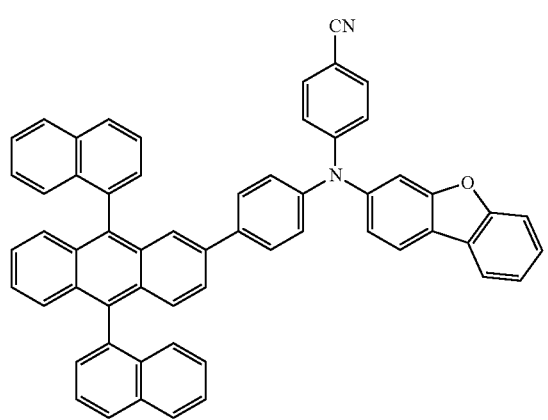
26

-continued
27
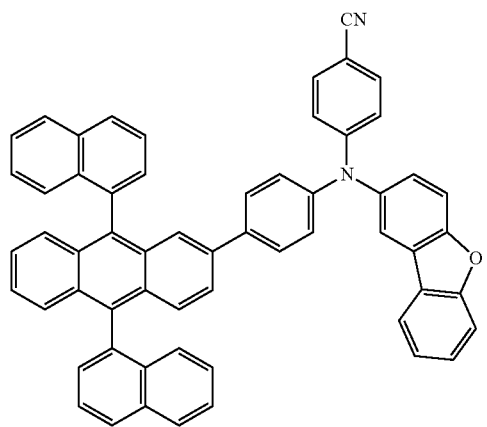
28
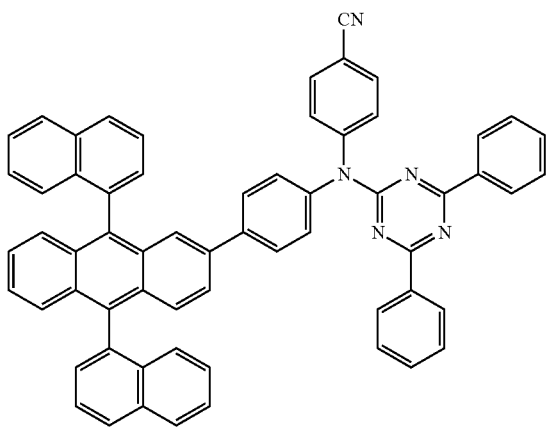
29
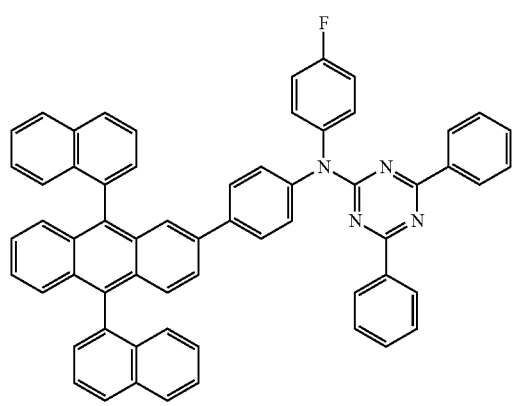
30
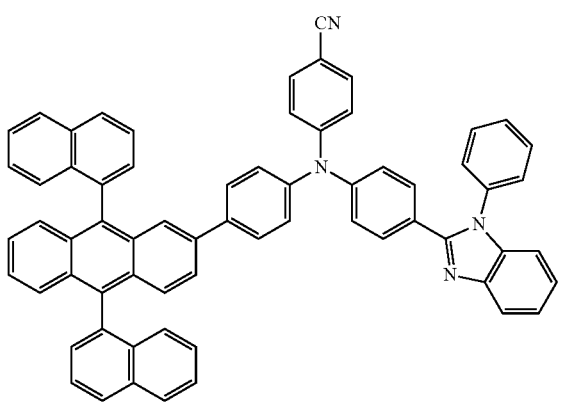
31
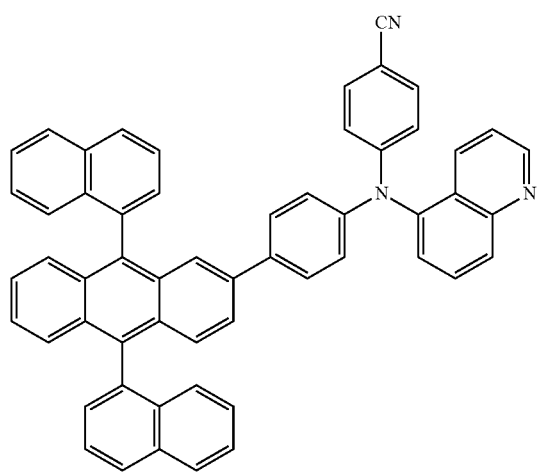
32
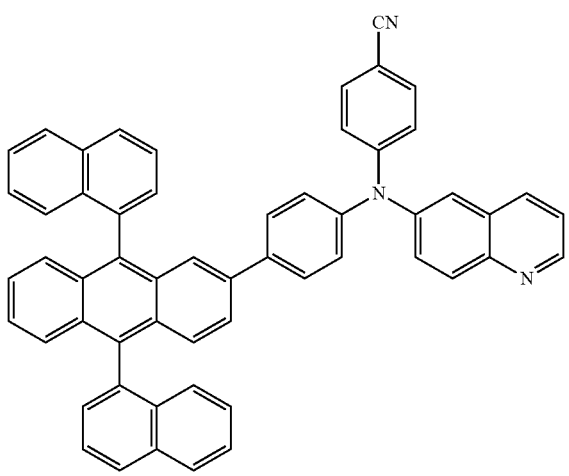

-continued
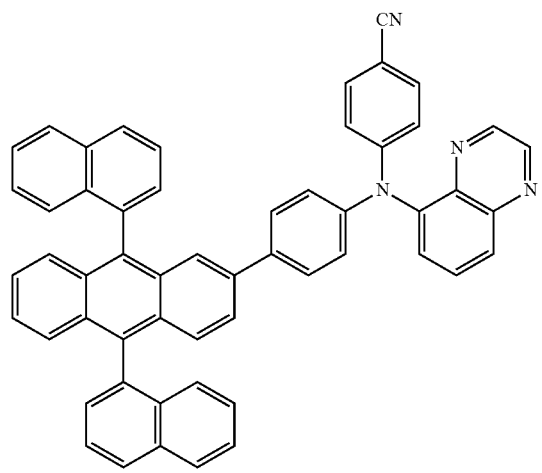
33
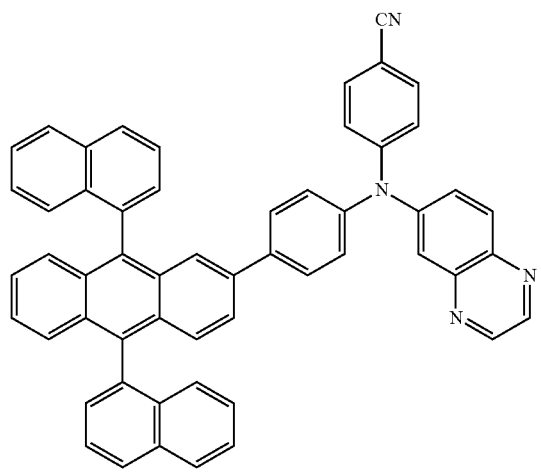
34
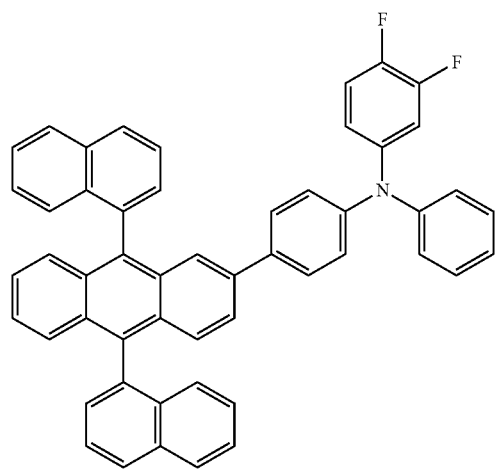
35
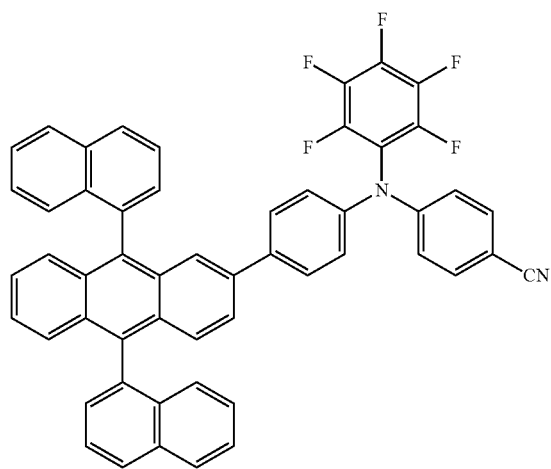
36
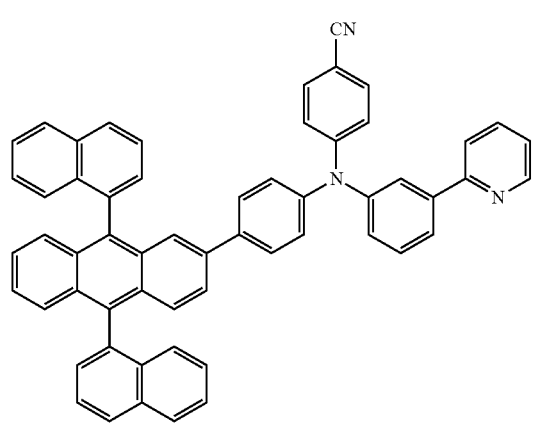
37
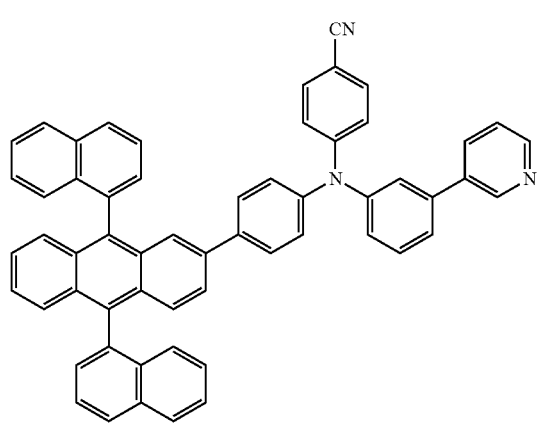
38

-continued
39
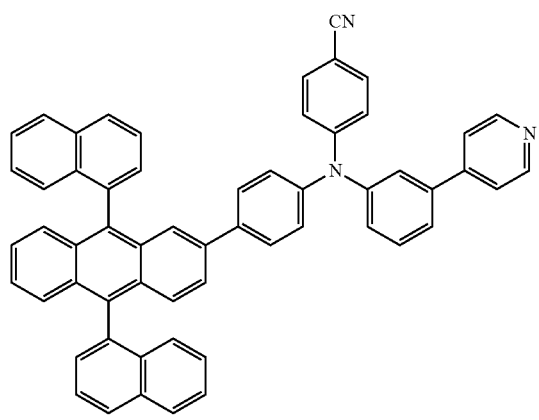
40
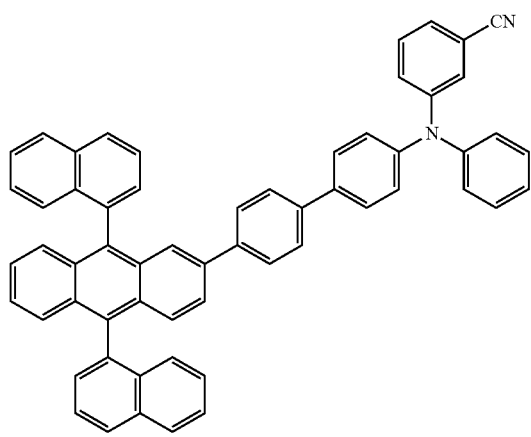
41
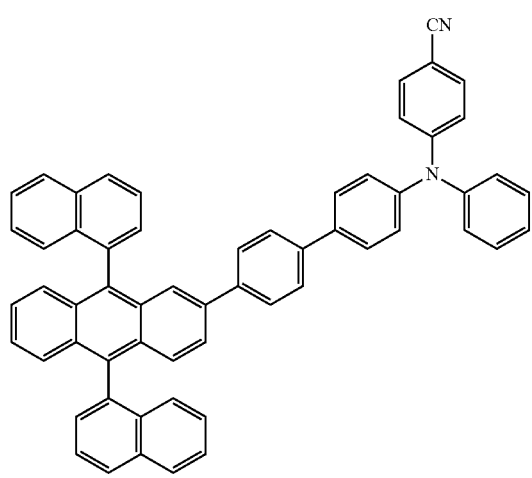
42
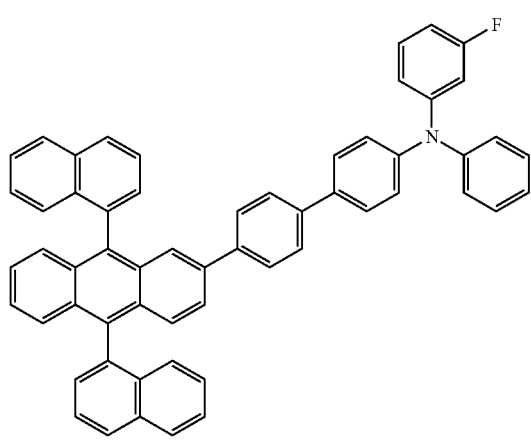
43
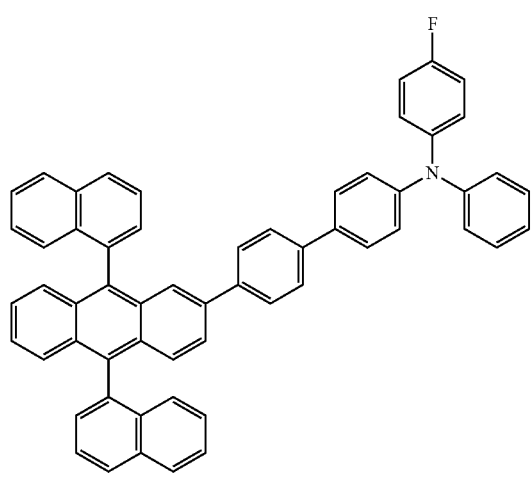
44
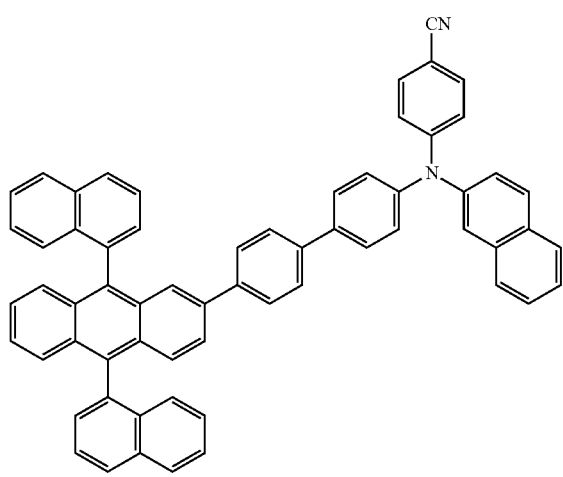

-continued
45
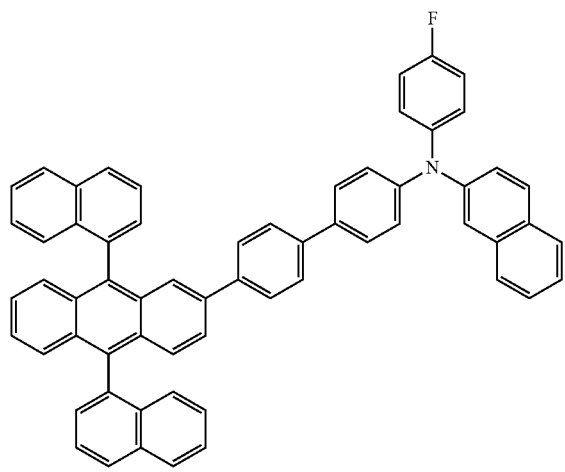
46
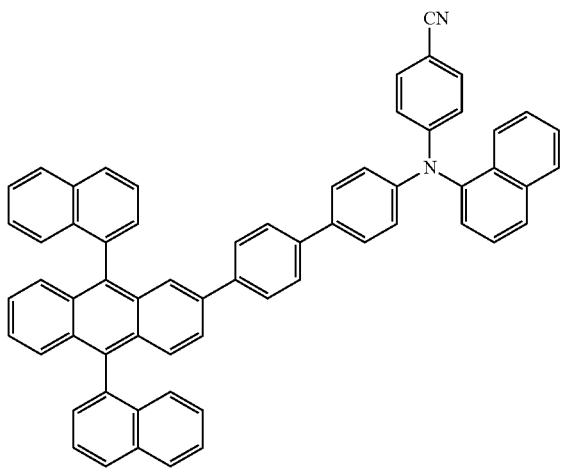
47
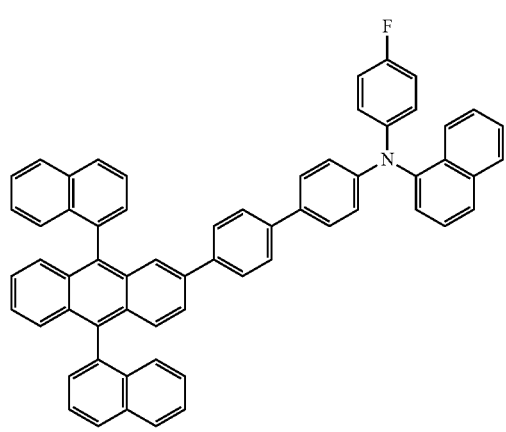
48
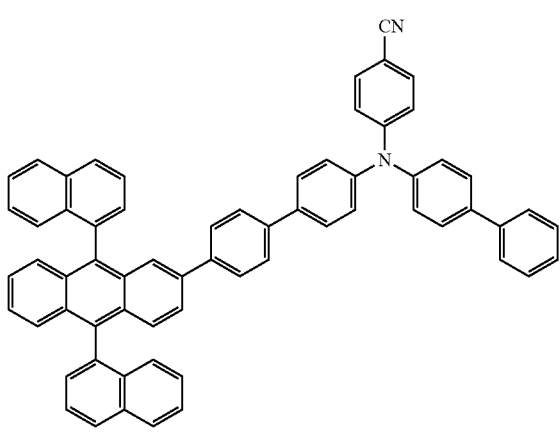
49
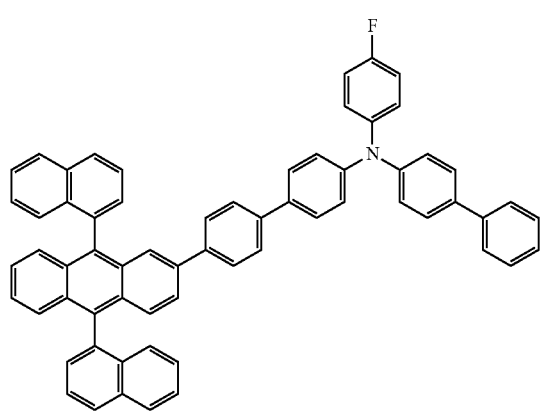
50
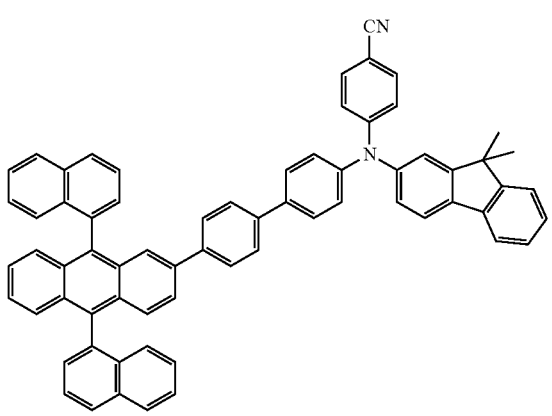

-continued
51
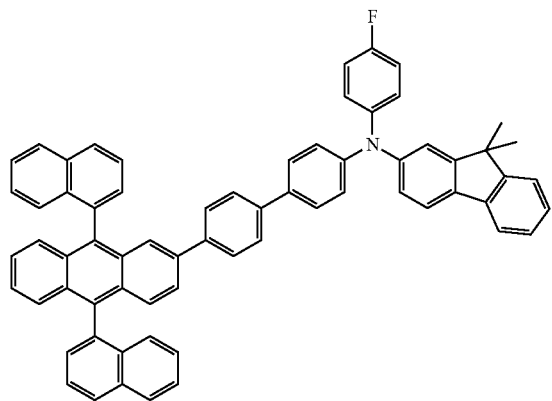
52
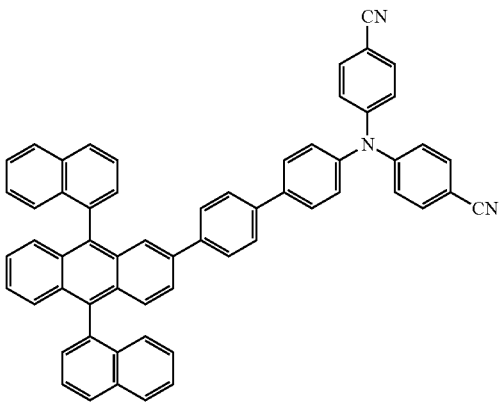
53
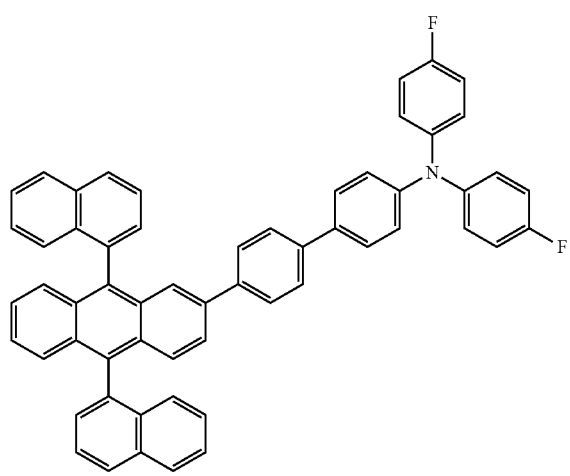
54
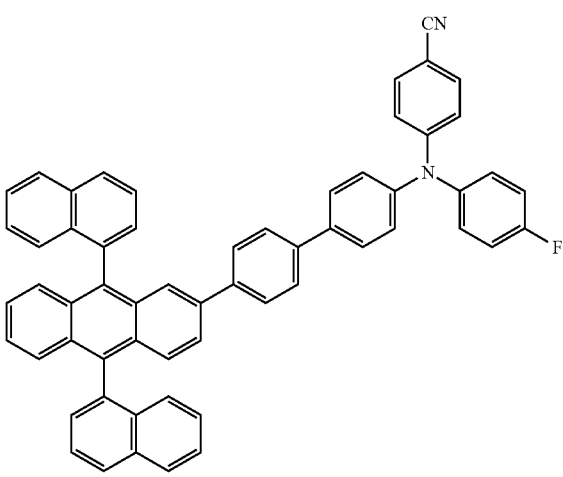
55
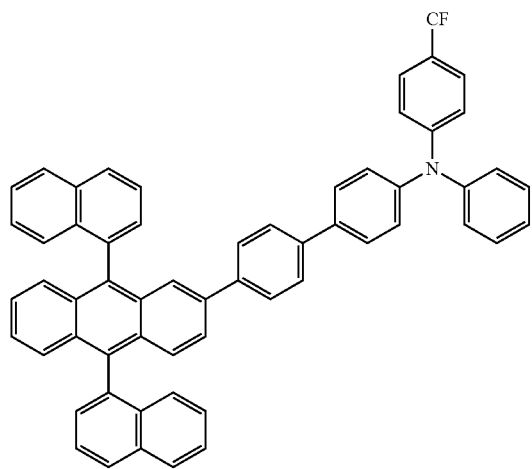
56
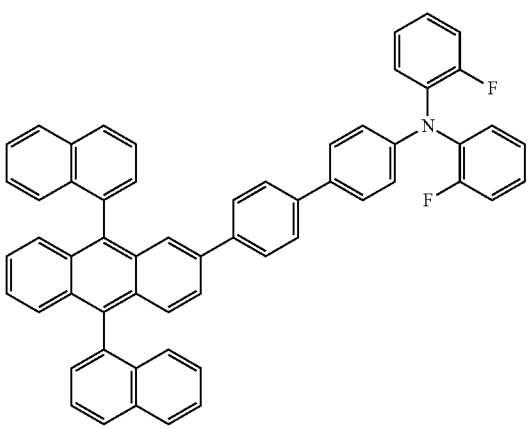

-continued
57
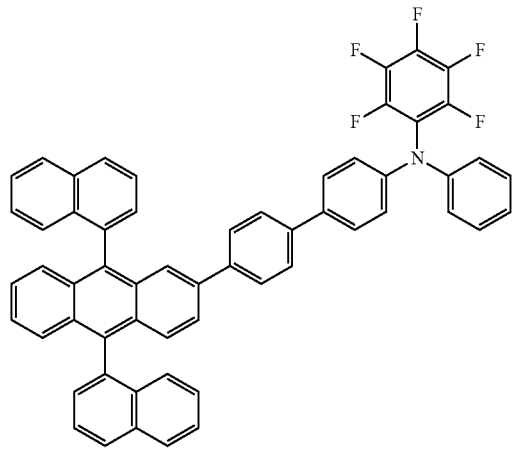
58
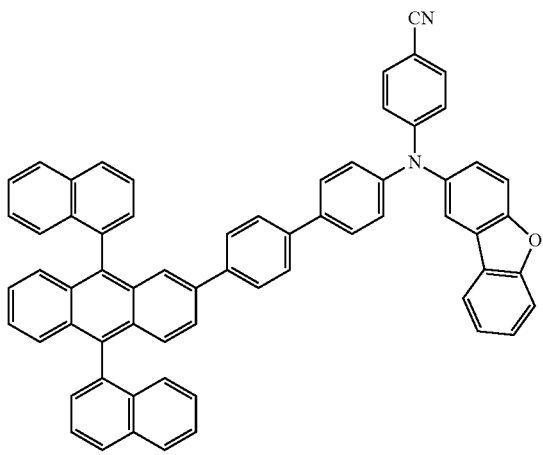
59
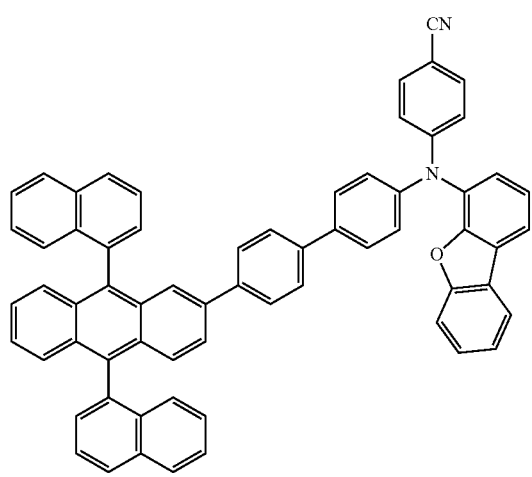
60
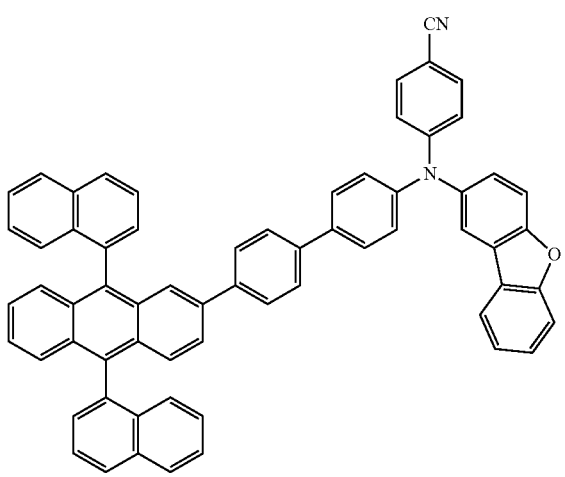
61
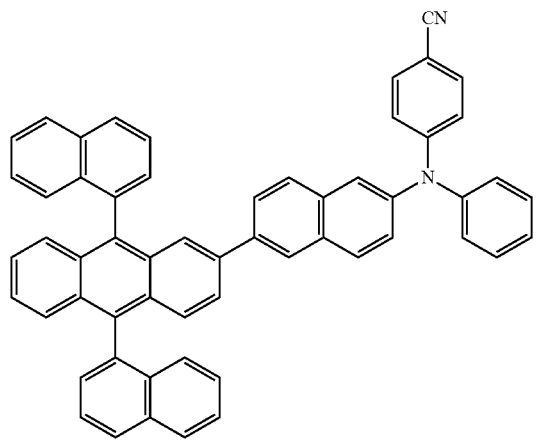
62
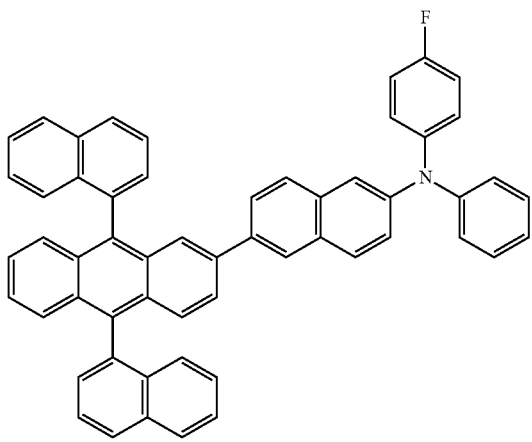

-continued
63
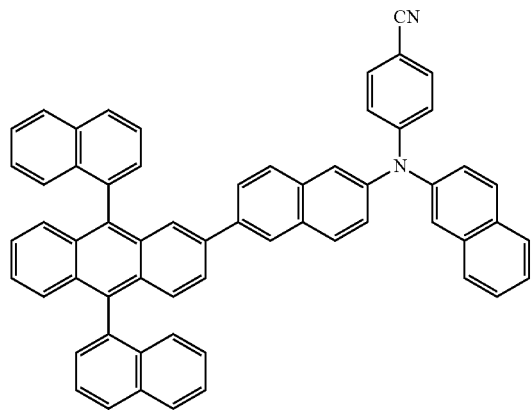
64
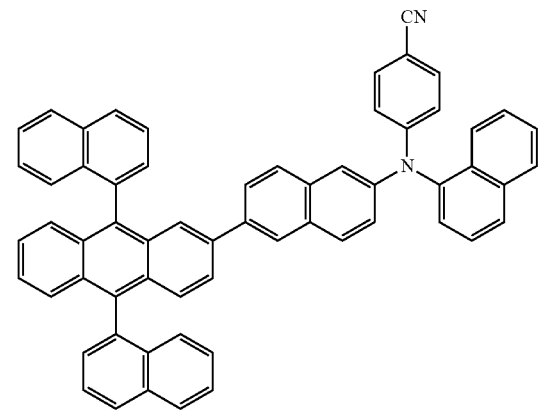
65
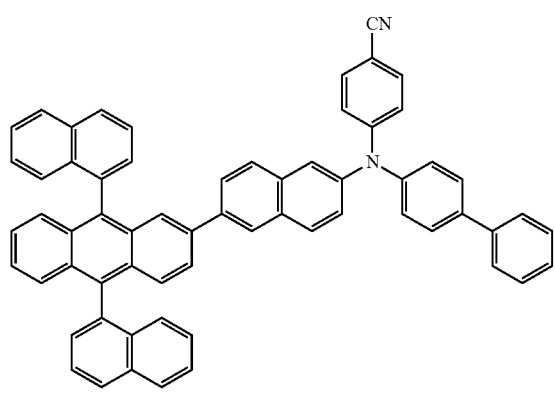
66
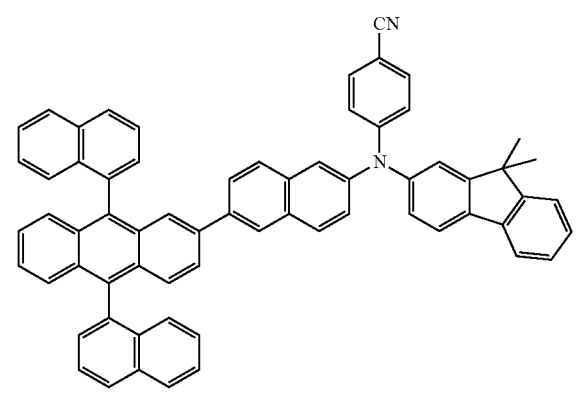
67
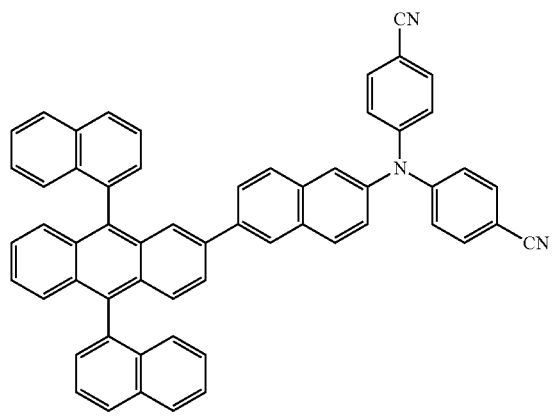
68
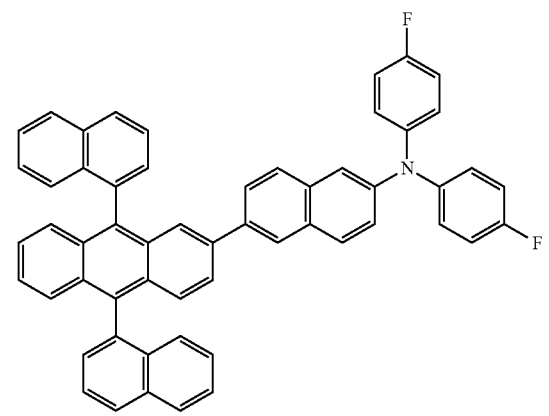
69
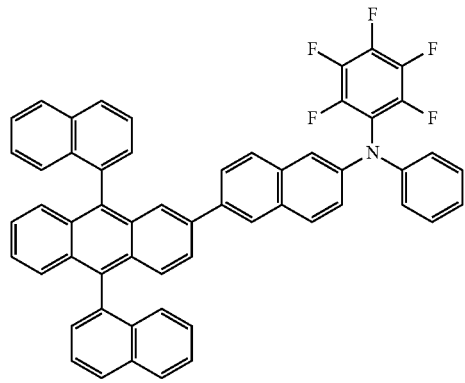
70
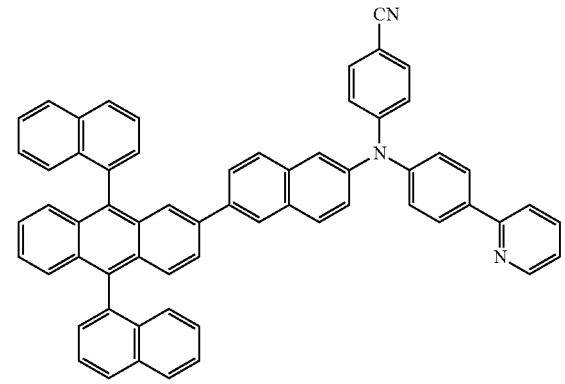

-continued
71
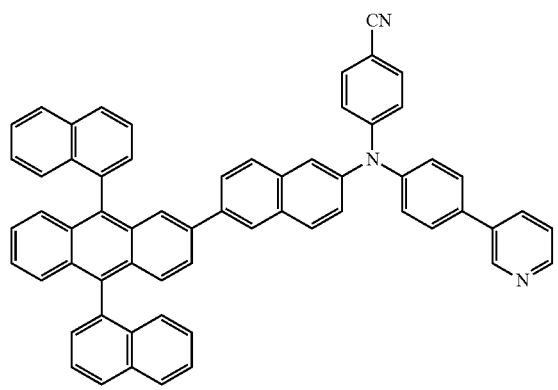
72
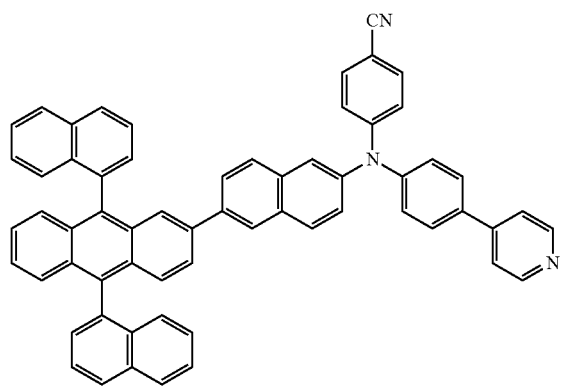
73
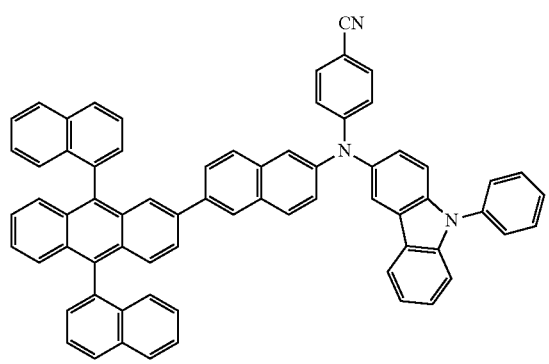
74
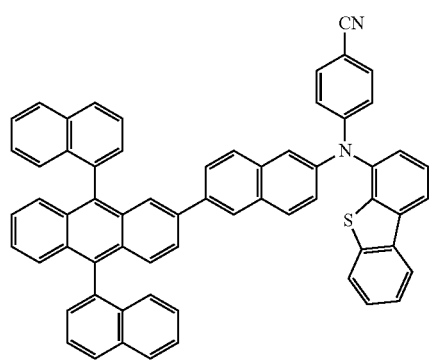
75
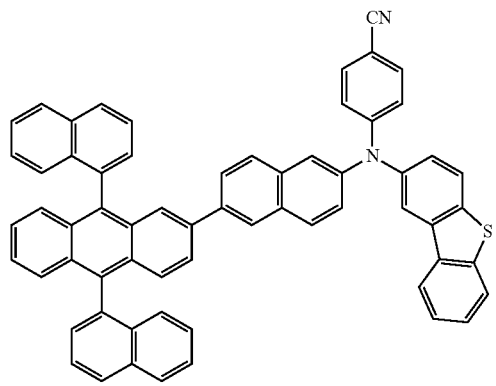
76
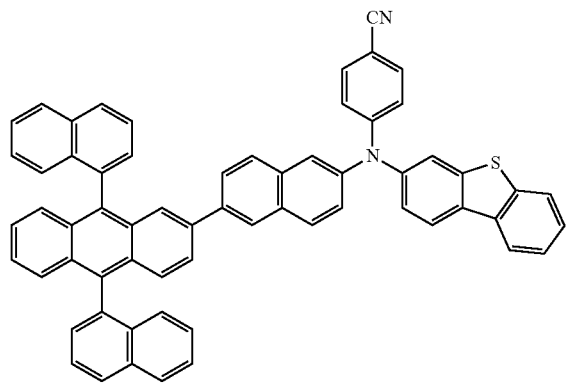
77
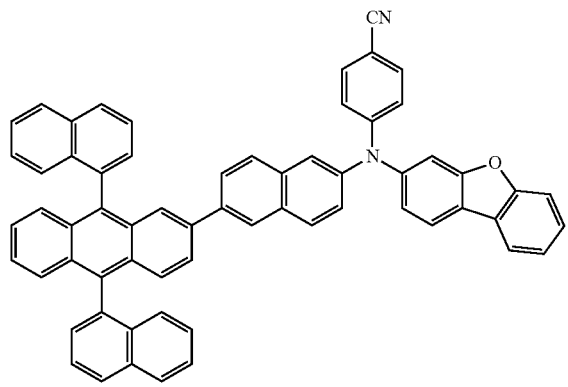
78
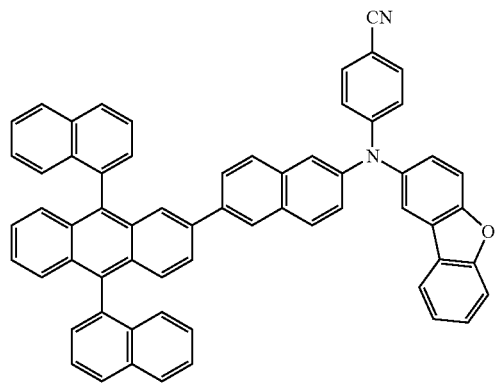

-continued
79
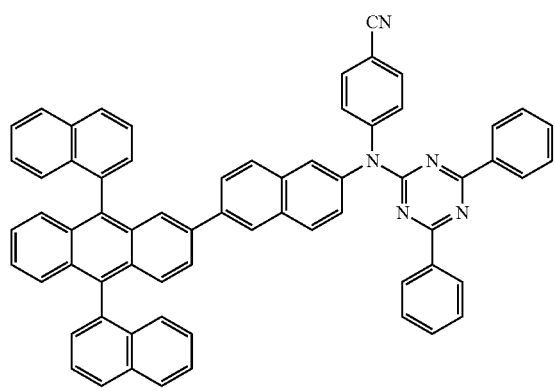
80
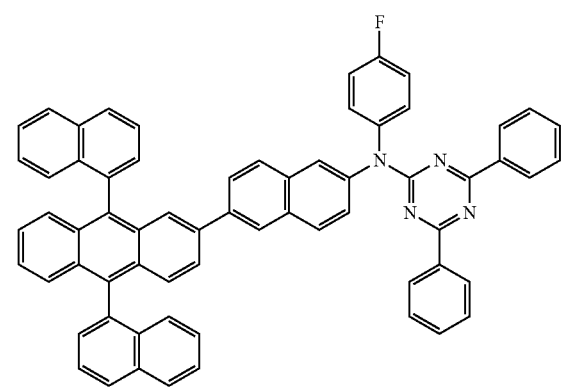
81
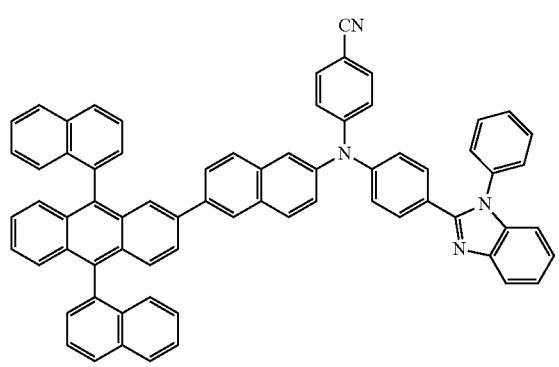
82
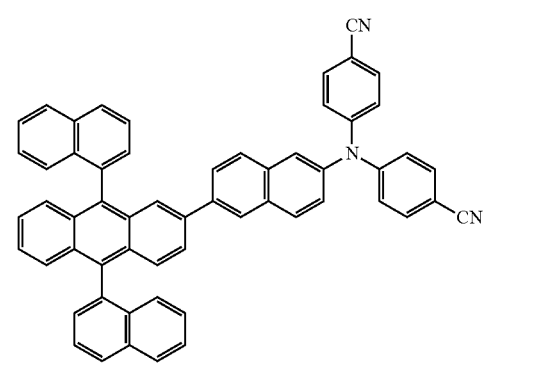
83
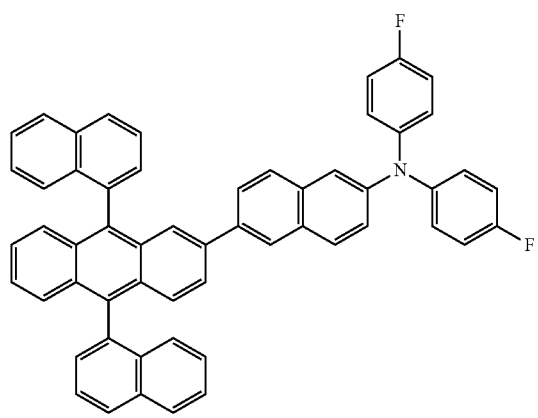
84
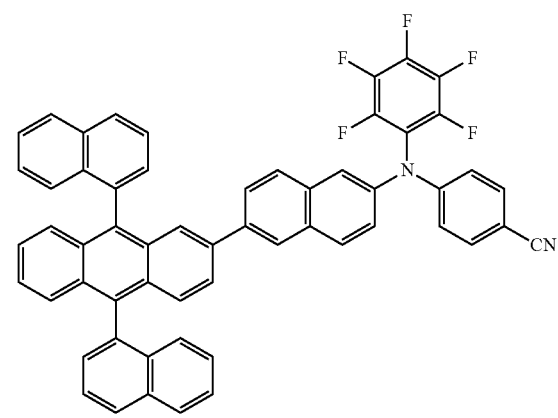
85
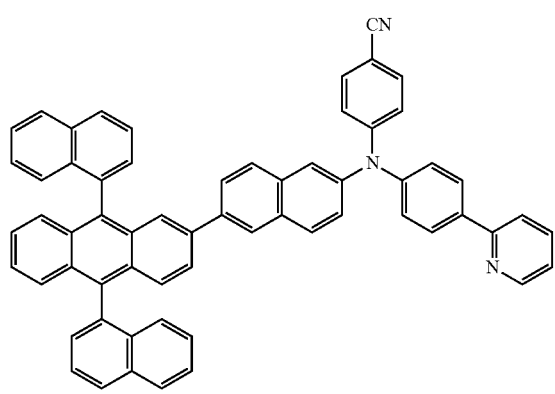
86
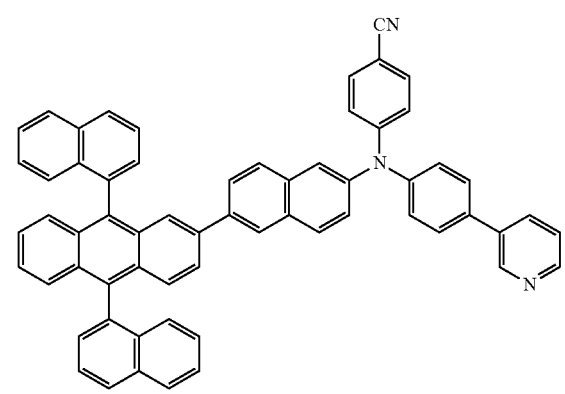

-continued
87
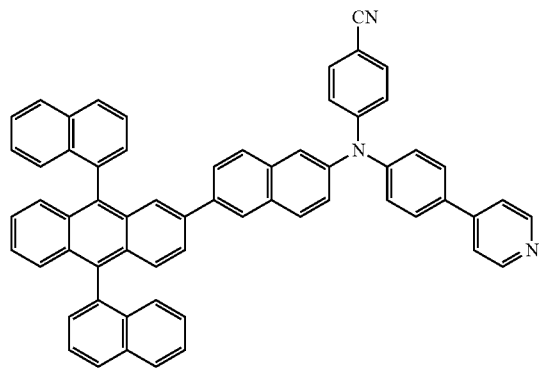
88
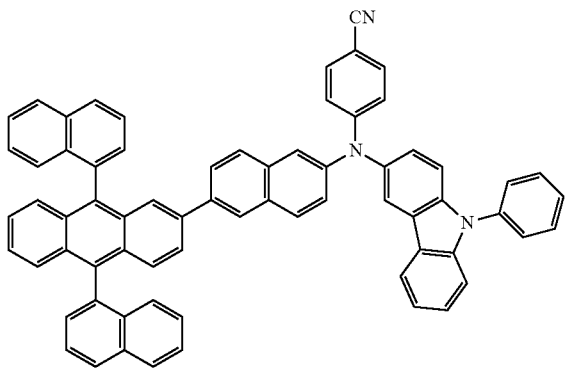
89
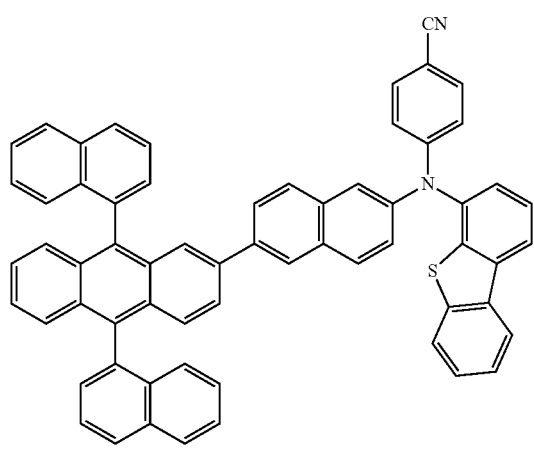
90
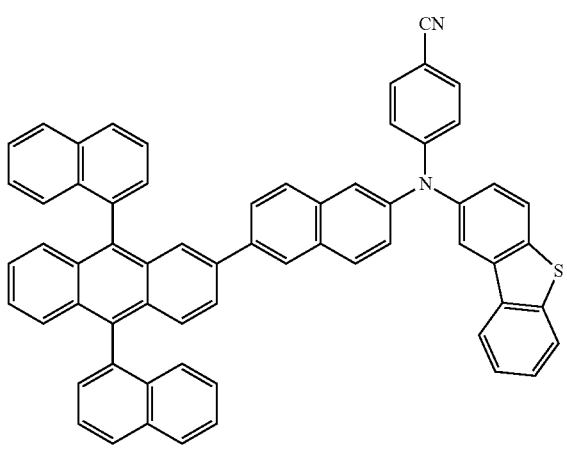
91
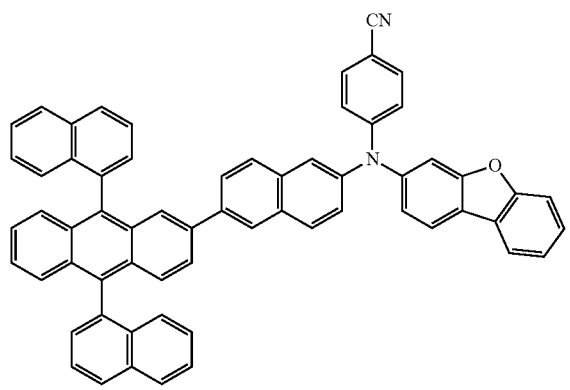
92
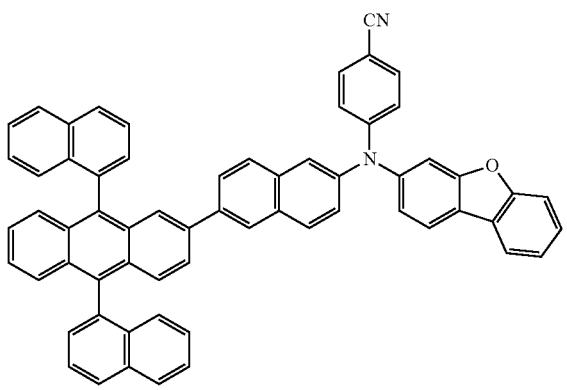
93
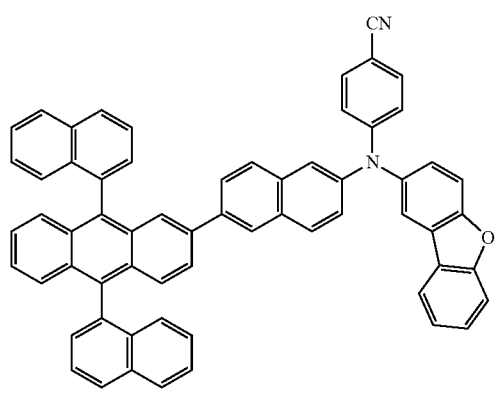
94
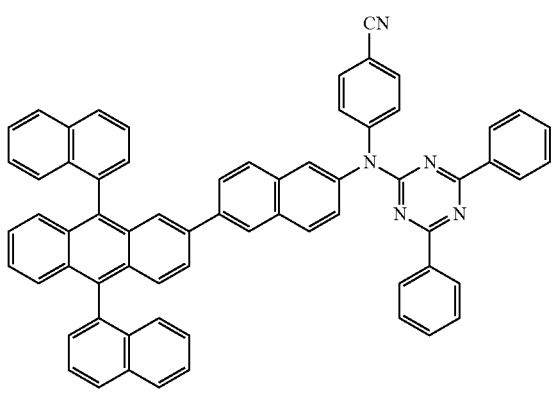

-continued
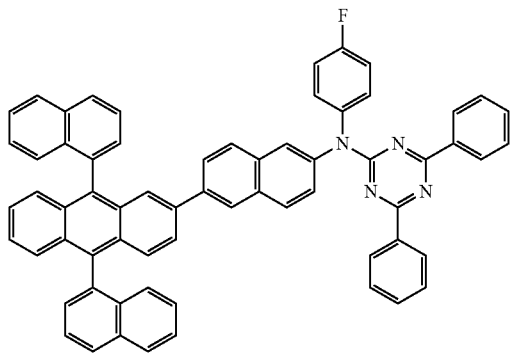
95
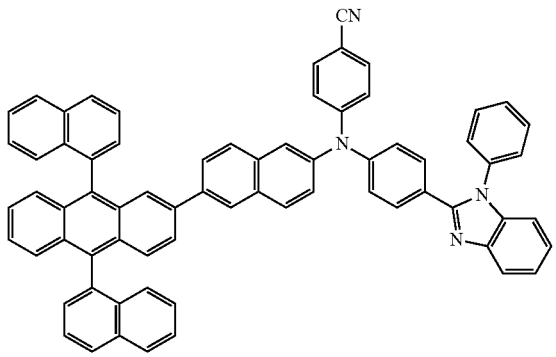
96
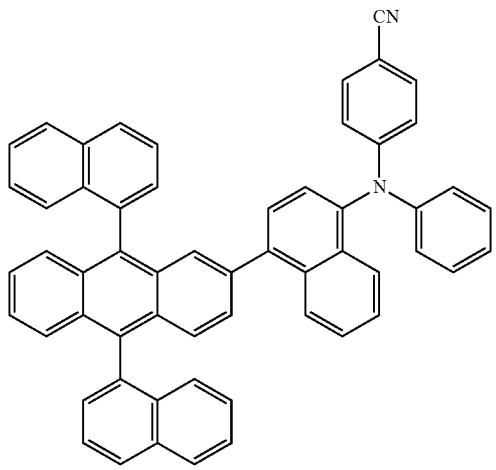
97
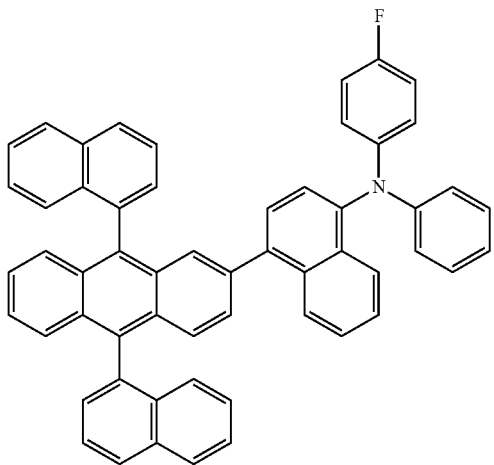
98
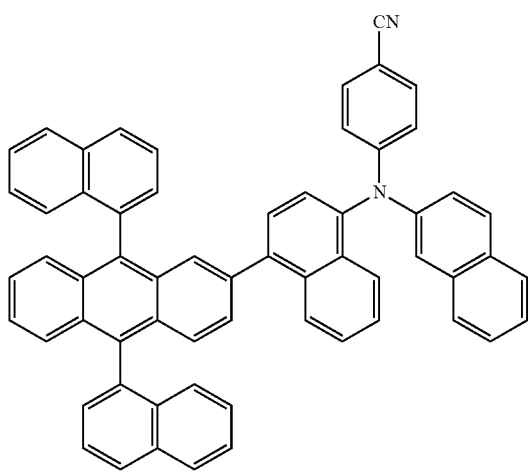
99
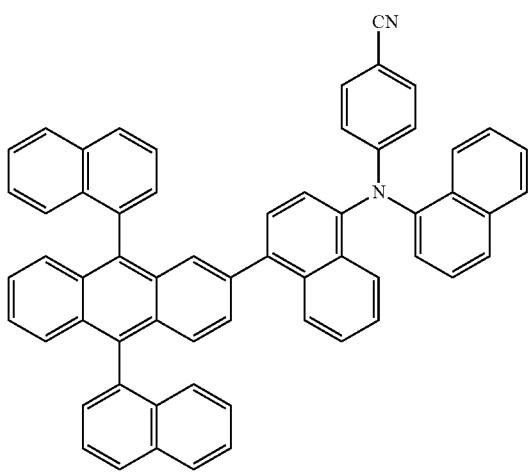
100

-continued
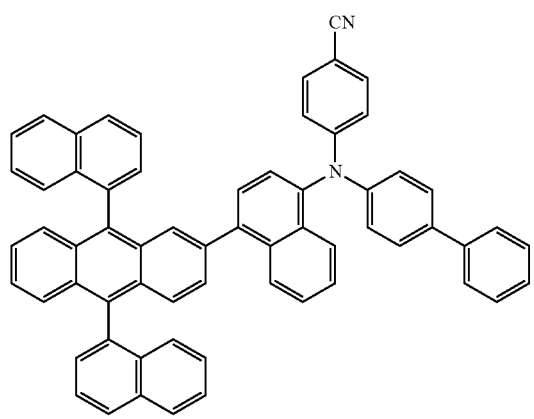
101
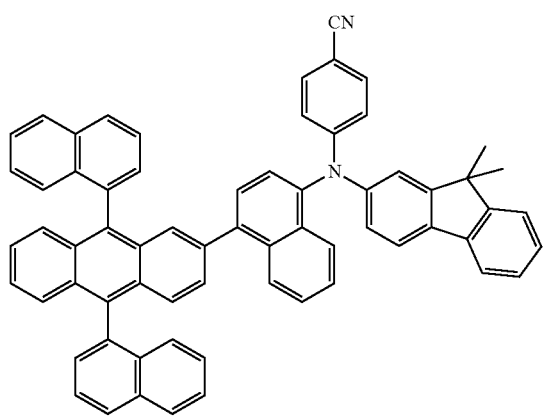
102
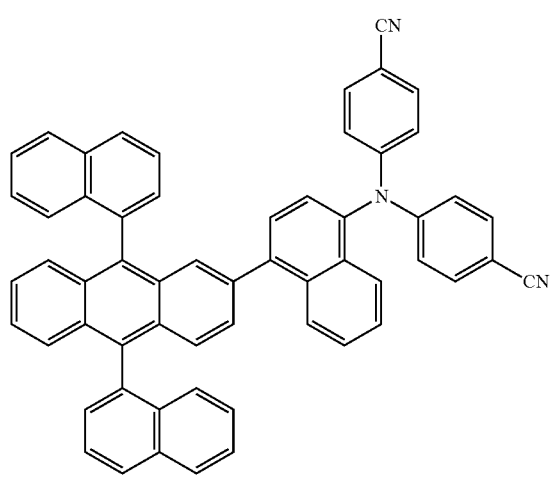
103
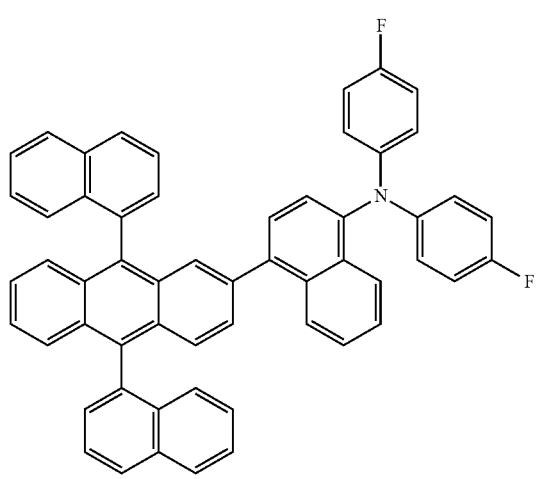
104
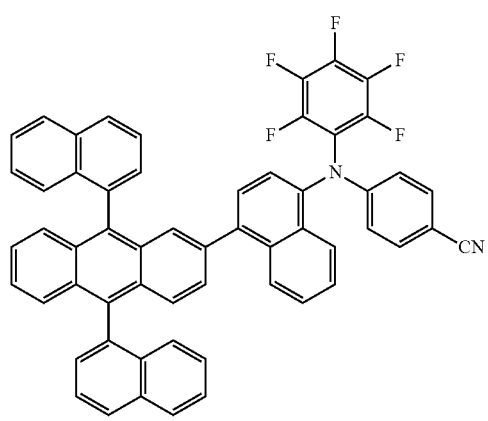
105
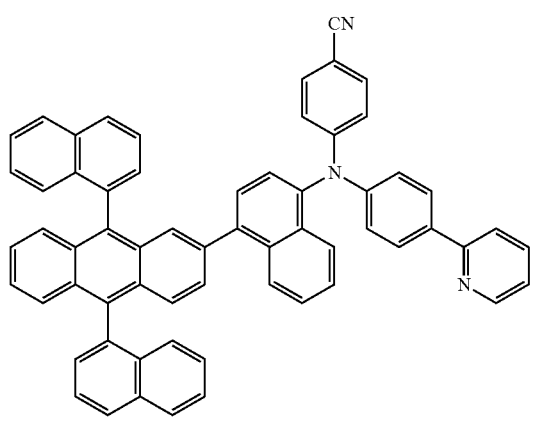
106

-continued
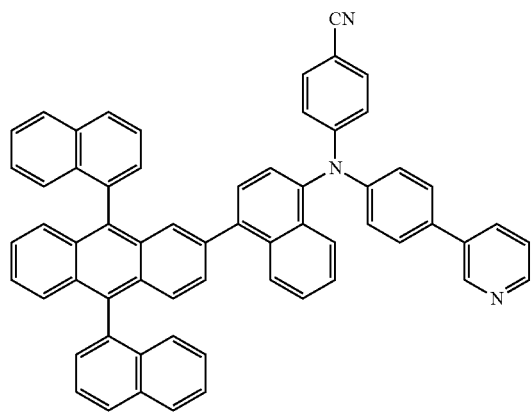
107
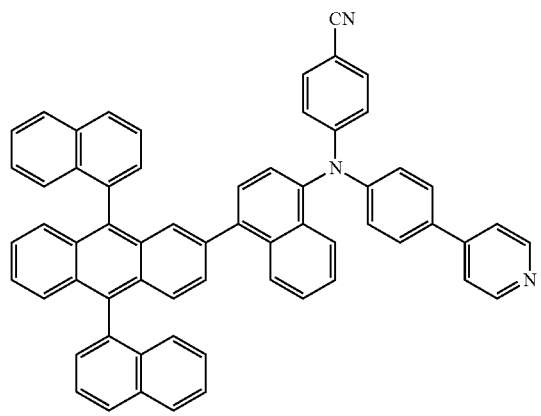
108
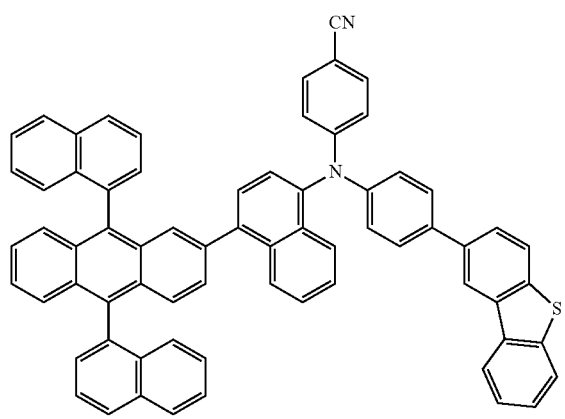
109
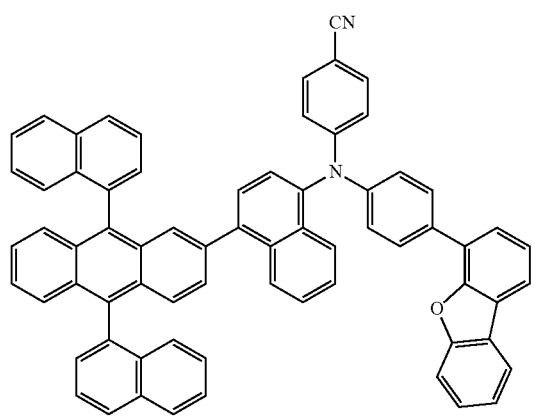
110
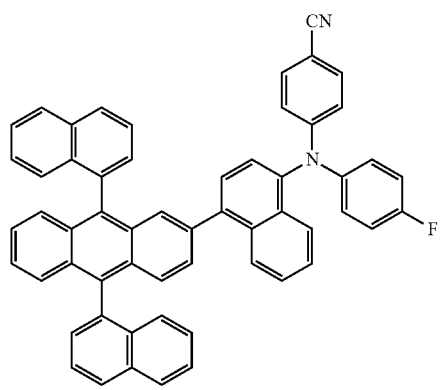
111
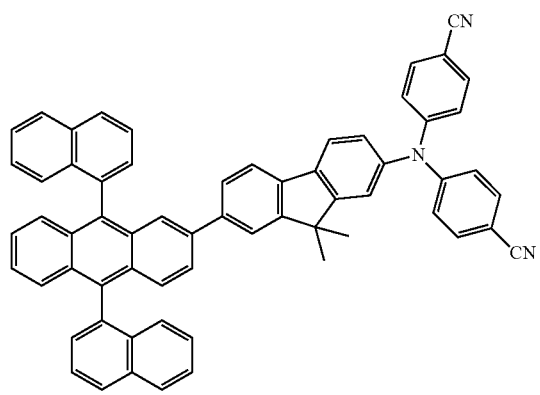
112
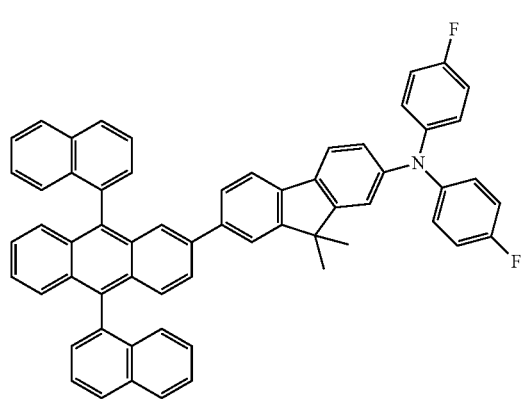
113
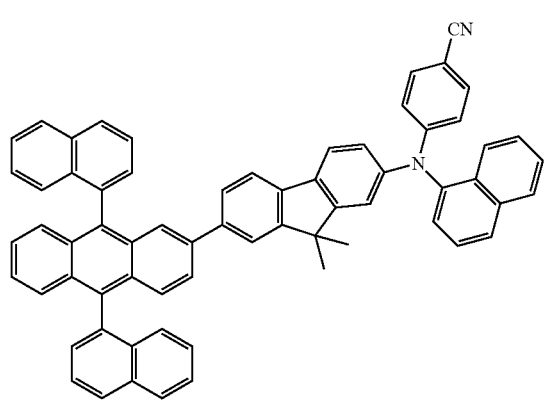
114

-continued
115
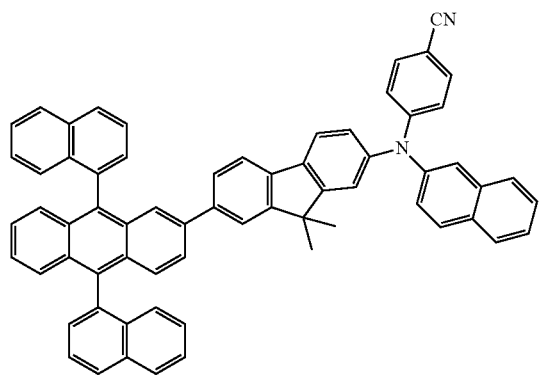
116
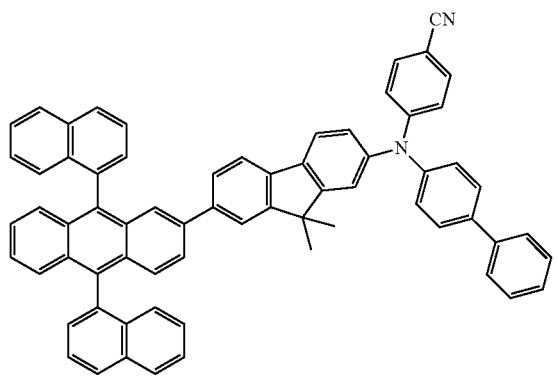
117
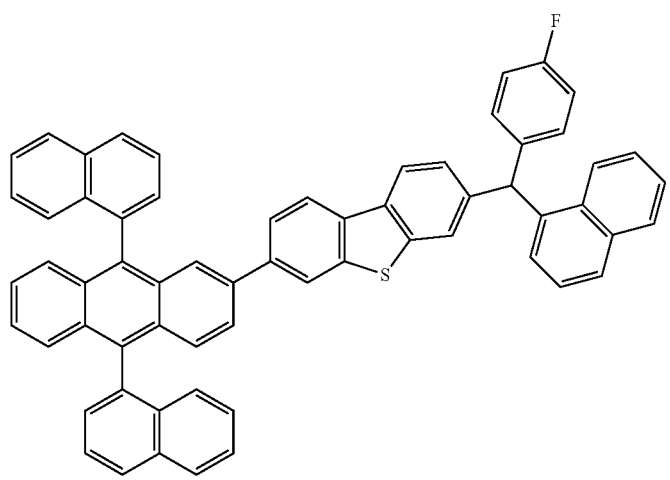
118
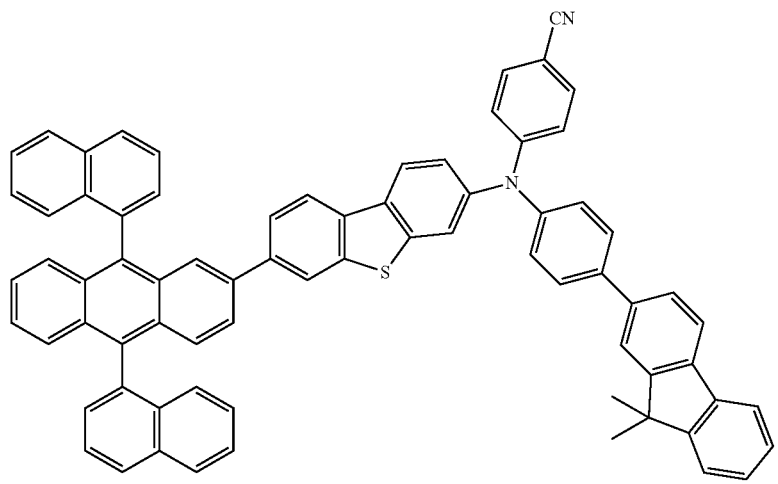

-continued
119
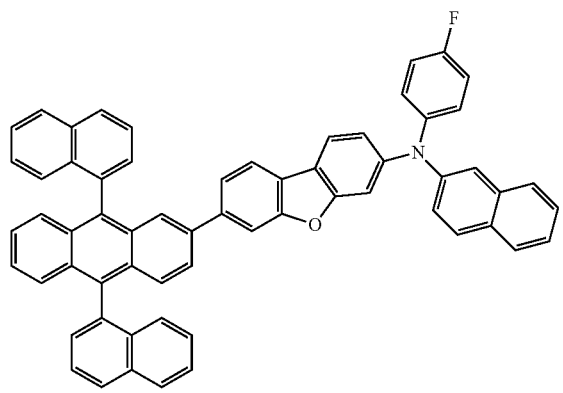
120
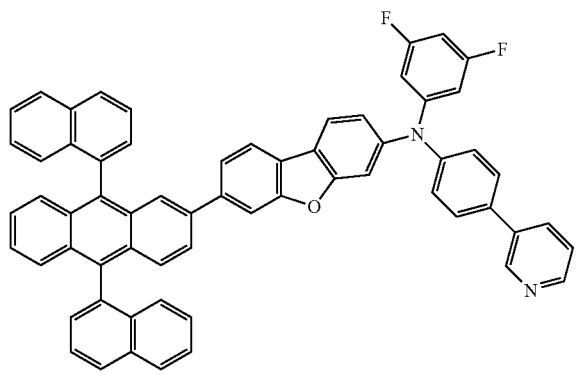
121
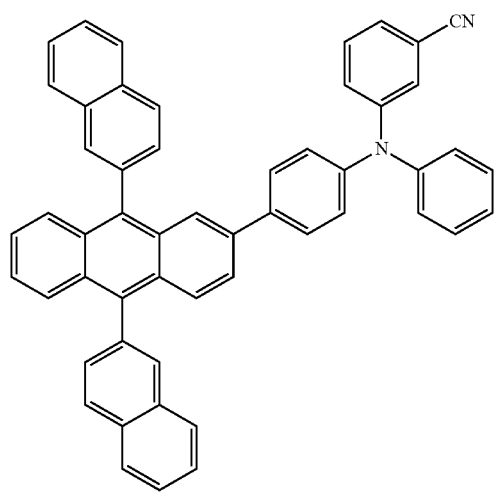
122
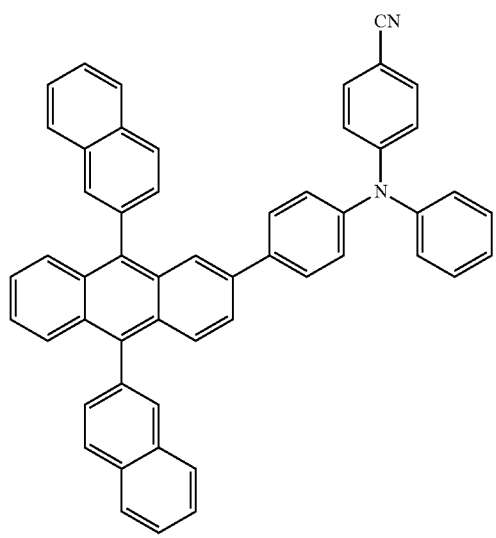
123
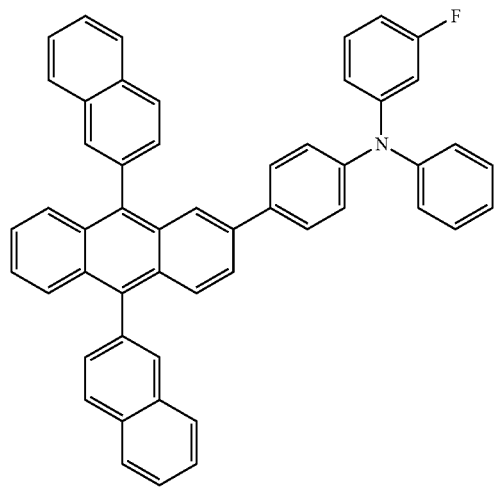
124
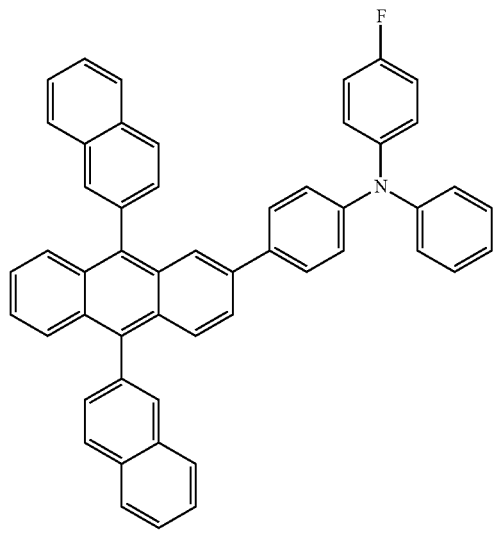

-continued
125 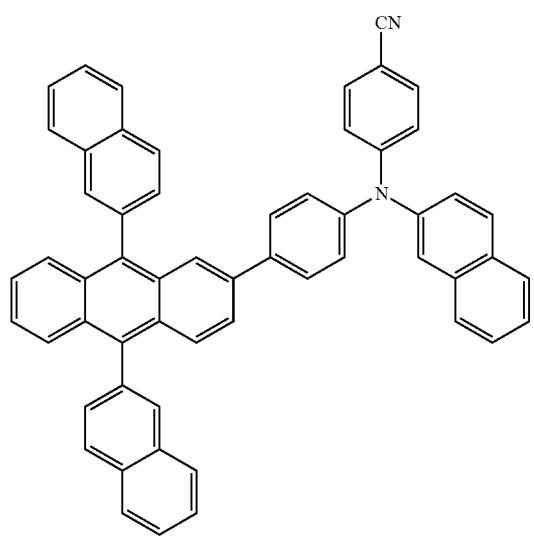
126 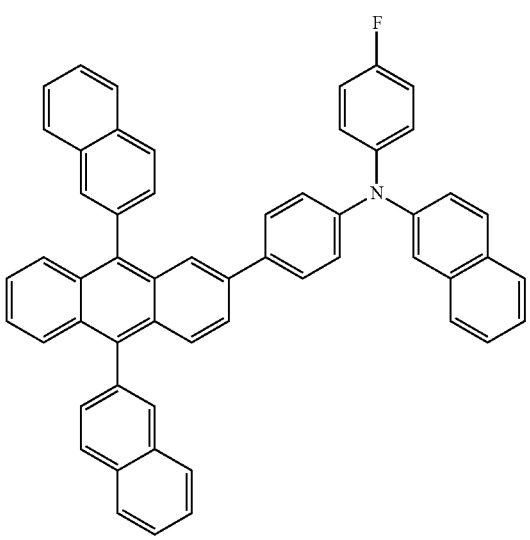
127 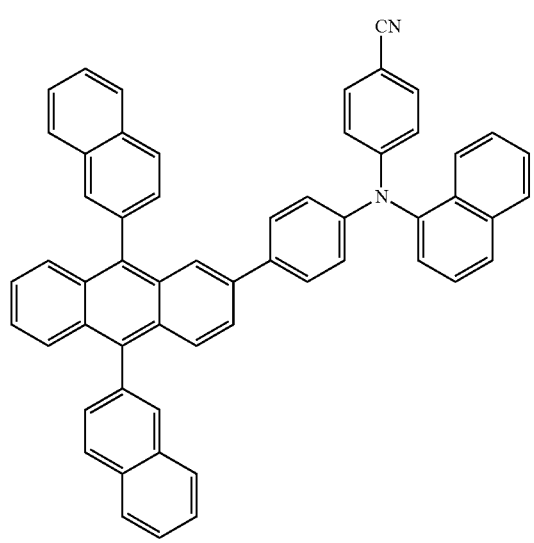
128 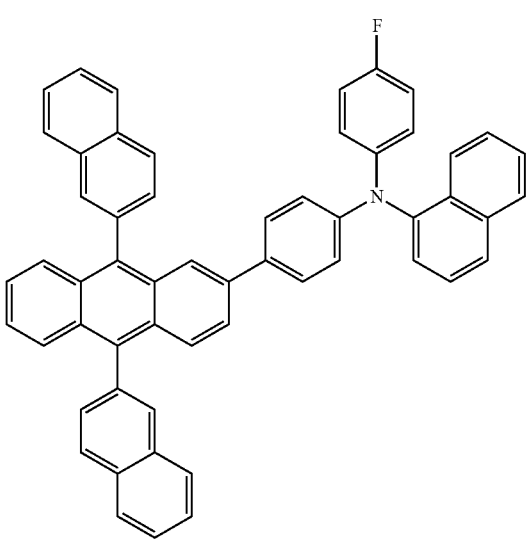
129 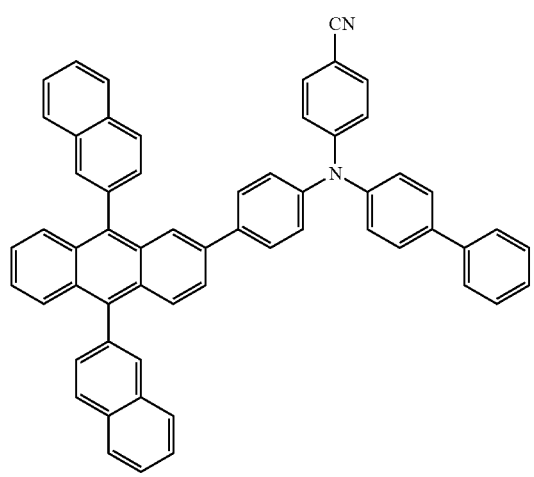
130 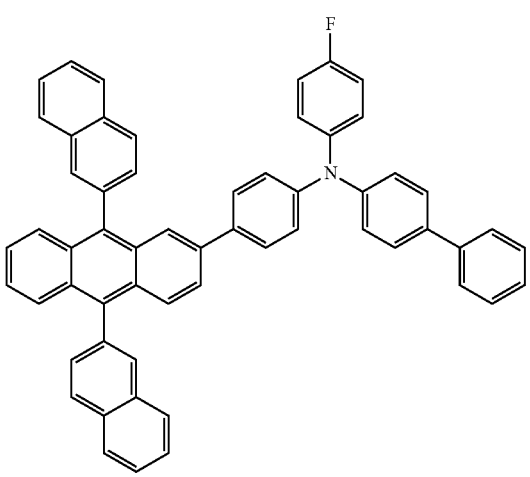

-continued
131
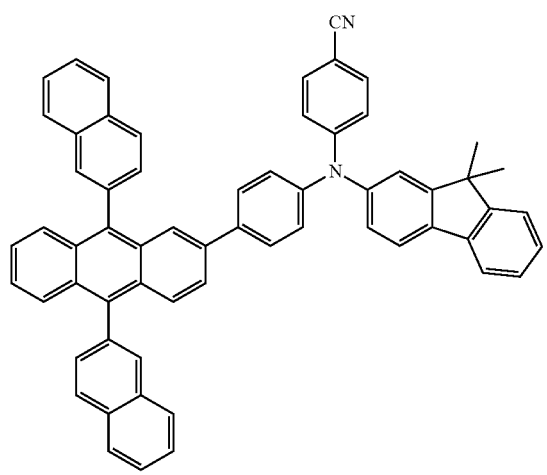
132
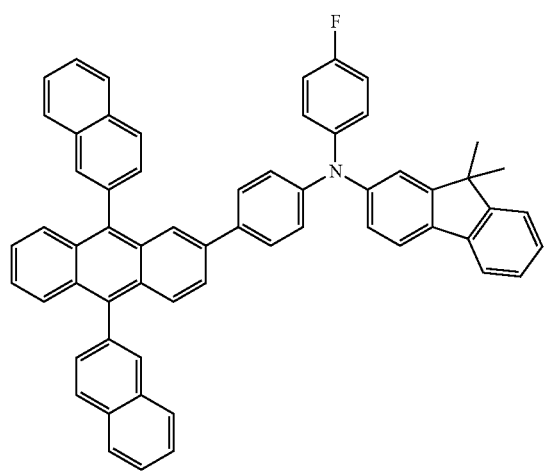
133
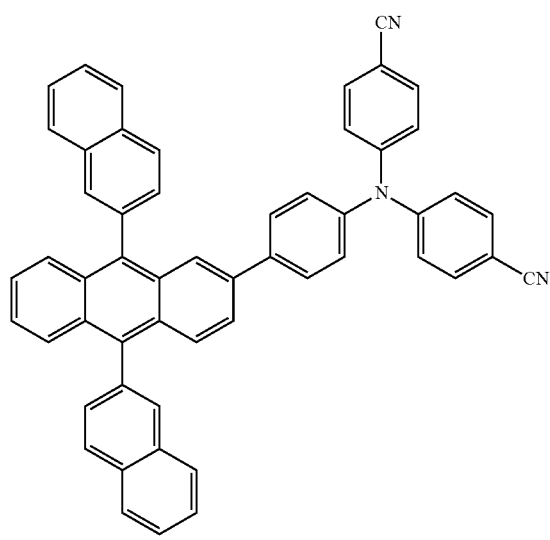
134
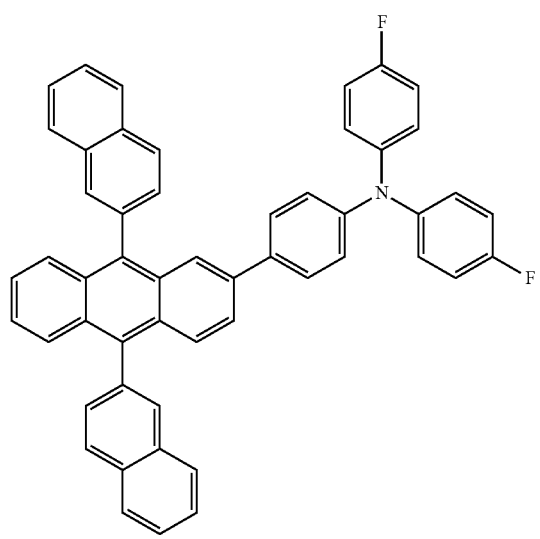
135
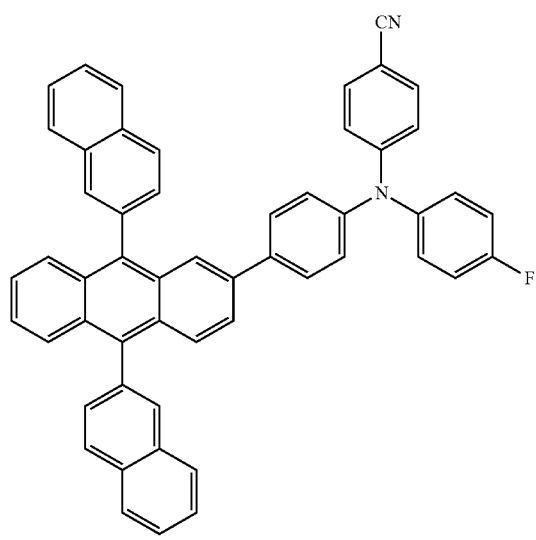
136
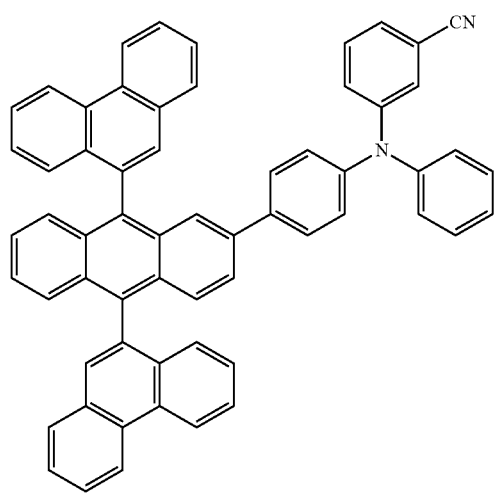

-continued
137
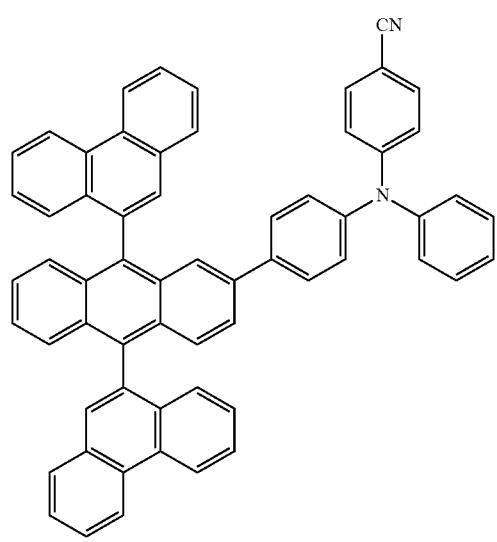
138
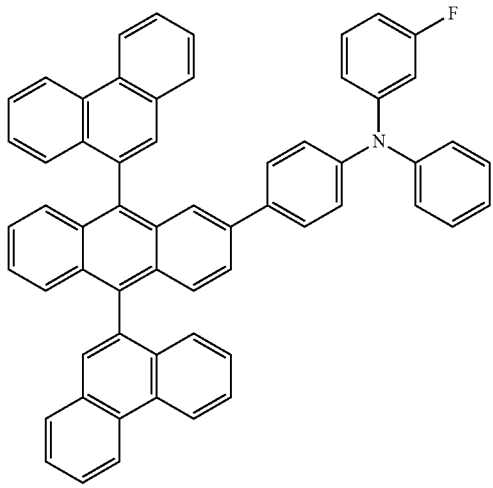
139
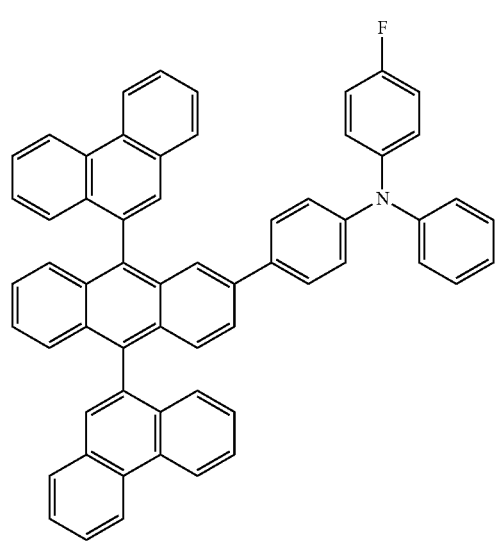
140
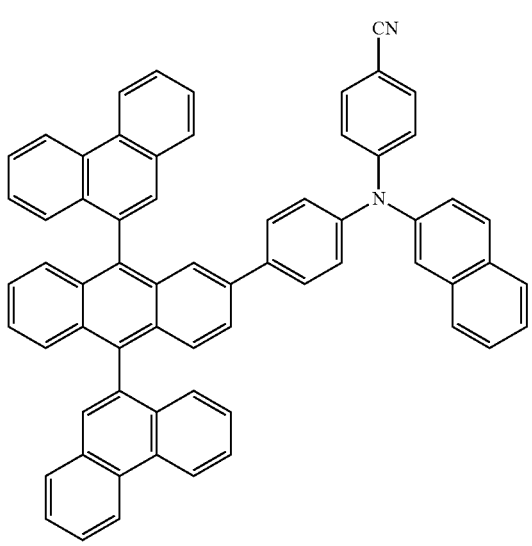
141
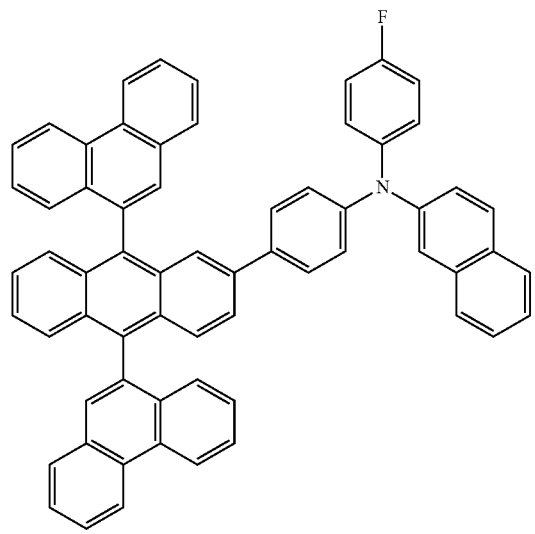
142
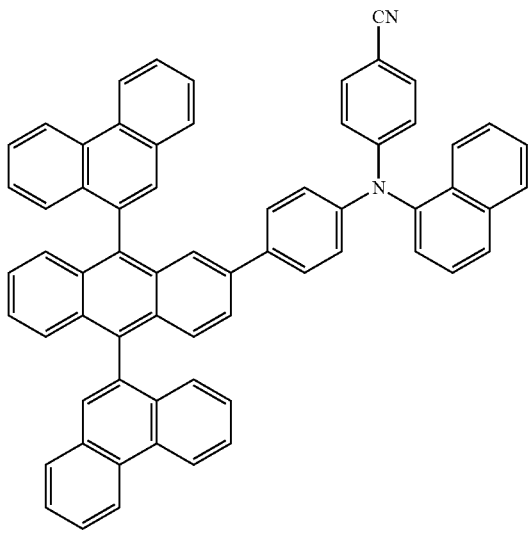

-continued
143
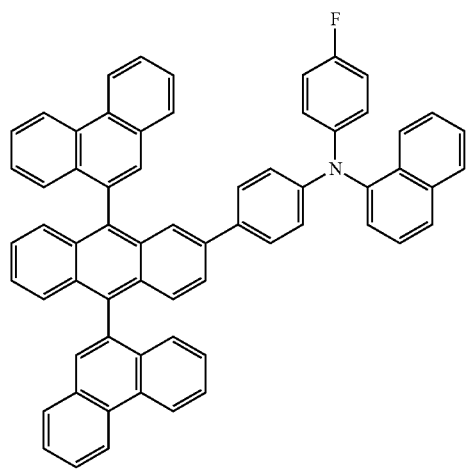
144
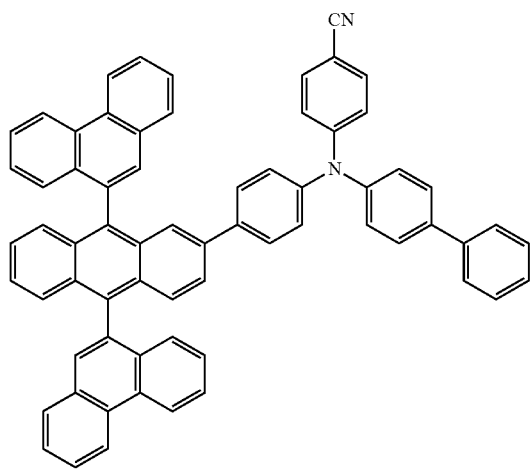
145
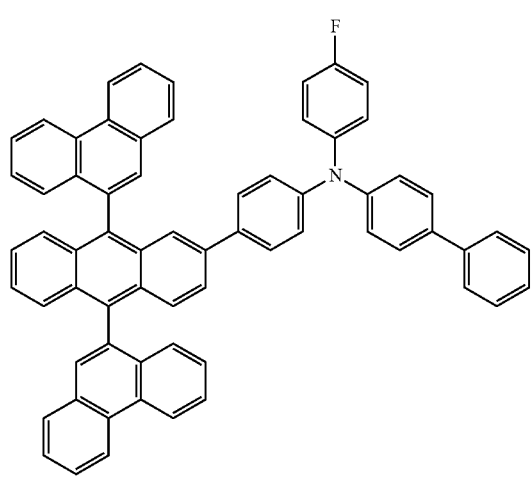
146
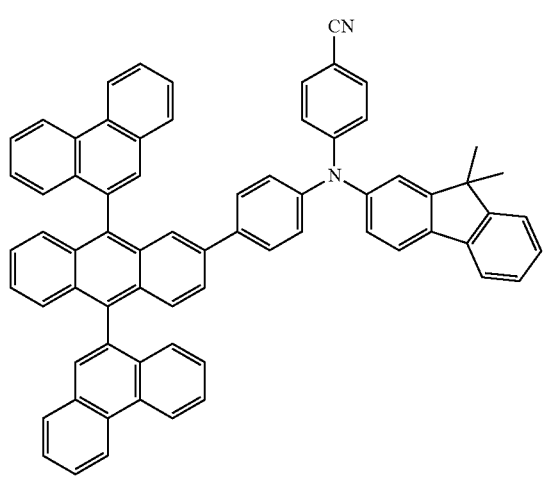
147
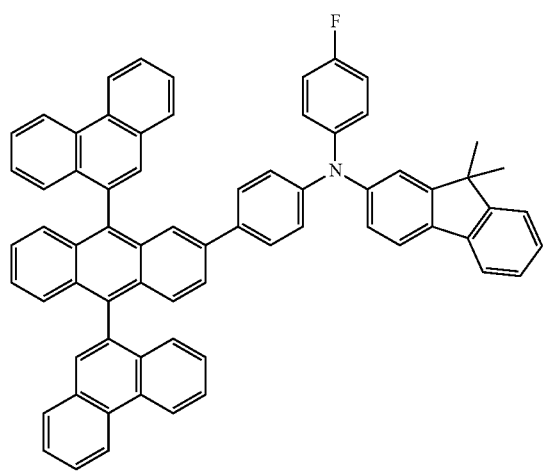
148
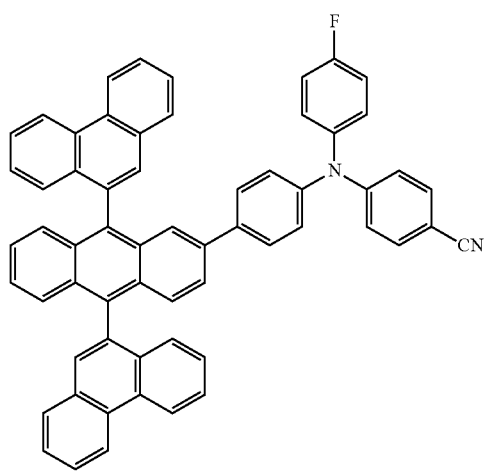

-continued
149 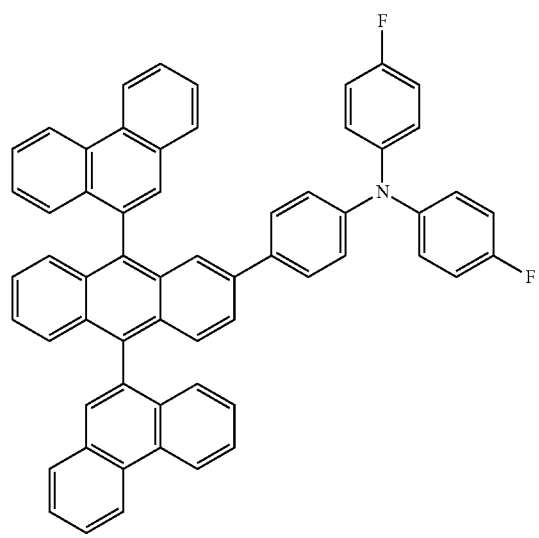
150 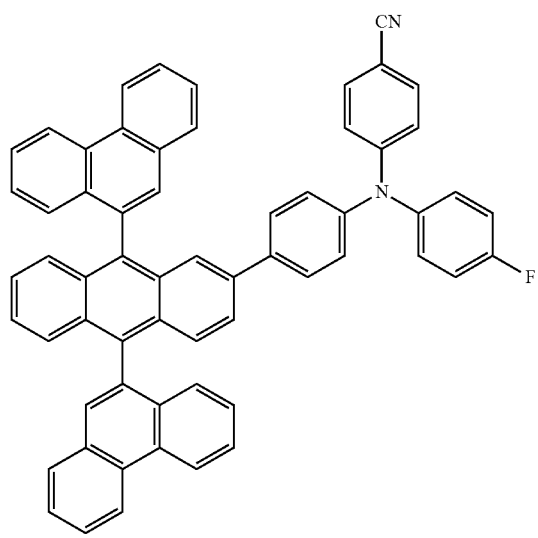
151 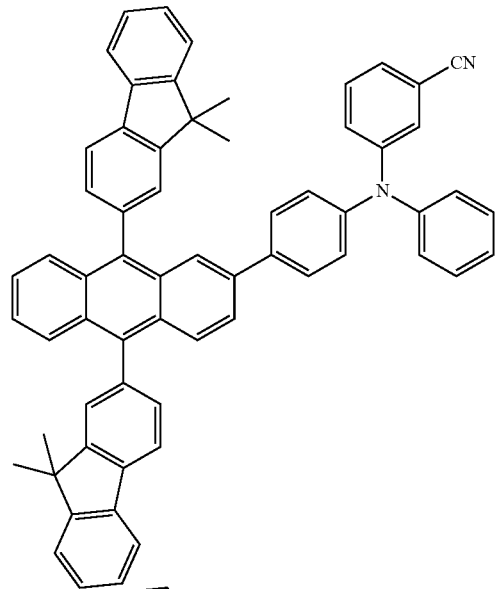
152 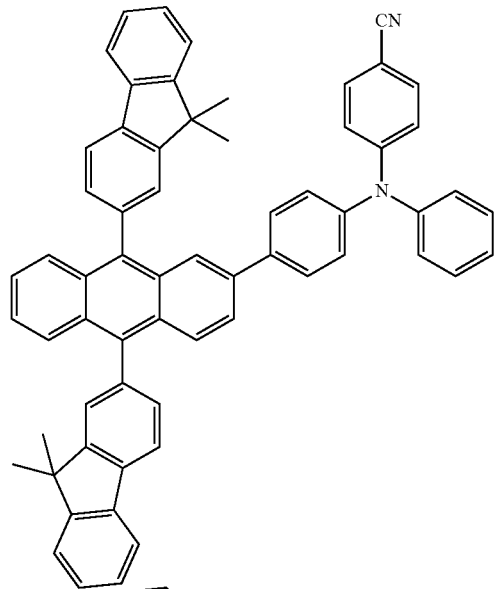
153 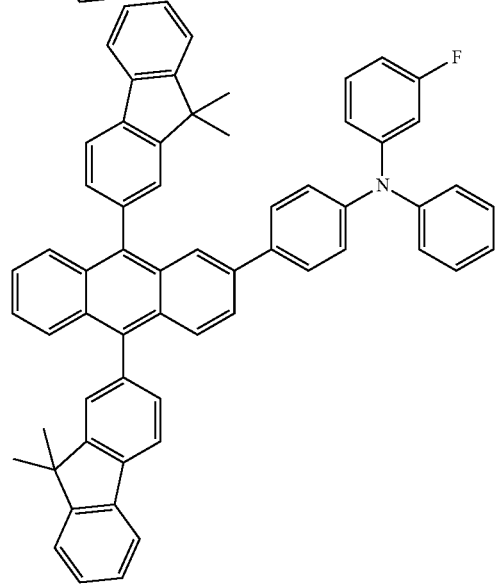
154 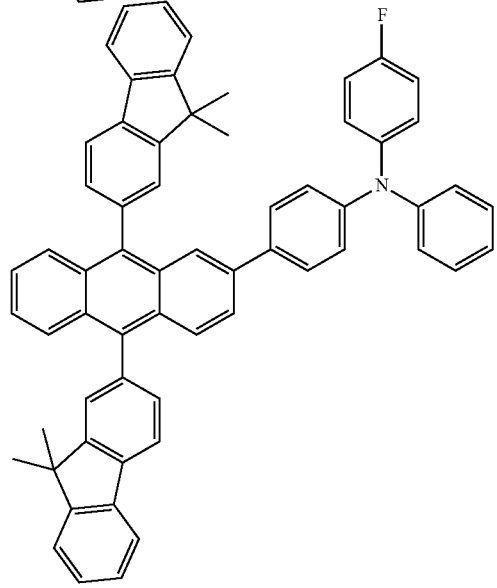

155 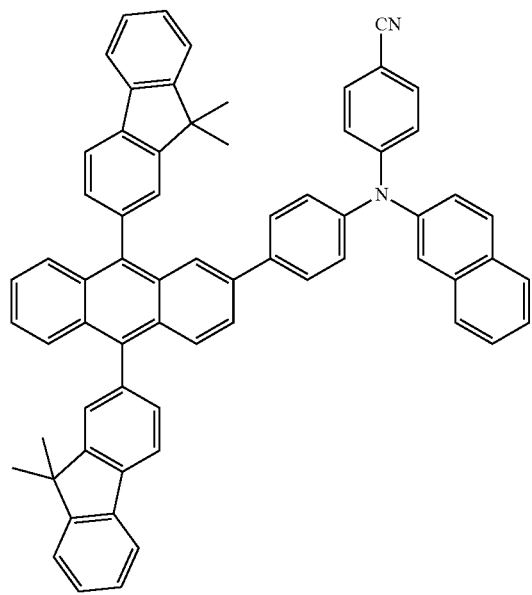
156 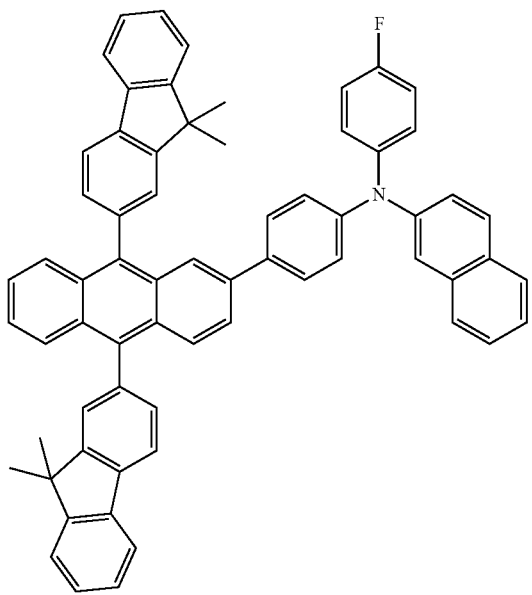
157 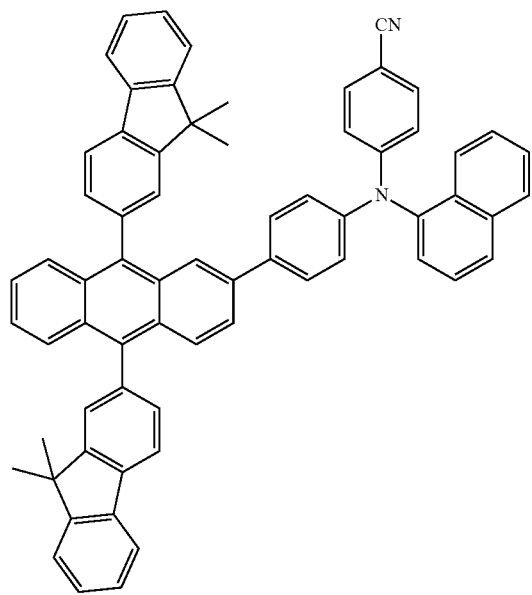
158 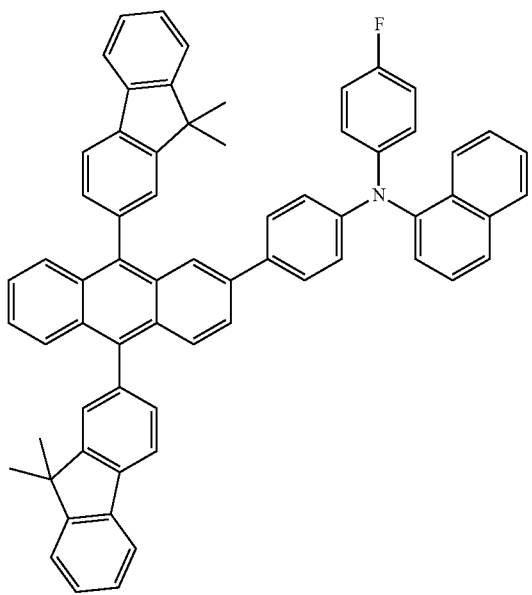

-continued
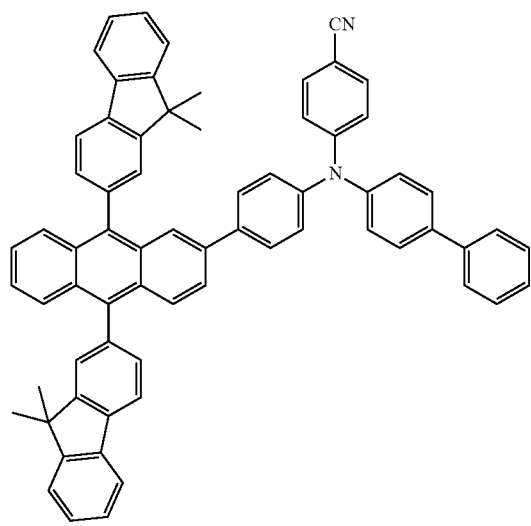
159
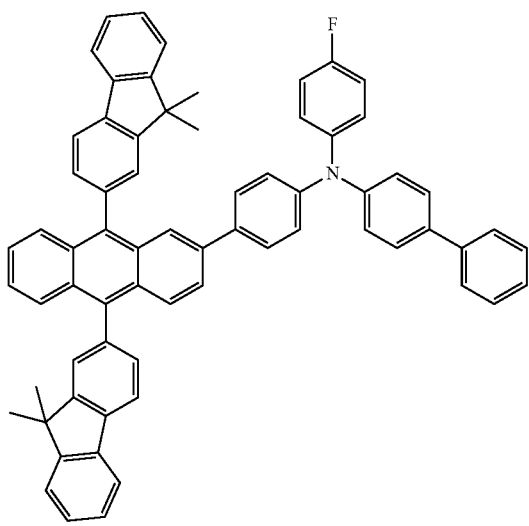
160
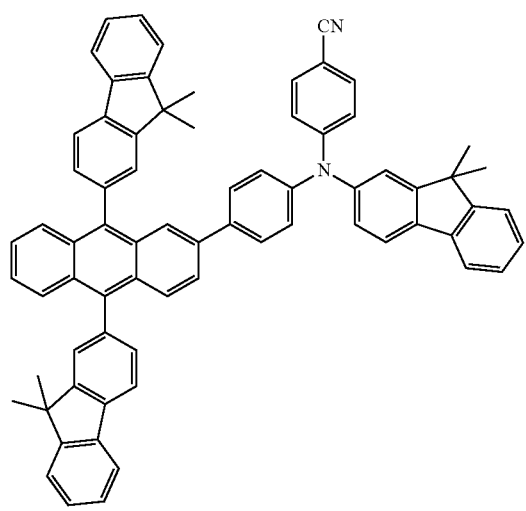
161
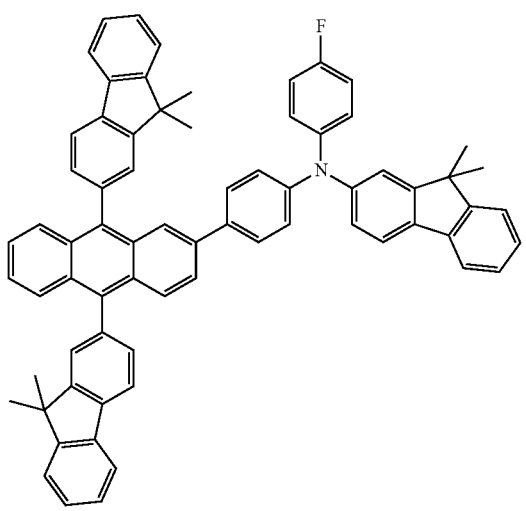
162
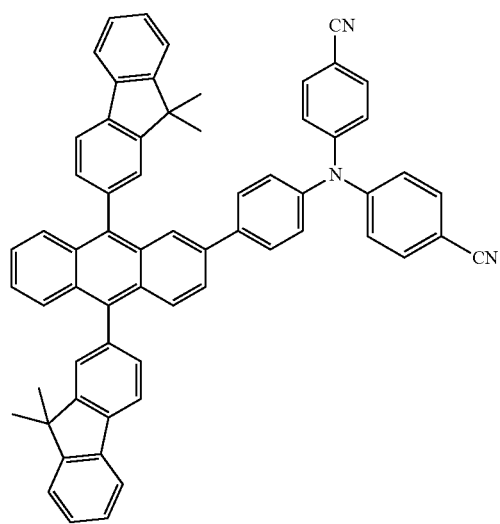
163
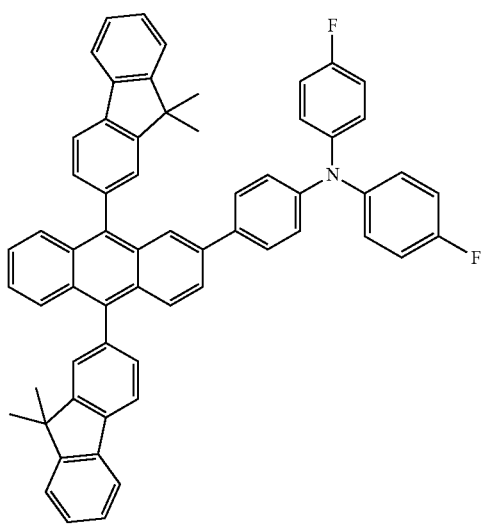
164

-continued
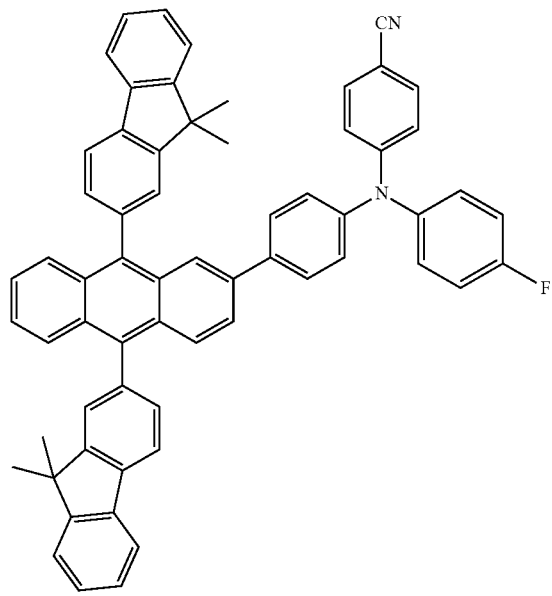
165
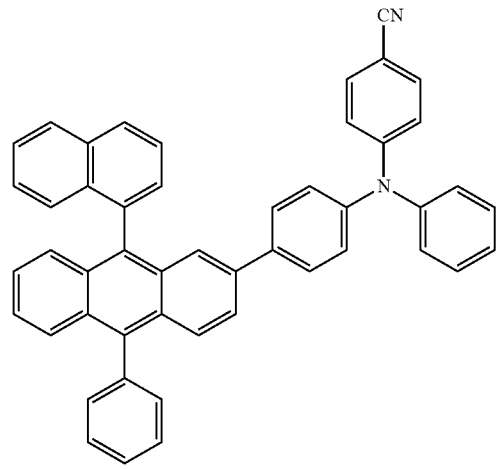
166
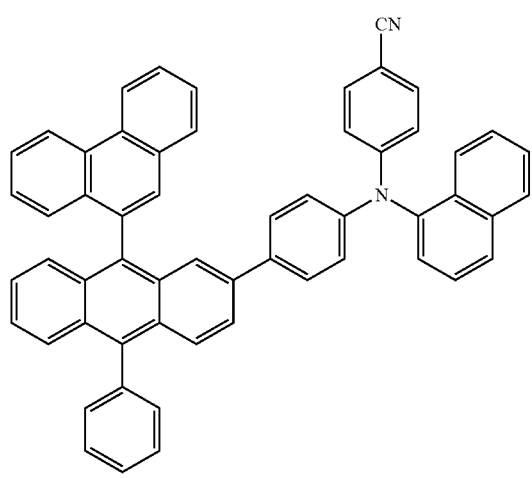
167
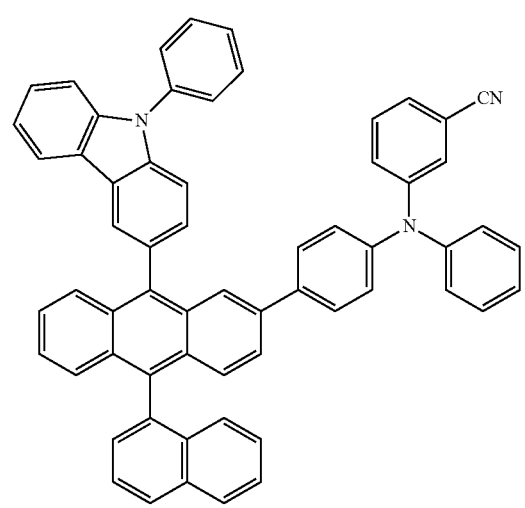
168
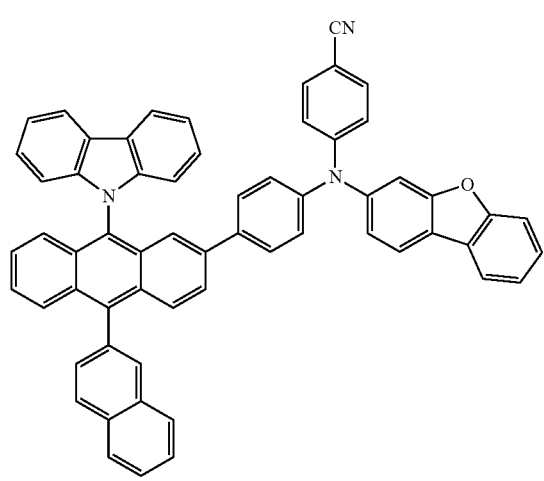
169
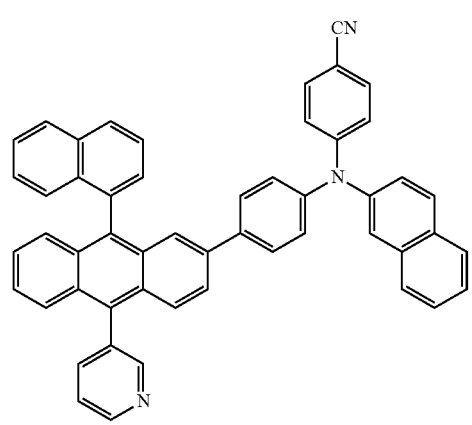
170

-continued

According to another aspect of the present embodiments, an OLED includes a first electrode; a second electrode; and an organic layer that is disposed between the first electrode and the second electrode and includes the compound of Formula 1 above.

The organic layer may include at least one layer selected from a hole injection layer (HIL), a hole transport layer (HTL), a functional layer having both hole injection and hole transport capabilities (hereinafter, referred as a "H-functional layer"), a buffer layer, an electron blocking layer (EBL), an emission layer (EML), a hole blocking layer (HBL), an electron transport layer (ETL), an electron injection layer (EIL), and a functional layer having both electron injection and electron transport capabilities (hereinafter, referred as an "E-functional layer").

In greater detail, the organic layer may be an EML, and the compound may be used as a fluorescent host, a phosphorescent host, or a fluorescent dopant.

In some embodiments, the OLED may include an EIL, an ETL, an EML, a HIL, a HTL, or a H-functional layer having both hole injection and hole transport capabilities, wherein the EML may include the compound of Formulas above; and an anthracene-based compound, an arylamine-based compound, or a styryl-based compound.

In some other embodiments, the OLED may include an EIL, an ETL, an EML, a HIL, a HTL, or a H-functional layer having both hole injection and hole transport capabilities, wherein at least one of a red EML, a green EML, a blue EML, and a white EML of the EML may include a phosphorescent compound, and the HIL, the HTL, or the H-functional layer having both hole injection and hole transport capabilities may include a charge-generating material. The charge-generating material may be a p-dopant, and the p-dopant may be a quinone derivative, a metal oxide, and a cyano group-containing compound.

In some other embodiments, the organic layer may include an ETL, and the ETL may include an electron-transporting organic compound and a metal complex. The metal complex may be a lithium (Li) complex.

The term "organic layer" used herein refers to a single layer and/or a multi-layer disposed between the first electrode and the second electrode of the OLED.

The organic layer includes an EML, and the EML may include the compound of Formulas 1 to 175 above. In some embodiments, the organic layer may include at least one layer of a HIL, a HTL, a H-functional layer having both hole injection and hole transport capabilities, and at least one layer of the HIL, the HTL, and the H-functional layer having both hole injection and hole transport capabilities may include the compound of Formulas 1 to 175 above.

The compound of Formulas 1 to 175 above included in the EML may act as a host. For example, the compound may be a blue fluorescent host emitting blue light. In some embodiments, the compound included in the EML may act as a fluorescent or phosphorescent dopant emitting red light, greed light, or white light.

FIG. 1 is a schematic view of a structure of an OLED according to an embodiment. Hereinafter, a structure and a manufacturing method of an OLED according to an embodiment will be described in detail with reference to FIG. 1.

A substrate (not illustrated), which may be any substrate that is in used in a general OLED, may be a glass substrate or a transparent plastic substrate with excellent mechanical strength, thermal stability, transparency, surface smoothness, ease of handling, and water resistance.

A first electrode may be formed by depositing or sputtering a material for a first electrode on the substrate. When the first electrode is an anode, the material for the first electrode may be selected from materials with a high work function to enable ease of hole injection. The first electrode may be a reflective electrode or a transmission electrode. The material for the first electrode may be a transparent material with high conductivity, and examples thereof are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode may be used as a reflective electrode.

The first electrode may have a single-layer structure or a multi-layer structure including at least two layers. For example, the first electrode may have a three-layered structure of ITO/Ag/ITO, but is not limited thereto.

The organic layer may be disposed on the first electrode.

The organic layer may include a HIL, a HTL, a buffer layer (not illustrated), an EML, an ETL, or an EIL.

A HIL may be formed on the first electrode by using various methods such as vacuum deposition, spin coating, casting, and Langmuir-Blodgett (LB) deposition.

When the HIL is formed using vacuum deposition, vacuum deposition conditions may vary depending on the compound that is used to form the HIL, and the desired structure and thermal properties of the HIL to be formed. For example, the vacuum deposition may be performed at a temperature of about 100° C. to about 500° C., a pressure of about $10^{-8}$ torr to about $10^{-3}$ torr, and a deposition rate of about 0.01 Å/sec to about 100 Å/sec. However, the deposition conditions are not limited thereto.

When the HIL is formed using spin coating, the coating conditions may vary depending on the compound that is used to form the HIL, and the desired structure and thermal properties of the HIL to be formed. For example, the coating rate may be in a range from about 2,000 rpm to about 5,000 rpm, and a temperature at which heat treatment is performed to remove a solvent after coating may be in a range from about 80° C. to about 200° C. However, the coating conditions are not limited thereto.

As a material for the HIL, a known hole-injecting material, for example, N,N'-diphenyl-N,N'-bis-[4-(phenyl-m-tolyl-amino)-phenyl]-biphenyl-4,4'-diamine (DNTPD), a phtalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), or polyaniline/poly(4-styrenesulfonate) (PANI/PSS) may be used, but the hole-injecting material is not limited thereto:

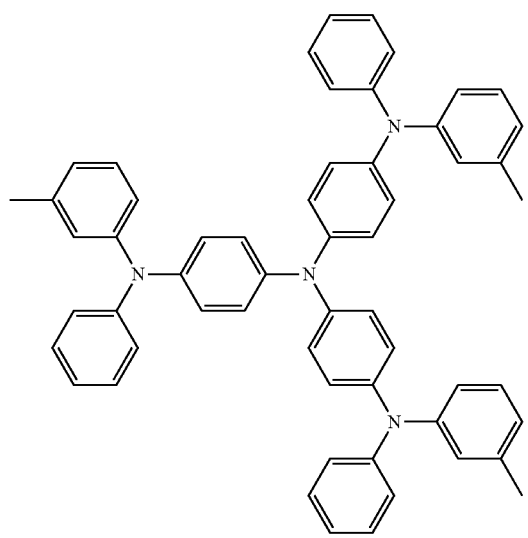

m-MTDATA

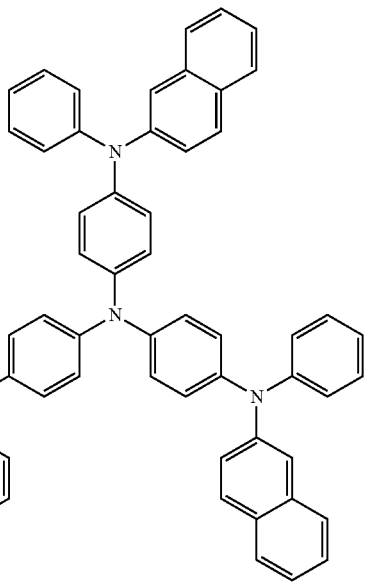

2-TNATA

A thickness of the HIL may be in a range from about 100 Å to about 10,000 Å, for example, from about 100 Å to about 1000 Å. When the thickness of the HIL is within the above ranges, the HIL may have satisfactory hole injection characteristics without a substantial increase in a driving voltage.

Then, a HTL may be formed on the HIL by using vacuum deposition, spin coating, casting, LB deposition, or the like. When the HTL is formed using vacuum deposition or spin coating, the deposition and coating conditions may be similar to those for the formation of the HIL, although the deposition and coating conditions may vary depending on a compound that is used to form the HTL.

As a material for the HTL, a known hole-transporting material, for example, a carbazole derivative such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine) (TCTA), and N,N'-di(1-naphthyl)-N,N'-diphenylbenzidine (NPB) may be used, but the hole-transporting material is not limited thereto:

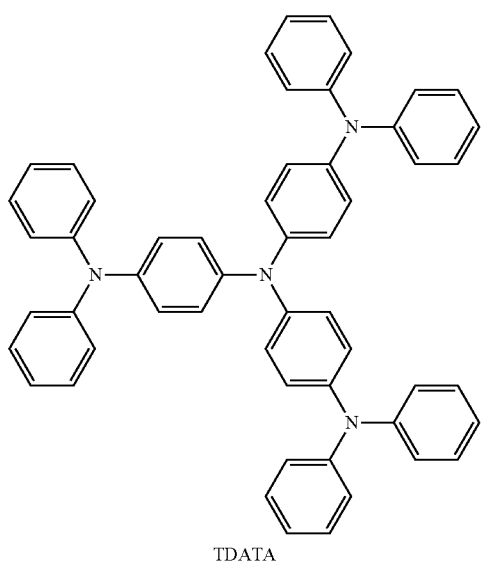

TDATA

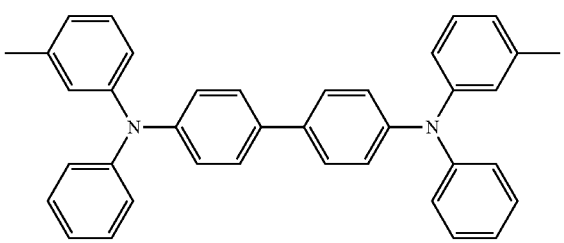

TPD

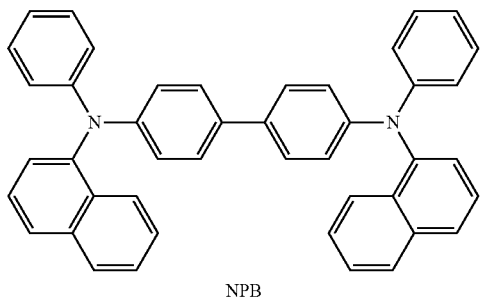

NPB

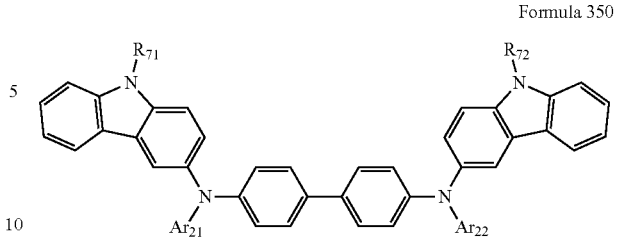

Formula 350

A thickness of the HTL may be in a range from about 50 Å to about 20,000 Å, for example, from about 100 Å to about 1,500 Å. When the thickness of the HTL is within the above ranges, the HTL may have satisfactory hole transport characteristics without a substantial increase in a driving voltage.

The H-functional layer (a functional layer having both hole injection and hole transport capabilities) may include one or more materials selected from the above-described materials for the HIL and the HTL. A thickness of the H-functional layer may be in a range from about 500 Å to about 10,000 Å, for example, from about 100 Å to about 1,000 Å. When the thickness of the H-functional layer is within the above ranges, the H-functional layer may have satisfactory hole injection and transport characteristics without a substantial increase in a driving voltage.

In some embodiments, at least one layer of the HIL, the HTL, and the H-functional layer may include at least one of the following compounds represented by Formulas 300 and 350 below:

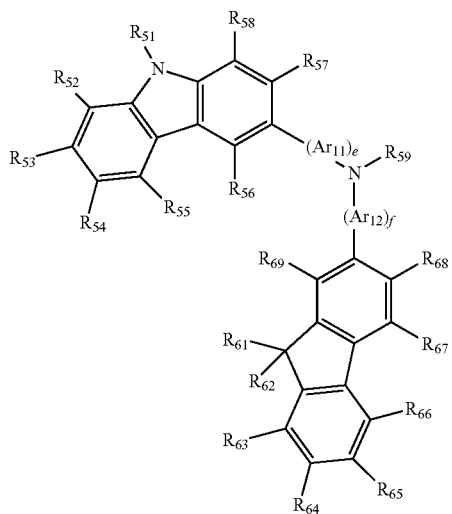

Formula 300

$Ar_{11}$, $Ar_{12}$, $Ar_{21}$, and $Ar_{22}$ in Formula 300 may be each independently a substituted or unsubstituted $C_5$-$C_{60}$ arylene group.

e and f in Formula 300 may be each independently an integer from 0 to 5, for example, 0, 1, or 2. In some embodiments, e may be 1 and f may be 0, but are not limited thereto.

$R_{51}$ to $R_{58}$, $R_{61}$ to $R_{69}$ and $R_{71}$, and $R_{72}$ in Formulas 300 and 350 may be each independently a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$ and $R_{71}$, and $R_{72}$ may be each independently selected from a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid or a salt thereof; a phosphoric acid or a salt thereof; a $C_1$-$C_{10}$ alkyl group (e.g., a methyl group, an ethyl group, a propyl group, a butyl group, a pentyl group, a hexyl group, or the like); a $C_1$-$C_{10}$ alkoxy group (e.g., a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;

a phenyl group; a naphtyl group; an anthryl group; a fluorenyl group; a pyrenyl group; and a phenyl group, a naphtyl group, an anthryl group, a fluorenyl group, and a pyrenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but is not limited thereto.

$R_{59}$ in Formula 300 may be selected from a phenyl group; a naphtyl group; an anthryl group; a biphenyl group; a pyridyl group; and a phenyl group, a naphtyl group, an anthryl group, a biphenyl group, and a pyridyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

In some embodiments, the compound of Formula 300 may be represented by 300A below, but the compound is not limited thereto:

Formula 300A

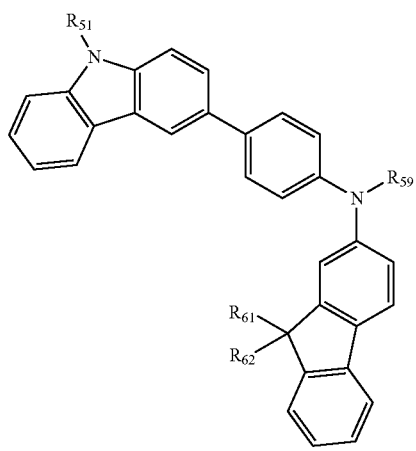

A detailed description of $R_{51}$, $R_{60}$, $R_{61}$, and $R_{59}$ in Formula 300A has already been described above.

For example, at least one layer of the HIL, HTL, and the H-functional layer may include at least one of the following Compounds 301 to 320, but is not limited thereto:

301

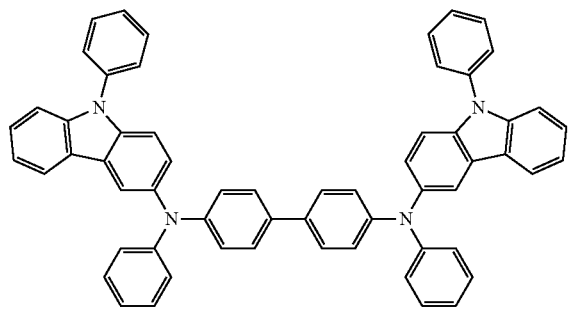

302

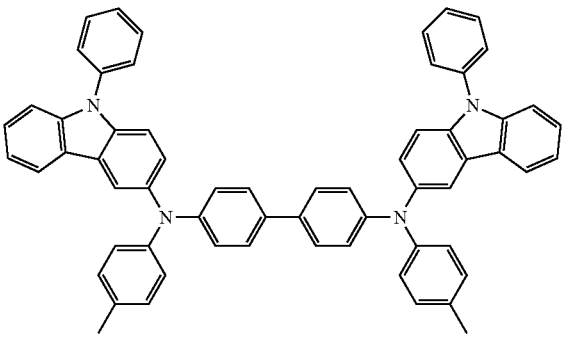

303

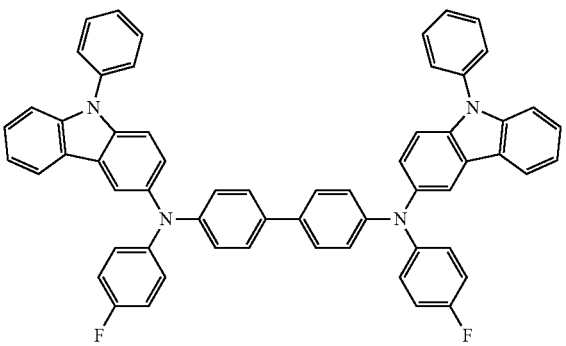

304

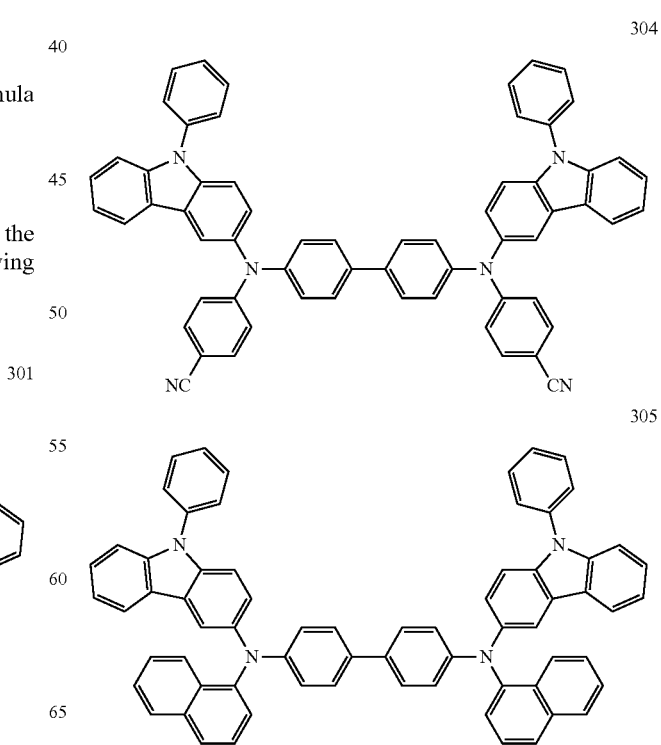

305

306
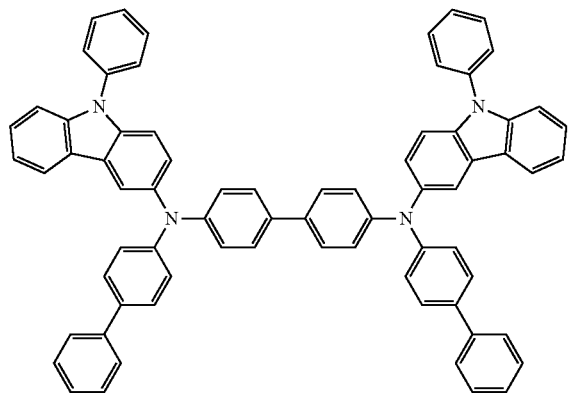
307
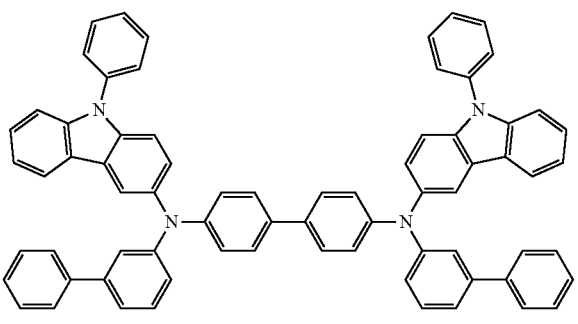
308
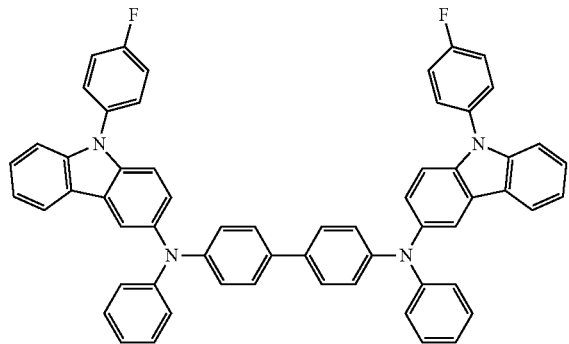
309
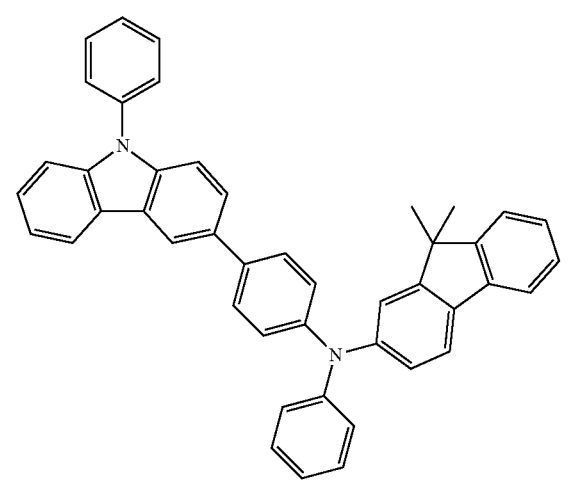
310
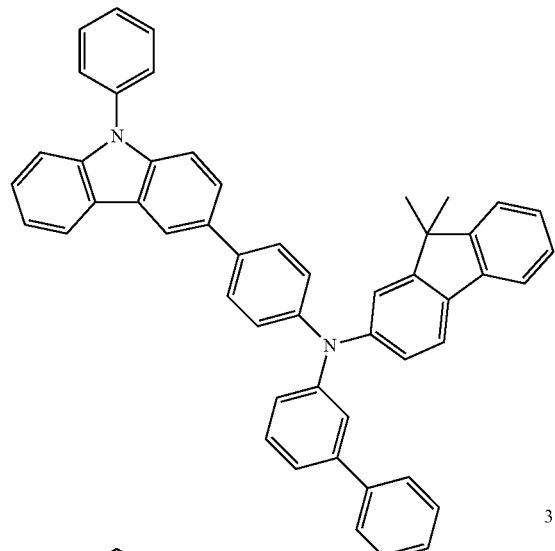
311
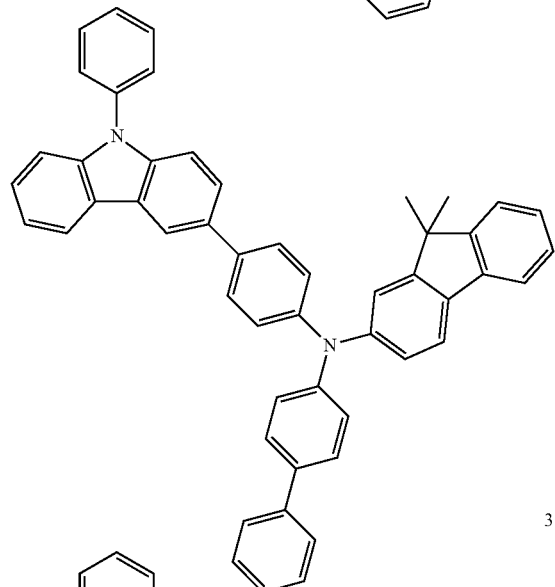
312
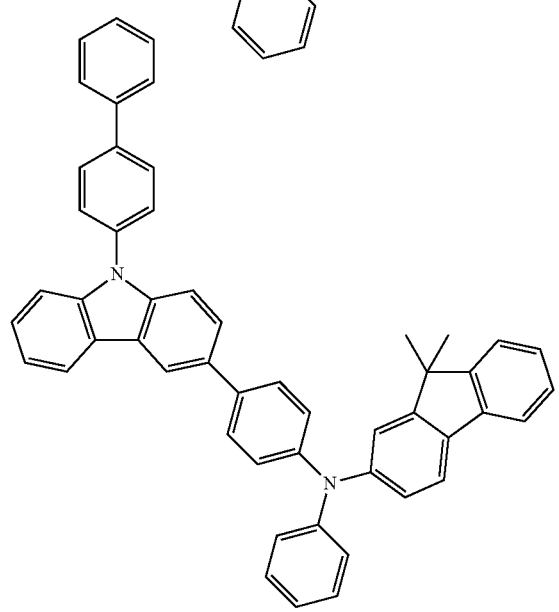

313
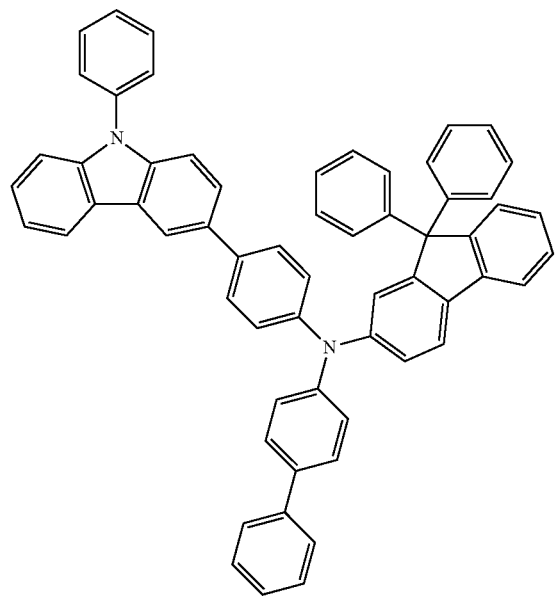
314
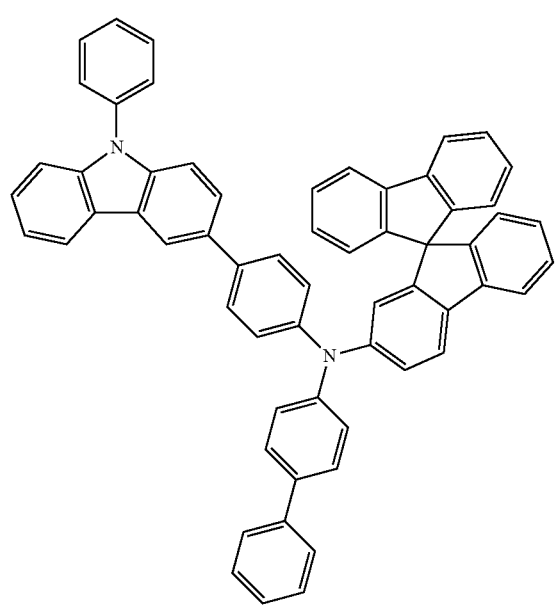
315
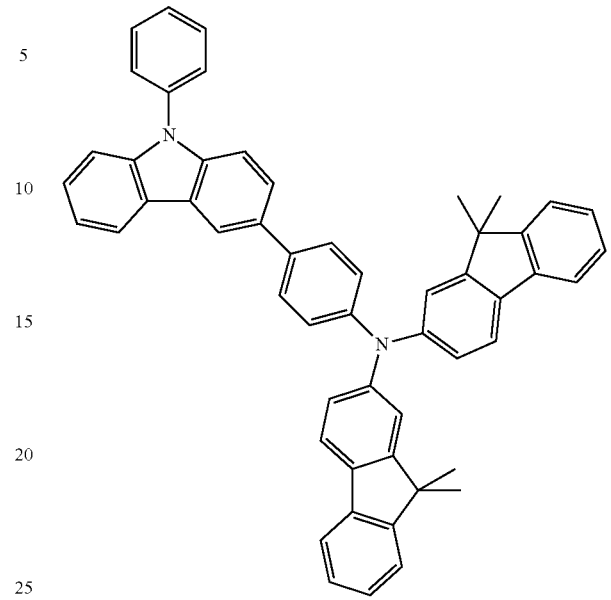
316
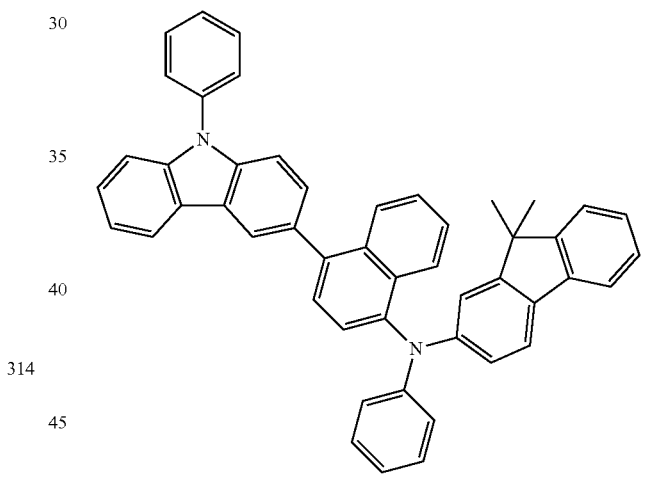
317
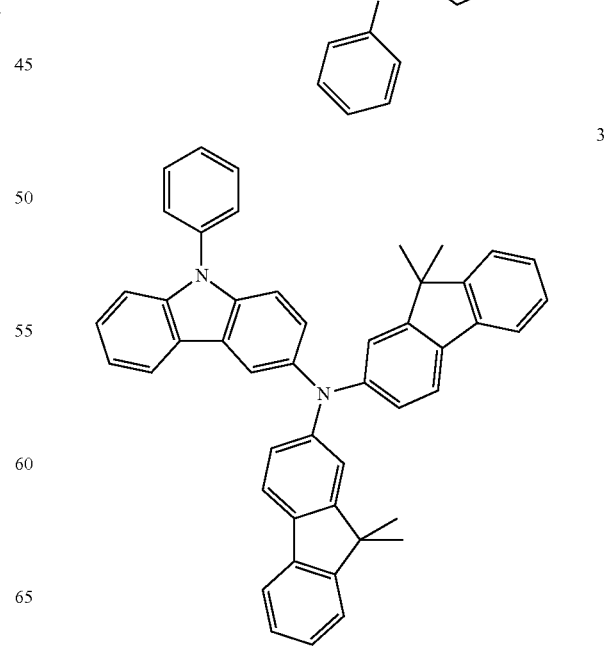

318

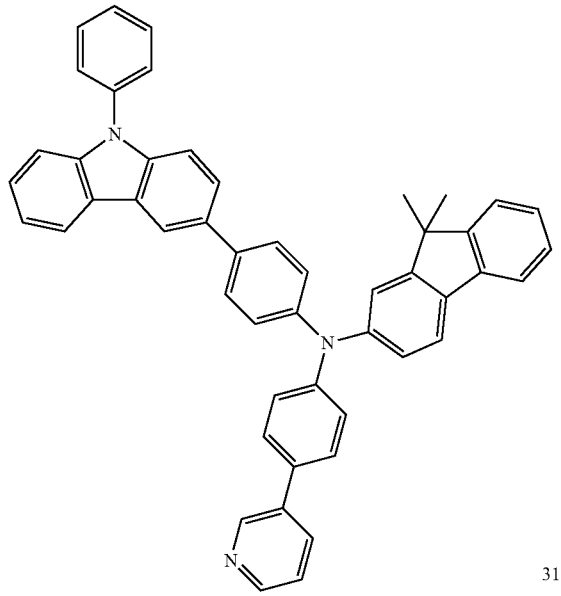

319

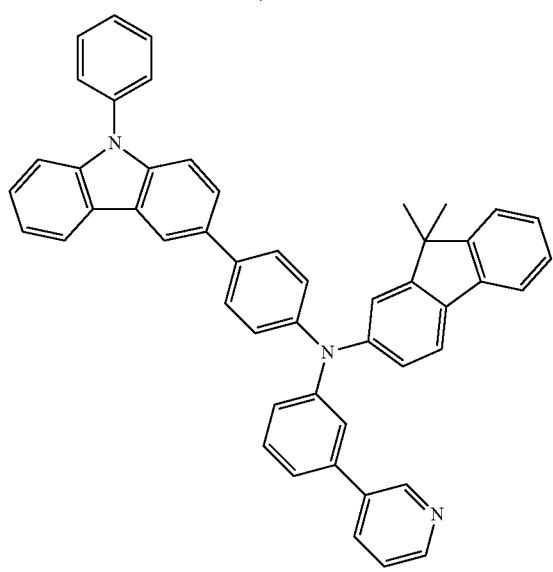

320

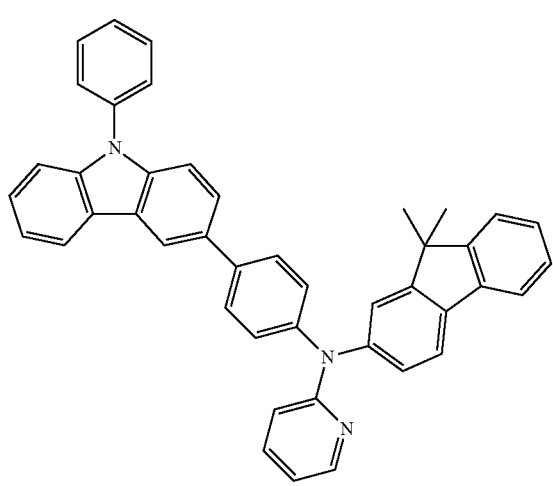

At least one layer of the HIL, HTL, and the H-functional layer may further include a charge-generating material to improve conductivity of a film, in addition to such known hole-injecting materials, known hole-transporting materials, and/or known H-functional materials having both hole injection and hole transport capabilities.

The charge-generating material may be, for example, a p-dopant. The p-dopant may be one of a quinone derivative, a metal oxide, and a compound with a cyano group, but is not limited thereto. Non-limiting examples of the p-dopant are quinone derivatives such as tetracyanoquinodimethane (TCNQ) and 2,3,5,6-tetrafluoro-tetracyano-1,4-benzoquinodimethane(F4-TCNQ); metal oxides such as a tungsten oxide and a molybdenym oxide; and cyano group-containing compounds such as Compound 200 below, but are not limited thereto:

Formula 200

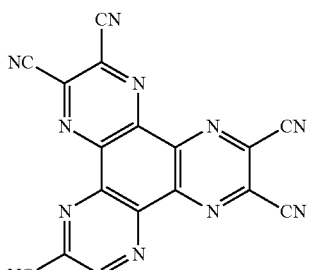

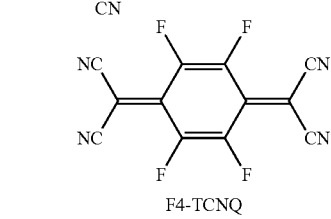

F4-TCNQ

When the HIL, the HTL, or the H-functional layer further includes the charge-generating material, the charge-generating material may be homogeneously dispersed or non-homogeneously distributed in the layers above.

A buffer layer may be disposed between at least one of the HIL, HTL, and the H-functional layer, and the EML. The buffer layer may compensate for an optical resonance distance of light according to a wavelength of the light emitted from the EML, and thus may increase efficiency. The buffer layer may include any hole injecting material or hole transporting material that are widely known. In some other embodiments, the buffer layer may include the same material as one of the materials included in the HIL, the HTL, and the H-functional layer that underlie the buffer layer.

Then, an EML may be formed on the HIL, the H-functional layer, or the buffer layer by vacuum deposition, spin coating, casting, LB deposition, or the like. When the EML is formed using vacuum deposition or spin coating, the deposition and coating conditions may be similar to those for the formation of the HIL, although the conditions for deposition and coating may vary depending on the material that is used to form the EML.

The EML may include the compound of Formula 1 as described above. For example, the compound of Formula 1 may be used as a host or a dopant. In addition to the compound of Formula 1, the EML may be formed using a variety of light-emitting materials that are widely known, for example, a known host and a known dopant. In regard to the dopant, both a known fluorescent dopant and a known phosphorescent dopant may be used Examples of the known host are Alq$_3$, 4,4'-N,N'-dicarbazole-biphenyl (CBP), poly(n-vinylcarbazole) (PVK), 9,10-di(naphthylene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (see Formula below), and Compounds 501 to 509 below, but are not limited thereto.

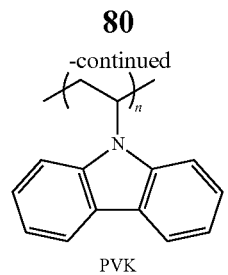

PVK

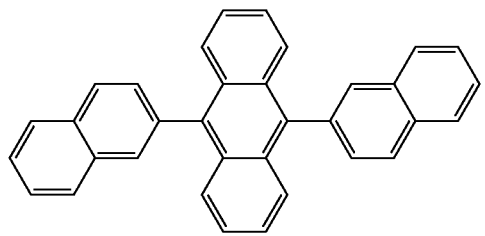

ADN

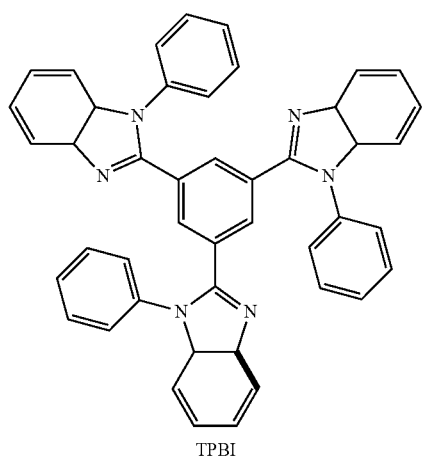

TPBI

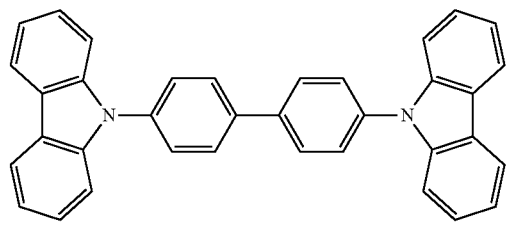

CBP

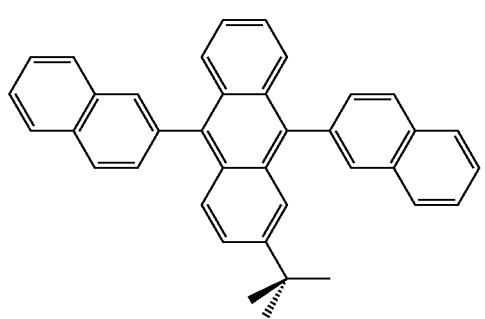

TBADN

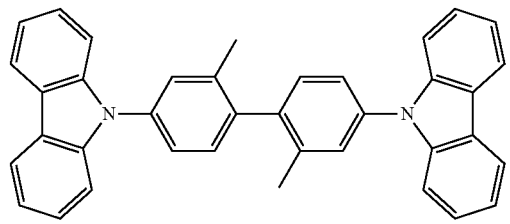

dmCBP

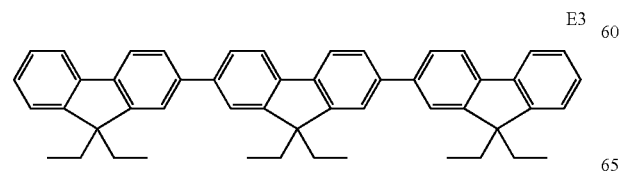

E3

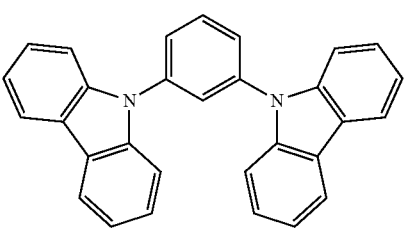

501

-continued
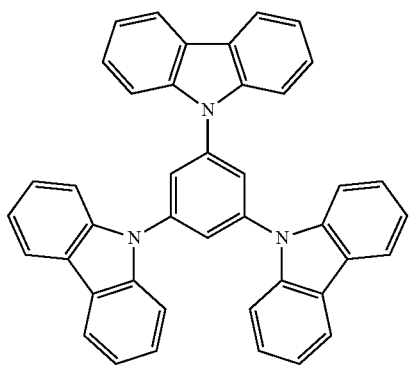
502
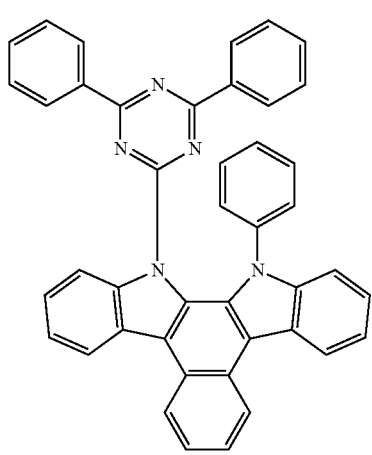
503
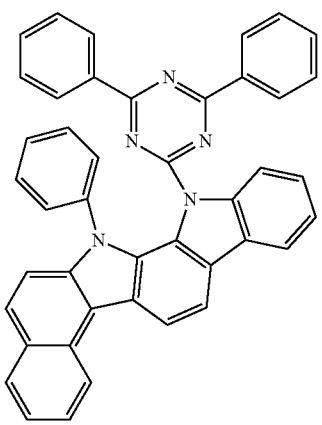
504
-continued
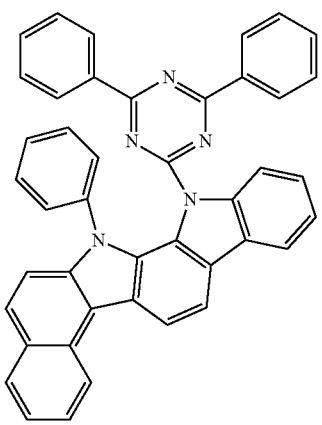
505
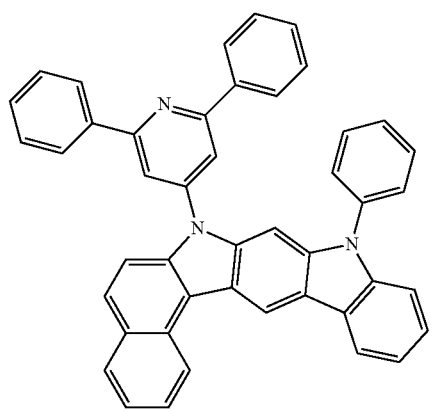
506
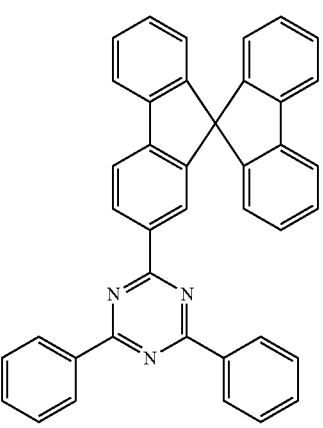
507
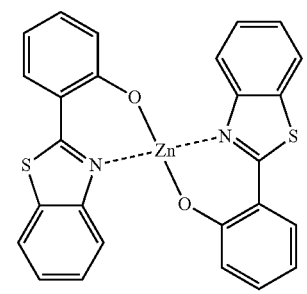
508

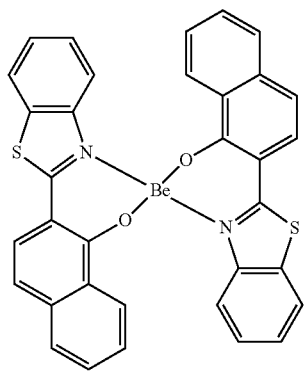

In some embodiments, an anthracene-based compound represented by Formula 400 below may be used as the host:

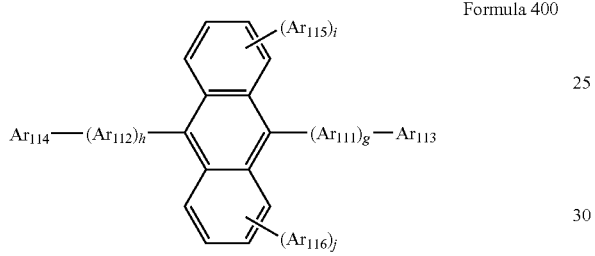

Formula 400 wherein, in Formula 400, $Ar_{111}$ and $Ar_{112}$ may be each independently a substituted or unsubstituted $C_5$-$C_{60}$ arylene group; $Ar_{113}$ to $Ar_{116}$ may be each independently a substituted or unsubstituted $C_1$-$C_{10}$ alkyl group or a substituted or unsubstituted $C_5$-$C_{60}$ aryl group; and g, h, i and j may be each independently an integer from 0 to 4.

For example, $Ar_{111}$ and $Ar_{112}$ in Formula 400 may be each independently selected from a phenylene group, a naphtylene group, a phenanthrenylene group, or a pyrenylene group; or a phenylene group, a naphylene group, a phenanthrenylene group, or a pyrenylene group, each substituted with at least one of a phenyl group, a naphtyl group, and an anthryl group, but is not limited thereto.

g, h, i, and j in Formula 400 may be each independently 0, 1, or 2.

$Ar_{113}$ to $Ar_{116}$ in Formula 400 may be each independently selected from a $C_1$-$C_{10}$ alkyl group substituted with at least one of a phenyl group, a naphtyl group, and an anthryl group;

a phenyl group; a naphtyl group; an anthryl group; a pyrenyl group; a phenanthrenyl group; a fluorenyl group;

a phenyl group, a naphtyl group, an anthryl group, a pyrenyl group, a phenanthrenyl group, and a fluorenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphtyl group, an anthryl group, a pyrenyl group, a phenanthrenyl group, and a fluorenyl group; and

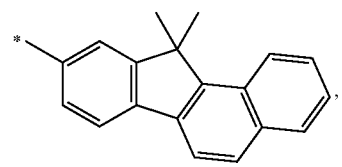

but is not limited thereto.

For example, the anthracene-based compound represented by Formula 400 above may be one of the following compounds represented by Formulas below, but is not limited thereto:

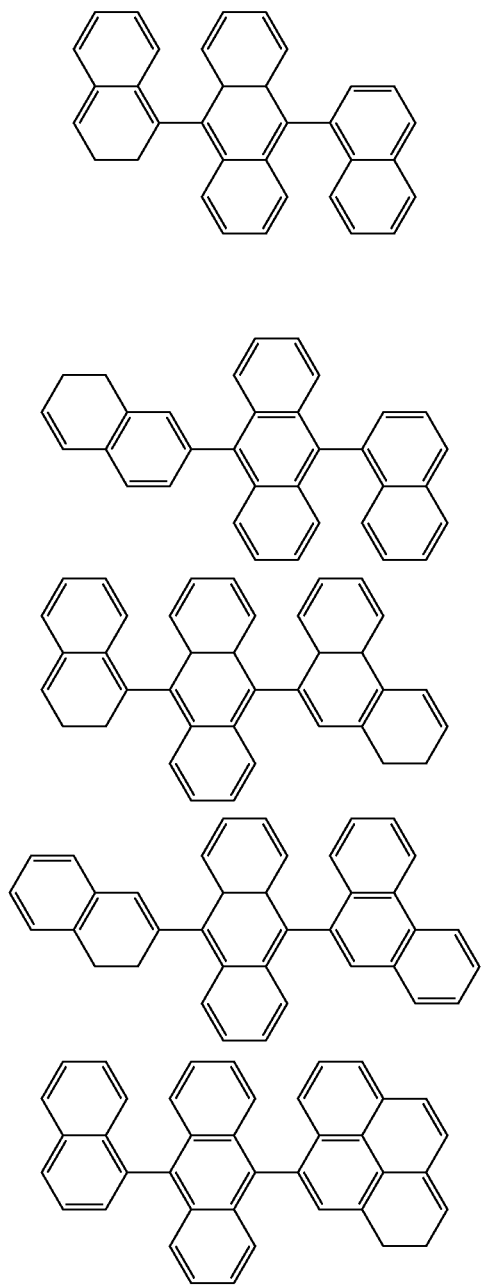

-continued
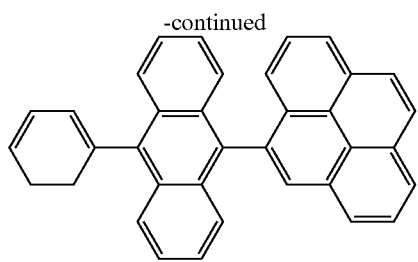 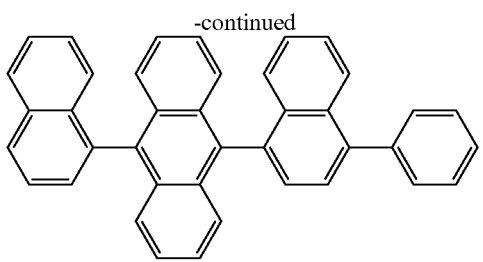
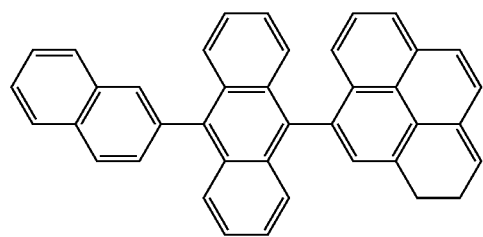 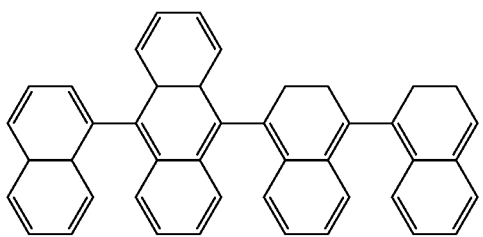
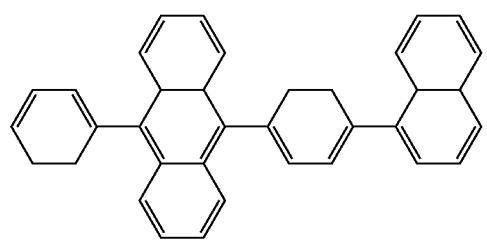 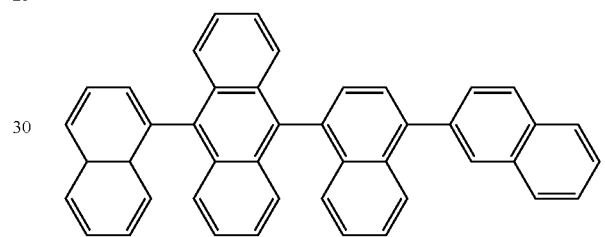
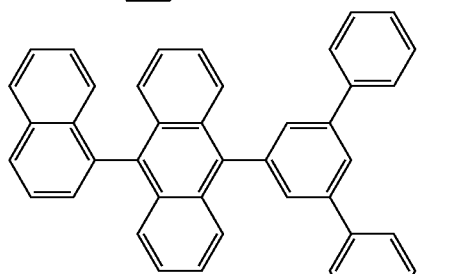 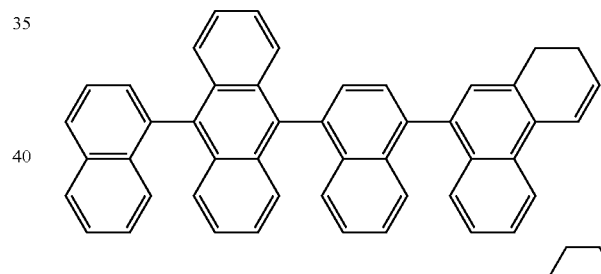
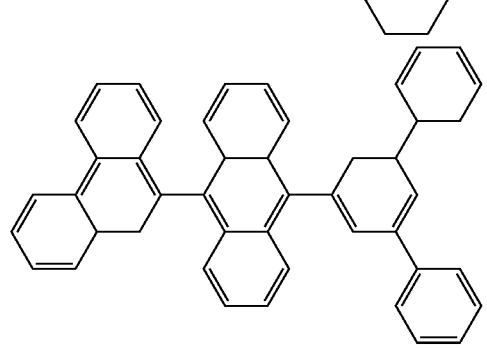 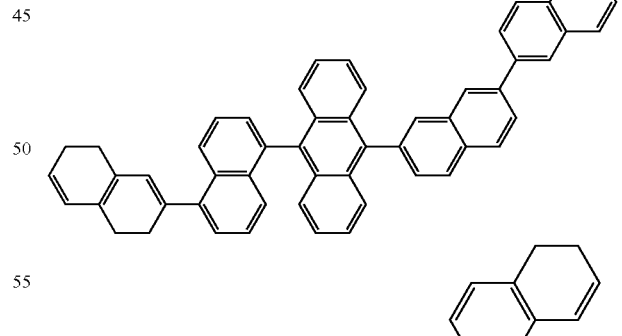
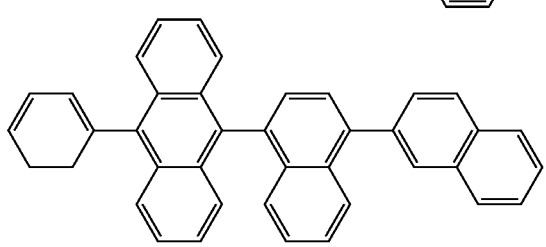 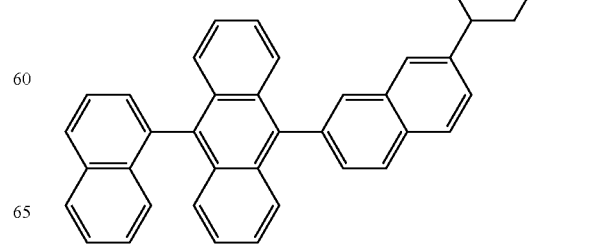

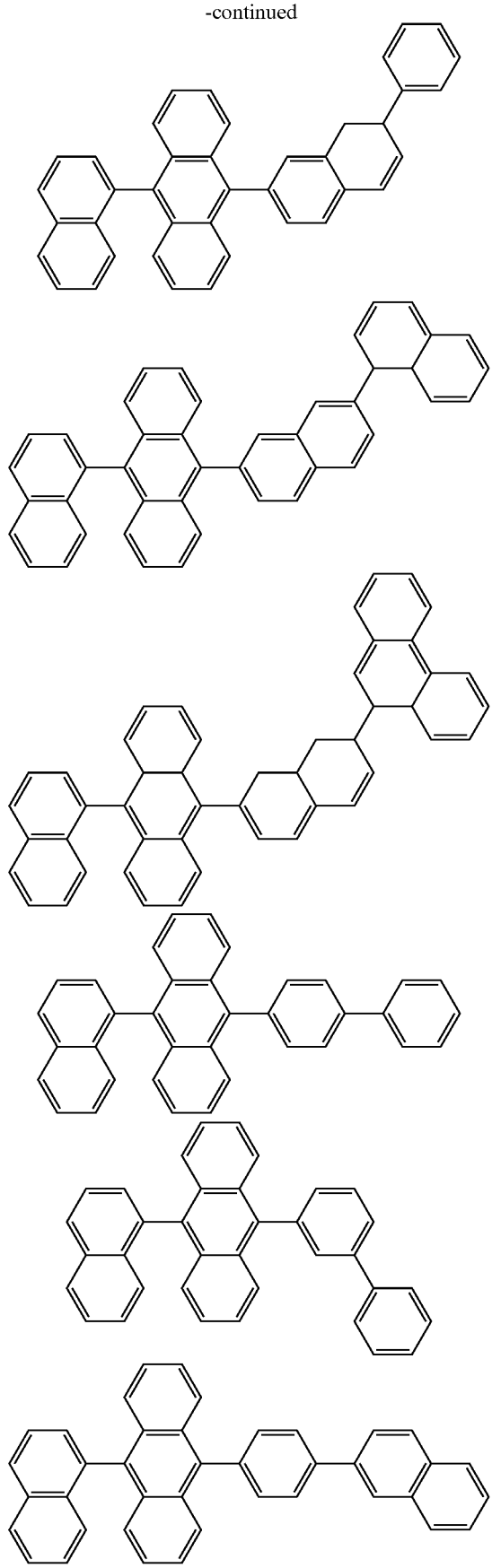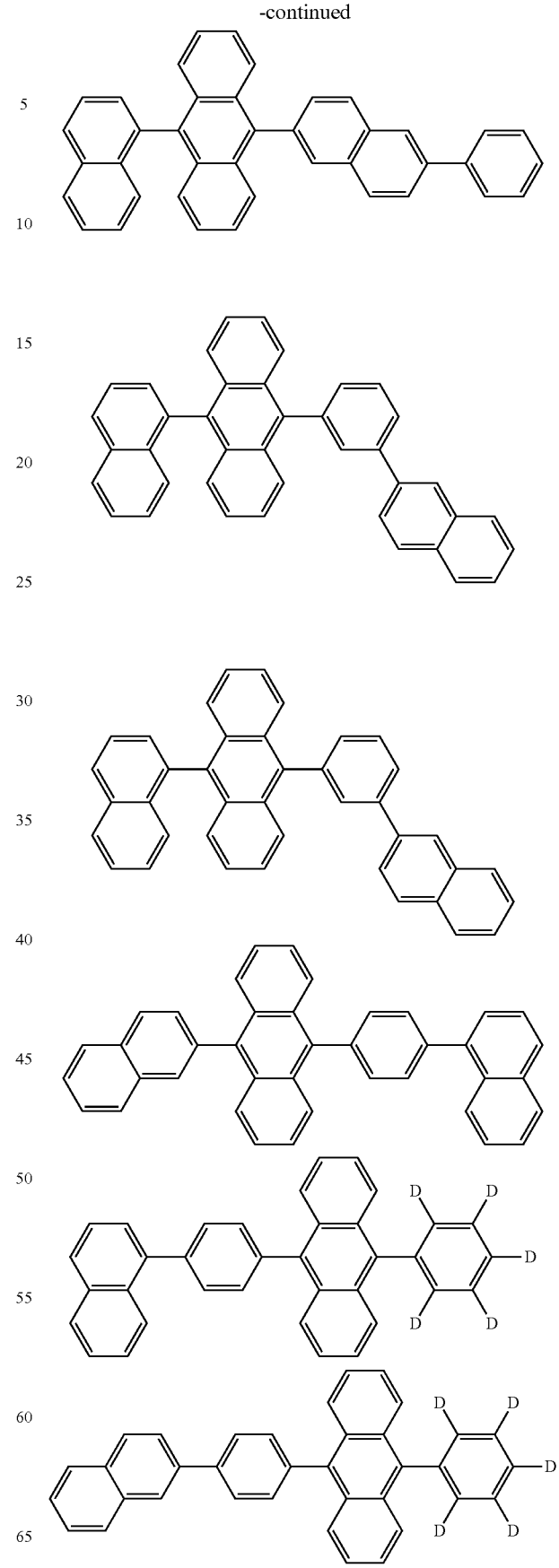

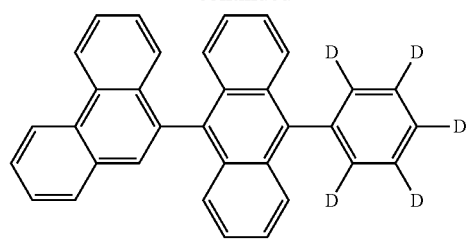

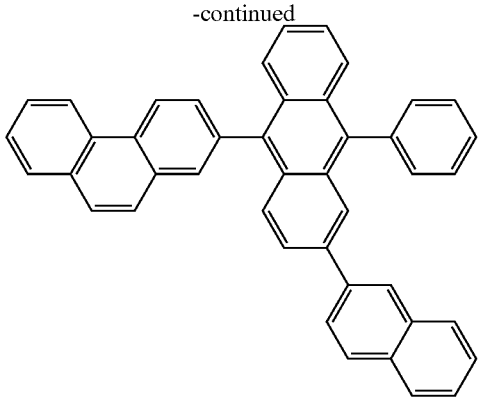

In some embodiments, an anthracene-based compound represented by Formula 401 below may be used as the host:

Formula 401

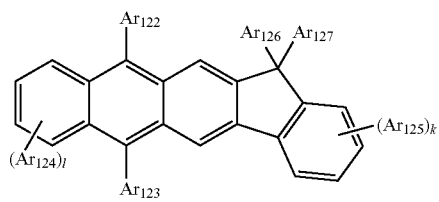

$Ar_{122}$ to $Ar_{125}$ in Formula 401 may be defined as described above with respect to $Ar_{113}$ in Formula 400, and thus detailed descriptions thereof will not be repeated here.

$Ar_{126}$ and $Ar_{127}$ in Formula 401 may be each independently a $C_1$-$C_{10}$ alkyl group (e.g., a methyl group, an ethyl group, or a propyl group).

k and l in Formula 401 may be each independently an integer from 0 to 4. For example, k and l may be 0, 1, or 2.

In some embodiments, the anthracene-based compound represented by Formula 401 may be one of the following compounds represented by Formulas below, but is not limited thereto:

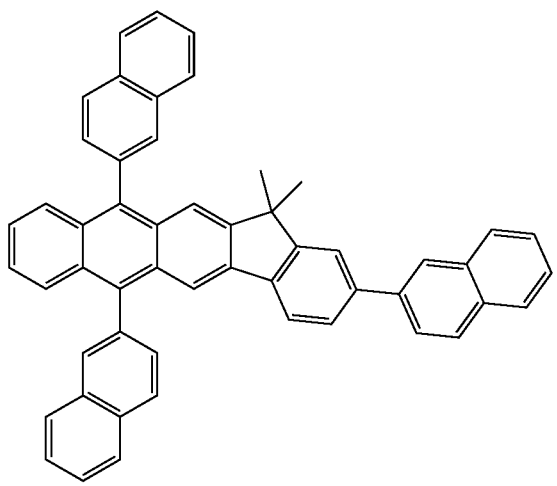

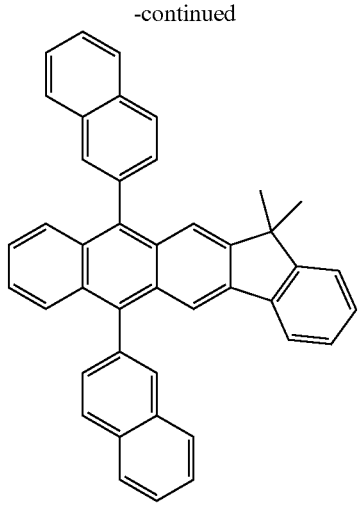

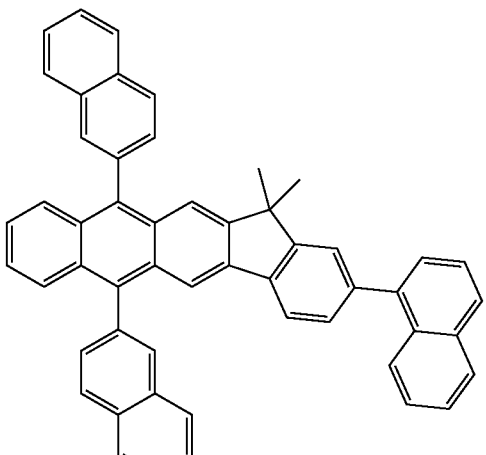

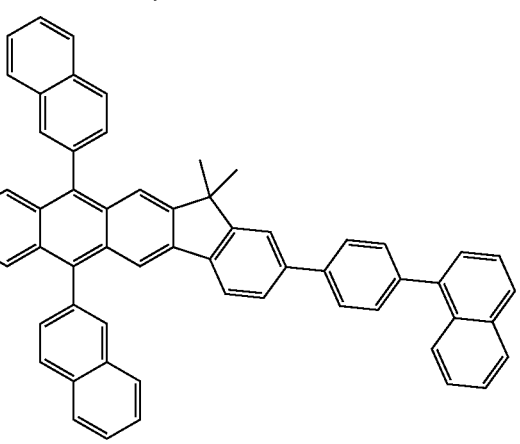

When the OLED is a full color OLED, the EML may be patterned into a red EML, a green EML, and a blue EML. Here, the above-described compound may be included in the blue EML as a blue fluorescent dopant.

At least one the red EML, the green EML, and the blue EML may include one of the following dopants below (ppy=phenylpyridine)

Examples of the blue dopant are the following compounds represented by Formulas below, but are not limited thereto:
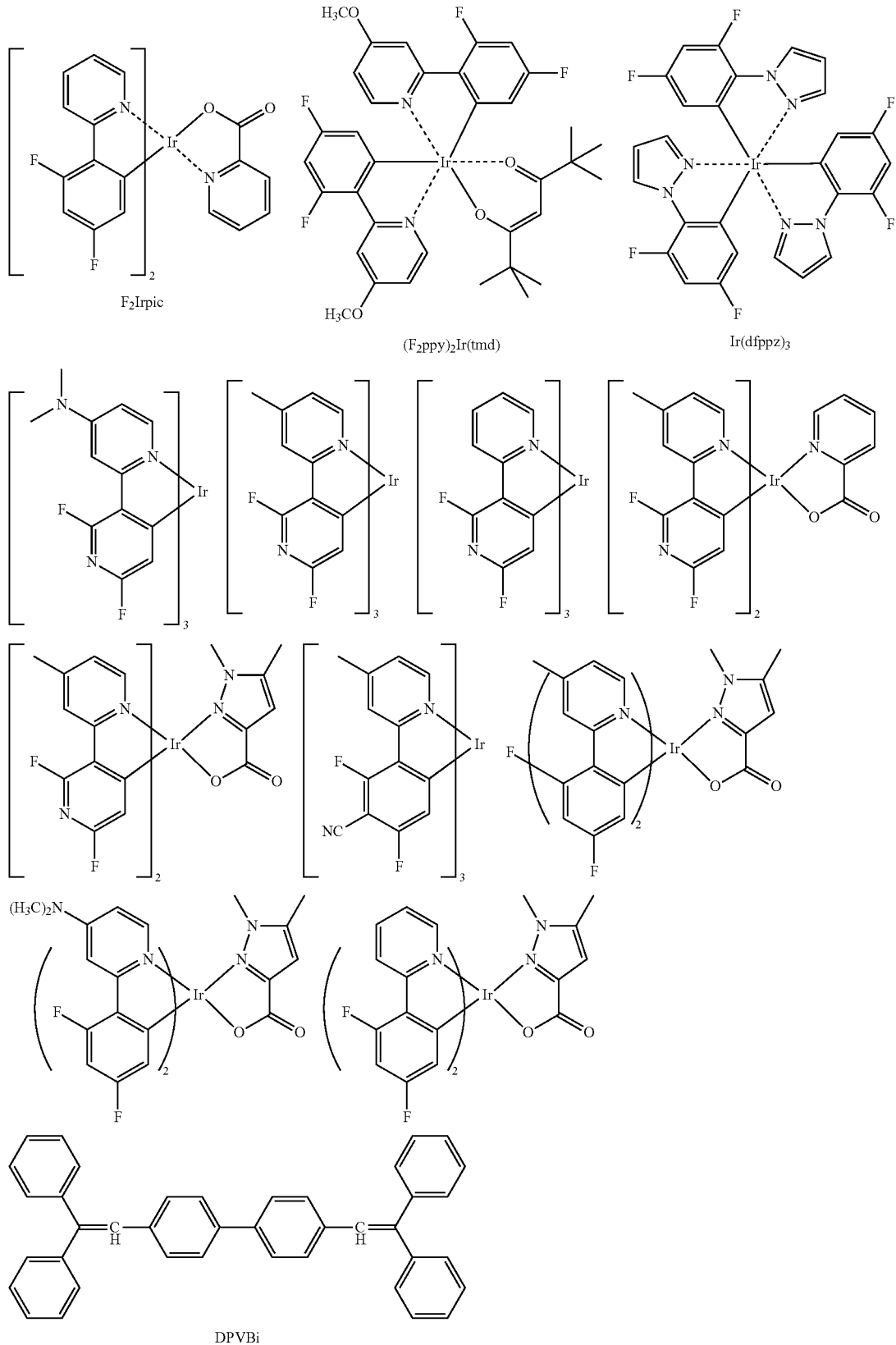

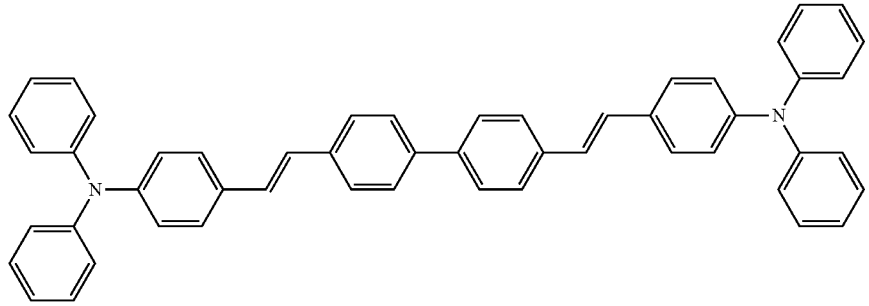
DPAVBi
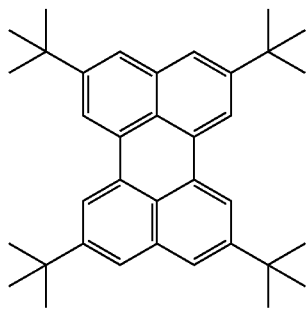
TBPe
Examples of the red dopant are the following compounds represented by Formulas below, but are not limited thereto:
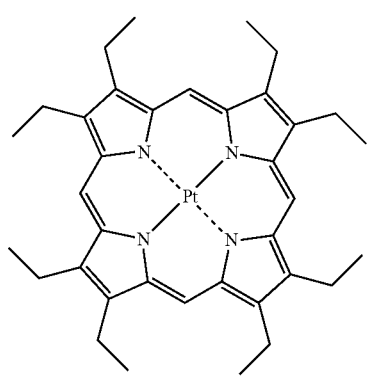
PtOEP
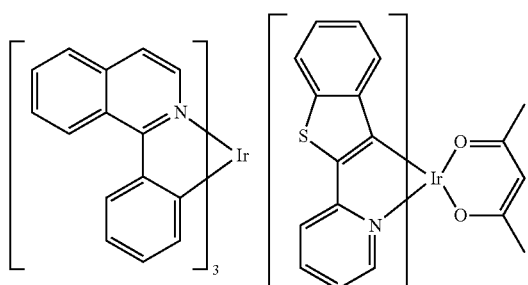
Ir(piq)$_3$    Btp$_2$Ir(acac)
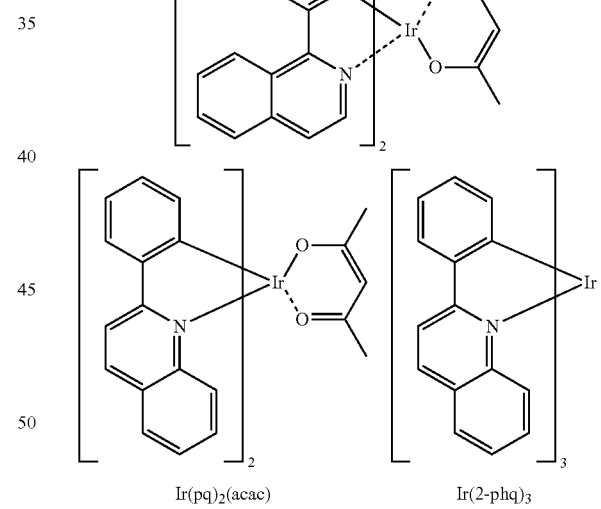
Ir(pq)$_2$(acac)    Ir(2-phq)$_3$
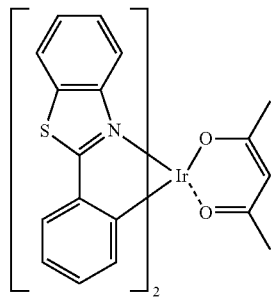
Ir(BT)$_2$(acac)

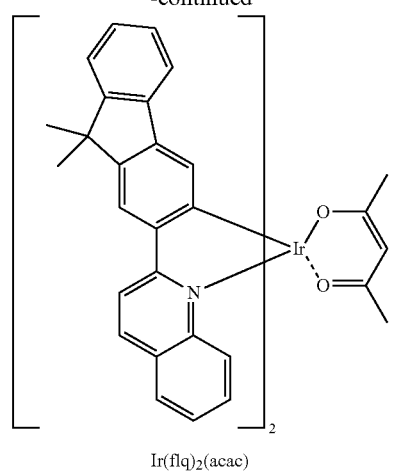
Ir(flq)₂(acac)
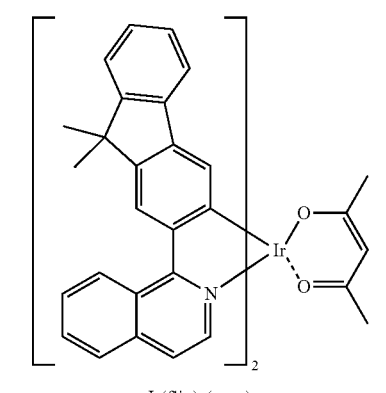
Ir(fliq)₂(acac)
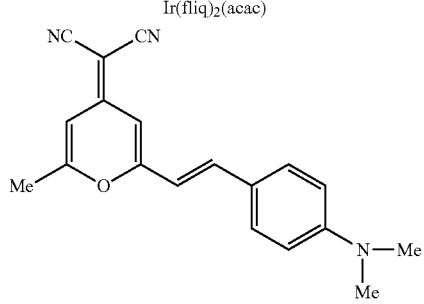
DCM
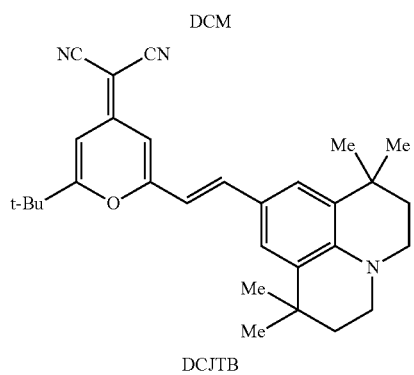
DCJTB
Examples of the green dopant are the following compounds represented by Formulas below, but are not limited thereto:
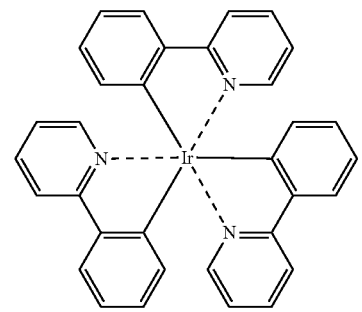
Ir(ppy)₃
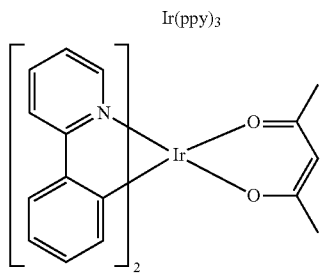
Ir(ppy)₂(acac)
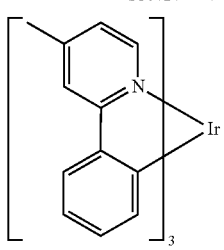
Ir(mpyp)₃
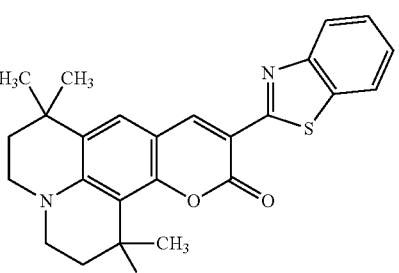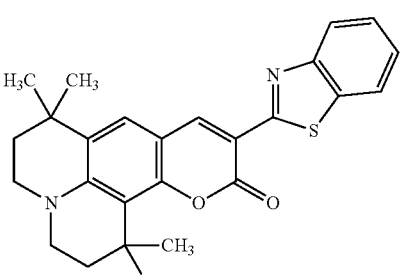
C545T
Examples of dopants that may be used in the EML are Pd complexes or Pt-complexes represented by Formulas below, but are not limited thereto:
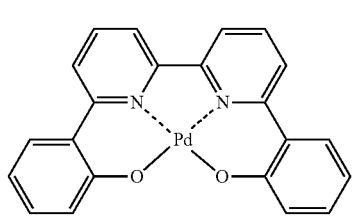
D1

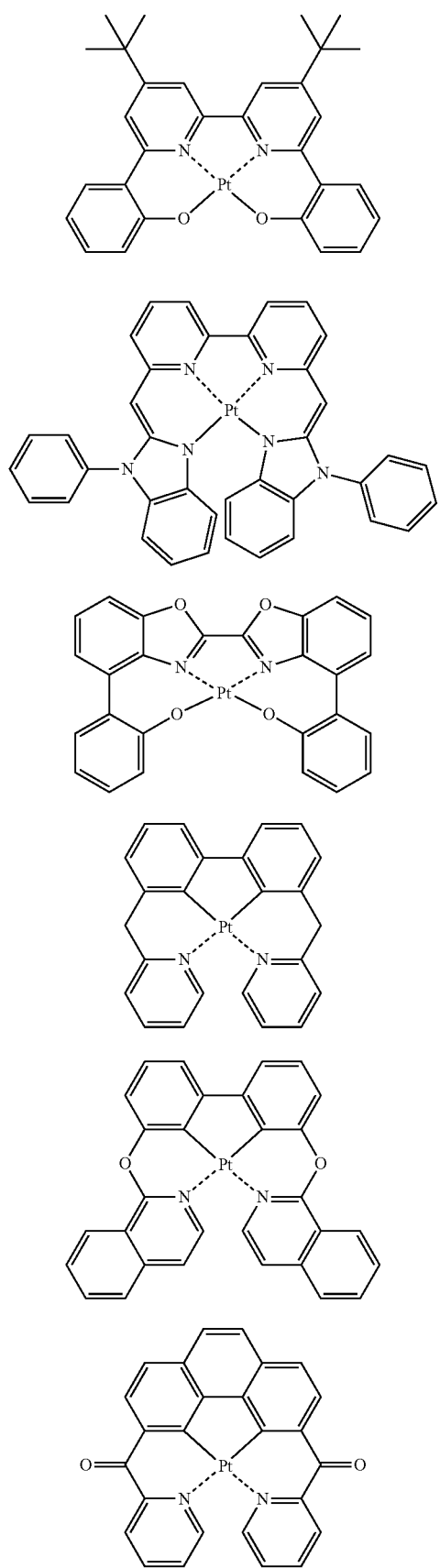

D14
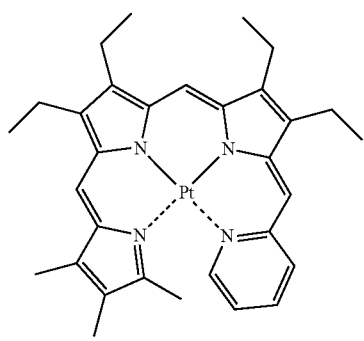
D15
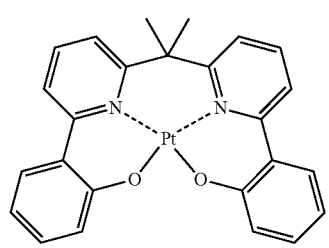
D16
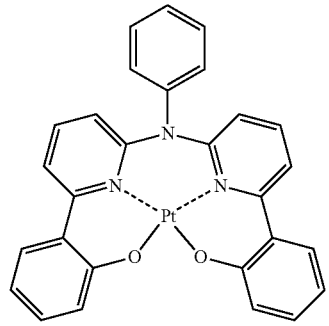
D17
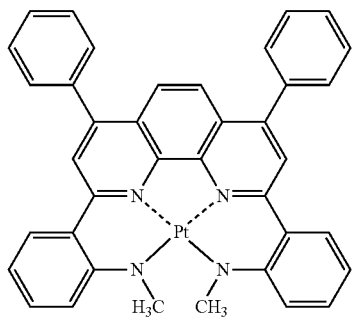
D18
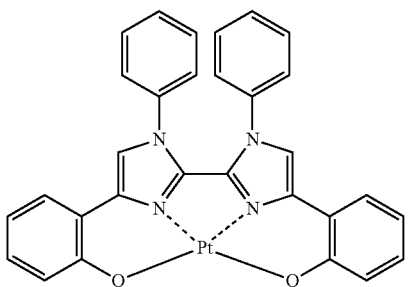
D19
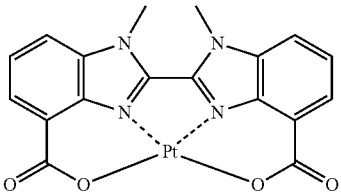
D20
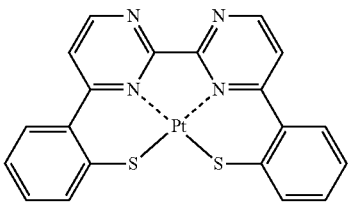
D21
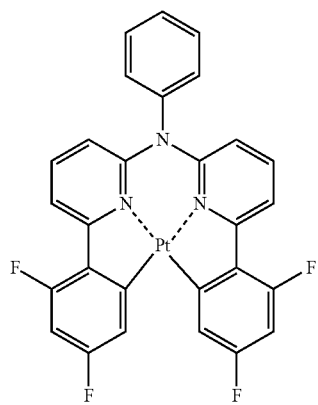
D22
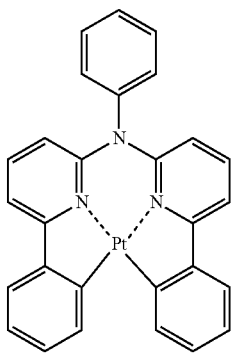
D23
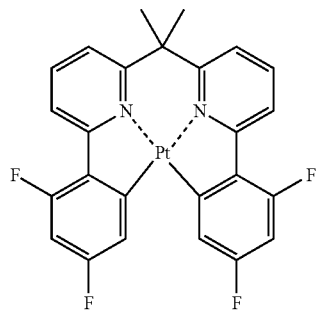

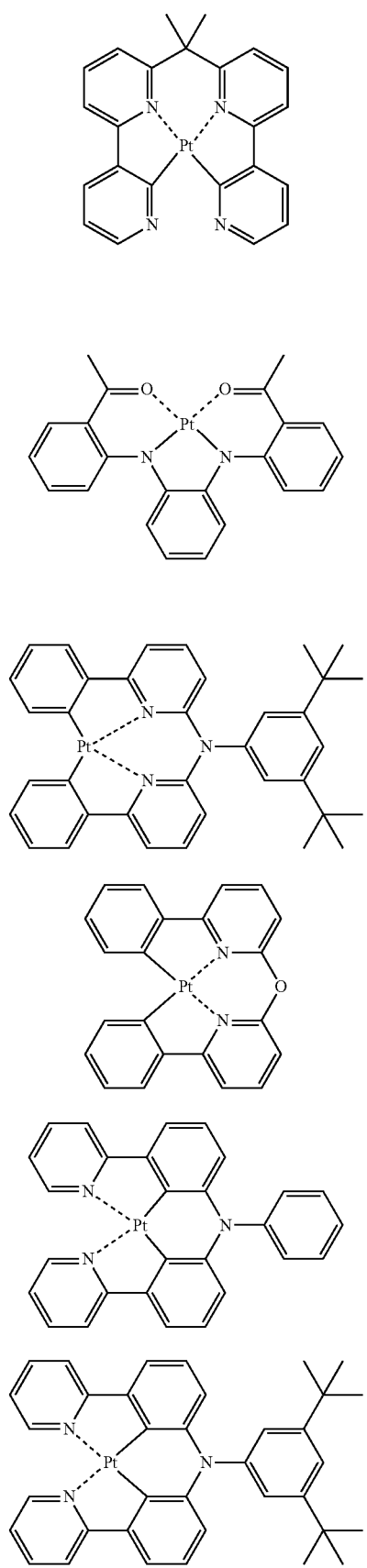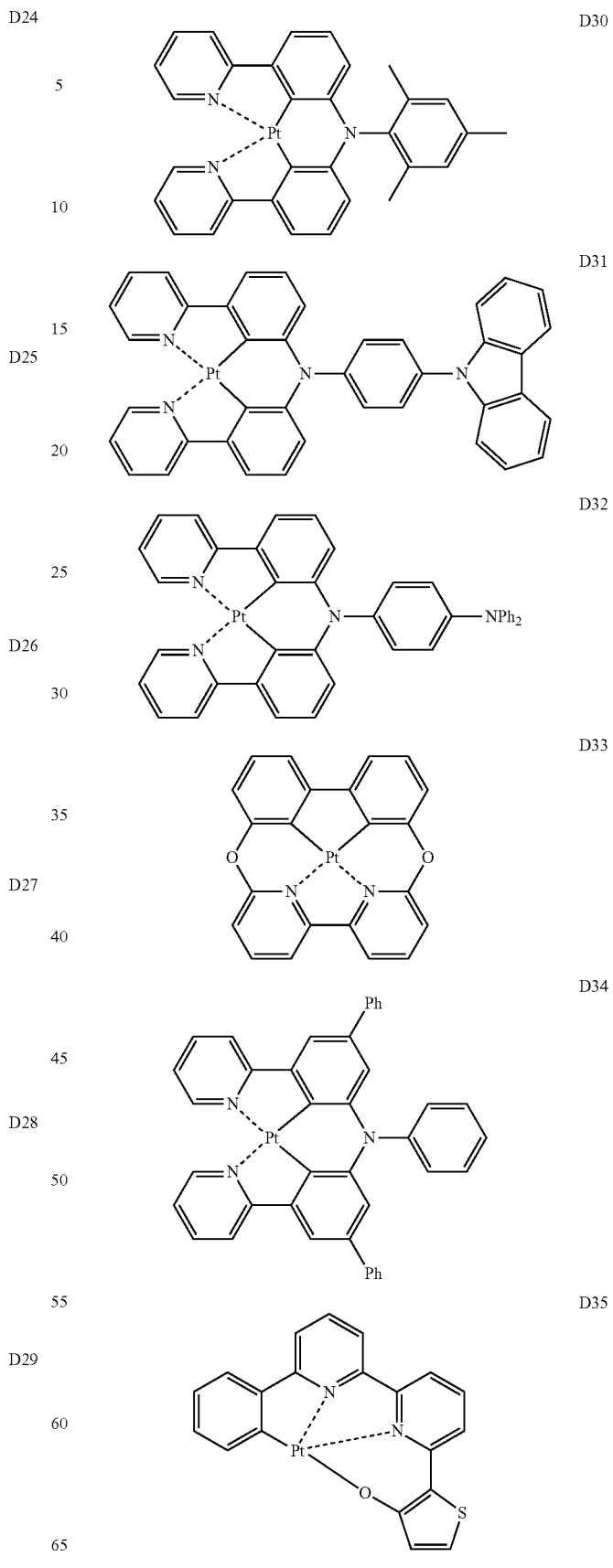

-continued
D36
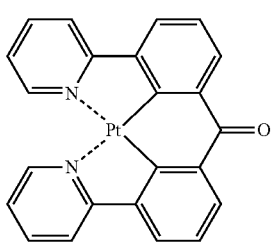
D37
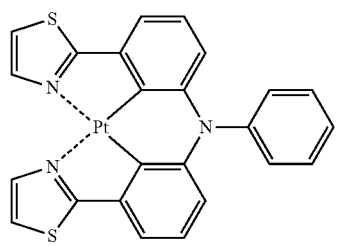
D38
D39
D40
-continued
D41
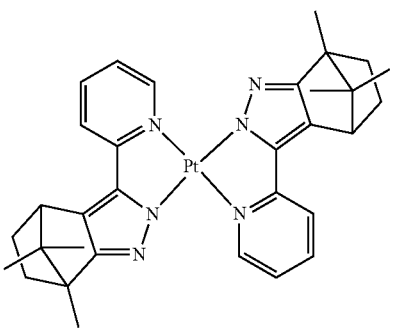
D42
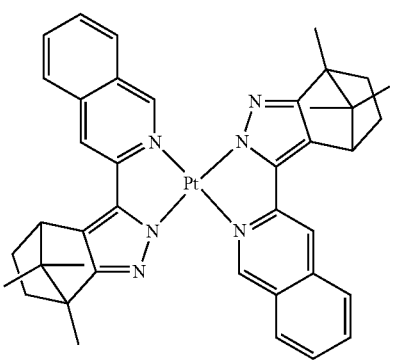
D43
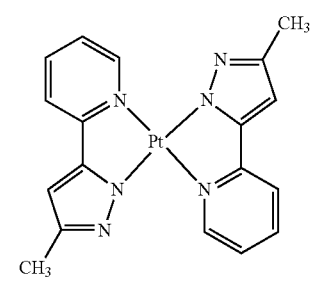
D44
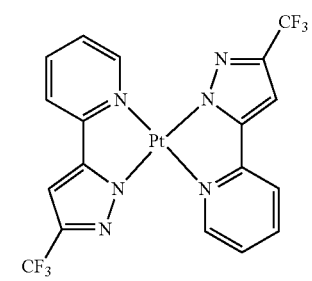
D45
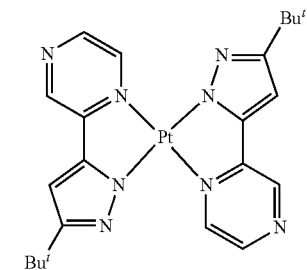

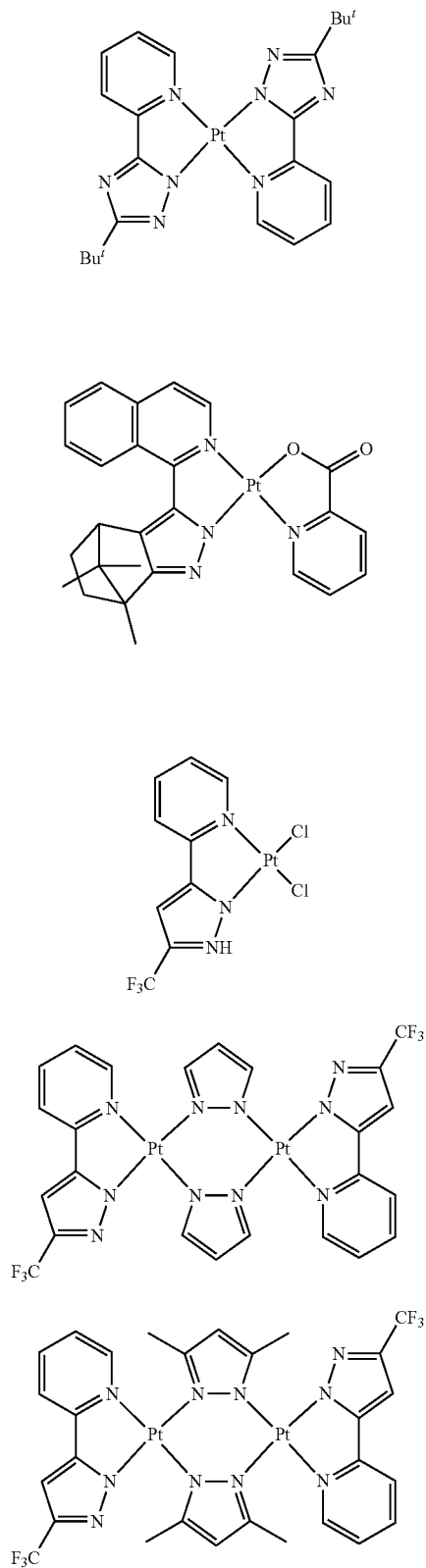
D46
D47
D48
D49
D50
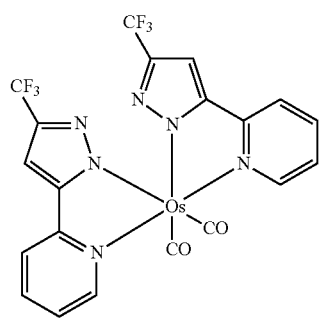
Os(fppz)₂(CO)₂
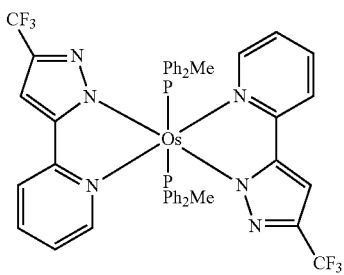
Os(fppz)₂(PPh₂Me)₂
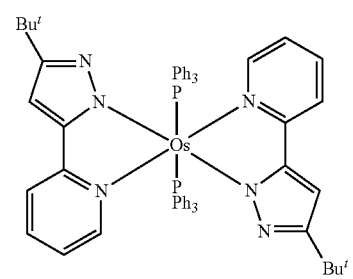
Os(bppz)₂(PPh₃)₂
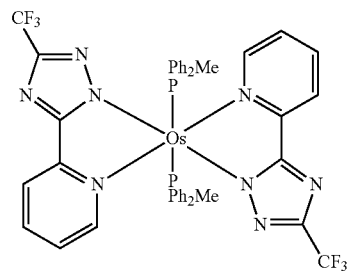
Os(fptz)₂(PPh₂Me)₂
Examples of dopants that may be used in the EML are Os-complexes represented by Formulas below, but are not limited thereto:

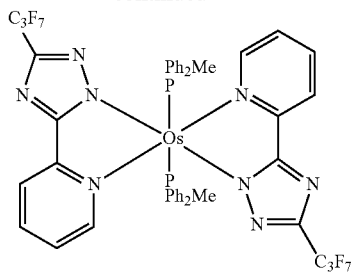

Os(hptz)₂(PPh₂Me)₂

When the EML includes a host and a dopant, an amount of the dopant may be in a range from about 0.01 to about 15 parts by weight based on 100 parts by weight of the host, but is not limited thereto.

A thickness of the EML may be in a range from about 100 Å to about 1,000 Å, for example, from about 200 Å to about 600 Å. When the thickness of the EML is within these ranges, the EML may have good light-emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, although the deposition and coating conditions may vary depending on a compound that is used to form the ETL. A material for forming the ETL may be any known material that can stably transport electrons injected from an electron-injecting electrode (cathode). Examples of the materials for forming the ETL are a quinoline derivative such as tris(8-quinolinorate)aluminum (Alq3), TAZ, BAlq, beryllium bis(benzoquinolin-10-olate) (Bebq₂), 9,10-di (naphthalene-2-yl)anthracene ADN, Compound 201, and Compound 202, but are not limited thereto:

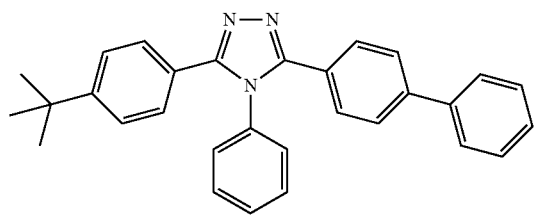

TAZ

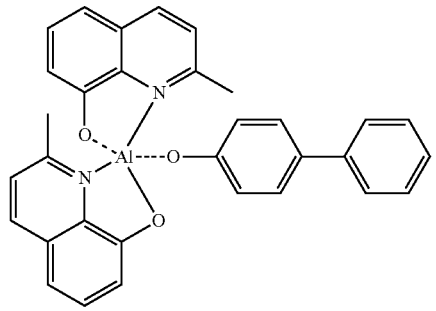

BAlq

<Compound 201>

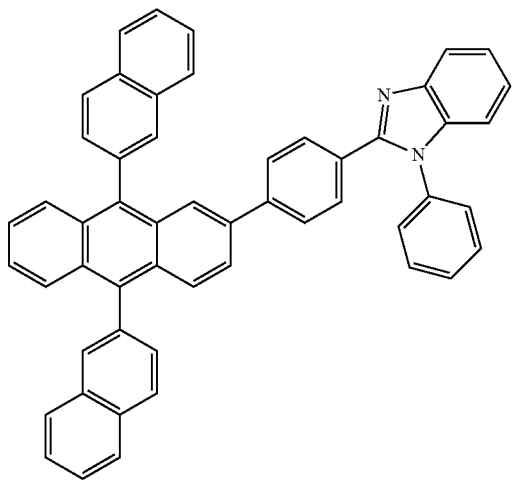

<Compound 202>

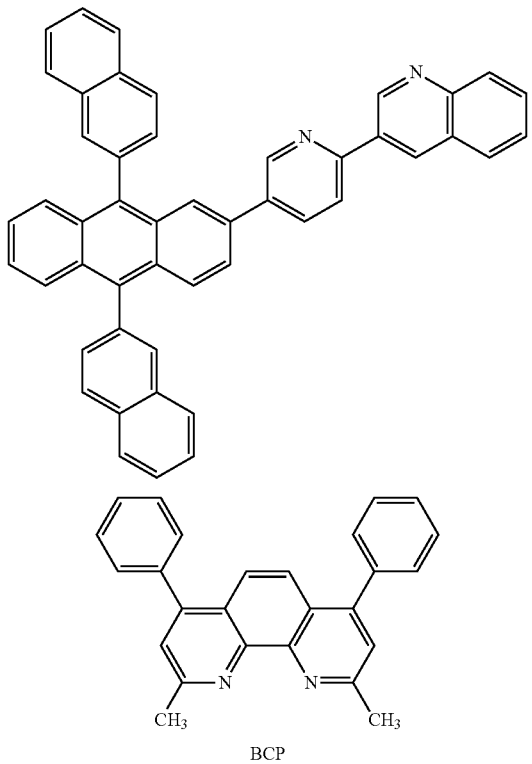

BCP

A thickness of the ETL may be in a range from about 100 Å to about 1,000 Å, for example, from about 150 Å to about 500 Å. When the thickness of the ETL is within these ranges, the ETL may have a satisfactory electron transporting ability without a substantial increase in driving voltage.

In some embodiments, the ETL may further include a metal-containing material, in addition to any known electron transporting organic compound.

The metal-containing material may include a lithium (Li) complex. Non-limiting examples of the Li complex are lithium quinolate (LiQ) and Compound 203 below:

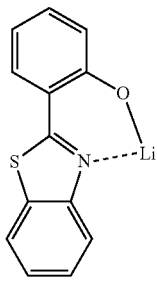

Compound 203

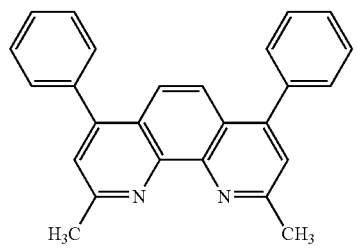

BCP

Then, an EIL, which facilitates injection of electrons from the cathode, may be formed on the ETL. Any suitable electron-injecting material may be used to form the EIL.

Examples of materials for forming the EIL are LiF, NaCl, CsF, Li$_2$O, and BaO, which are known in the art. Deposition conditions of the EIL may be similar to those for the formation of the HIL, although the conditions may vary depending on a material that is used to form the EIL.

A thickness of the EIL may be in a range from about 1 Å to about 100 Å, for example, from about 3 Å to about 90 Å. When the thickness of the EIL is within these ranges, the EIL may have satisfactory electron injection ability without a substantial increase in driving voltage.

A second electrode is disposed on the organic layer. The second electrode may be a cathode that is an electron injection electrode. Here, material for forming the second electrode may be a metal, an alloy, and an electro-conductive compound, which have a low work function, or a mixture thereof. In this regard, the second electrode may comprise lithium (Li), magnesium (Mg), aluminum (Al), aluminum-lithium (Al—Li), calcium (Ca), magnesium-indium (Mg—In), magnesium-silver (Mg—Ag), or the like, and may be formed as a thin film type transmission electrode. In some embodiments, to manufacture a top-emission light-emitting diode, the transmission electrode may comprise indium tin oxide (ITO) or indium zinc oxide (IZO).

An OLED according to an embodiment has already been described above with reference to FIG. 1, but is not limited to the structure illustrated in FIG. 1.

In addition, when the EML is formed using a phosphorescent dopant, to prevent diffusion of triplet excitons or holes toward the ETL, a hole blocking layer (HBL) may be formed between the HTL and the EML or between the H-functional layer and the EML by a method such as, for example, vacuum deposition, spin coating, casting, LB, or the like. When the HBL is formed using vacuum deposition or spin coating, the deposition and coating conditions may be similar to those for the formation of the HIL, although the conditions for deposition and coating may vary depending on the material that is used to form the HBL. Any known hole-blocking material may be used. Non-limiting examples of hole-blocking materials are oxadiazole derivatives, triazole derivatives, and phenanthroline derivatives. For example, BCP illustrated below may be used as a material for the HBL.

A thickness of the HBL may be in a range from about 20 Å to about 1000 Å, for example, from about 30 Å to about 300 Å. When the thickness of the HBL is within these ranges, the HBL may have an improved hole blocking ability without a substantial increase in driving voltage.

The OLED according to an embodiment may be provided in various types of flat panel display devices such as passive matrix OLED devices and active matrix OLED devices. In particular, when the OLED is provided in an active matrix OLED, the first electrode on the substrate, which acts as a pixel electrode, may be electrically connected to a source electrode or a drain electrode of a thin-film transistor (TFT). In addition, the OLED may be provided in a flat panel display device having double-sided screens.

In some embodiments the organic layer of the organic light-emitting device may comprise the compound of Formula 1 by using a deposition method or may be formed using a wet process of coating a solution of the compound of Formula 1.

Hereinafter, the present embodiments will be described in detail with reference to the following synthesis examples and other examples. However, these examples are for illustrative purposes only and are not intended to limit the scope of the present embodiments.

EXAMPLE

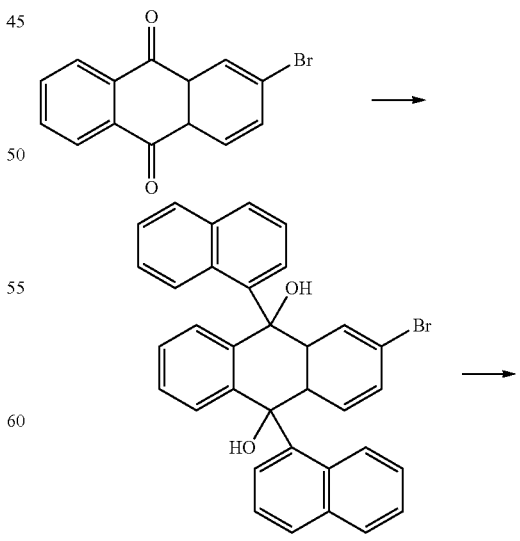

1a

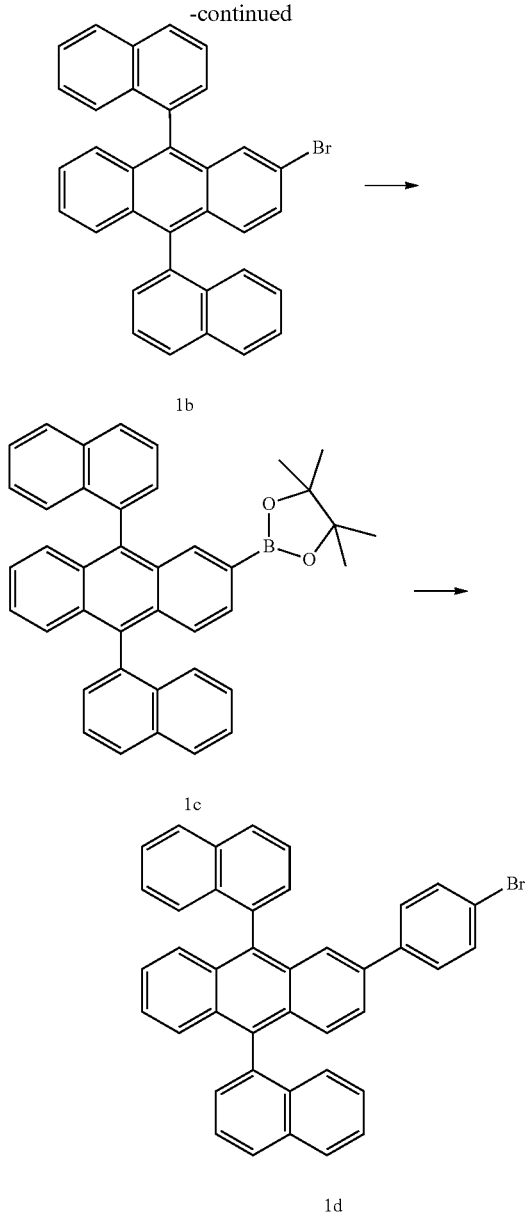

1b

1c

1d

Synthesis Example of Intermediate 1d

1) Synthesis of Intermediate 1a 10.3 g (50.0 mmol) of 1-bromonaphthalene was dissolved in 100 mL of tetrahydrofuran (THF), and 29.4 mL of t-BuLi 29.4 (1.7 M in pentane) was slowly added thereto, and then stirred at a temperature of about −78° C. for about 2 hours. Next, 6.10 g (21.0 mmol) of 2-bromo-4-a,9a-dihydro-anthraquinone was slowly added thereto and stirred at room temperature for about 5 hours. Then, ammonium chloride aqueous solution was added thereto, and the reaction solution was extracted with methylene chloride. An organic layer was collected and was dried using magnesium sulfate. After dissolving the mixture obtained therefrom in a small amount of ethyl ether, petroleum ether was added thereto and then stirred for several hours to obtain a solid compound. The solid compound was filtered, and then was vacuum dried to obtain 10.5 g of Intermediate 1a (Yield: 92%). The obtained compound was identified by $^1$H NMR and MS/FAB ($C_{34}H_{25}BrO_2$: calc. 544.10. found 544.12).

$^1$H NMR (CDCl$_3$, 400 MHz) δ 8.47 (d, 1H), 8.36 (d, 1H), 7.86-7.74 (m, 4H), 7.64-7.42 (m, 9H), 7.27-7.25 (m), 7.12-7.10 (m) (3H), 7.02 (s, 1H), 6.78 (d, 1H), 6.59 (m, 1H), 5.83-5.75 (m, 2H), 2.22 (s, 2H)

2) Synthesis of Intermediate 1b

After dissolving 10.5 g (19.3 mmol) of Intermediate 1a, 32.0 g (193 mmol) of KI, and 34.0 g (386 mmol) of NaH$_2$PO$_2$.H$_2$O in 200 mL of acetic acid, the reaction solution was stirred at a temperature of about 110° C. for about 5 hours. The reaction solution was cooled to room temperature, filtered and washed with water and methanol, and dried to obtain 6.7 g (Yield: 68%) of Intermediate 1b. The obtained compound was identified by $^1$H NMR and MS/FAB ($C_{34}H_{21}Br$: calc. 508.08. found 508.07).

$^1$H NMR (CDCl$_3$, 400 MHz) δ 8.38 (d, 1H), 7.85-7.79 (m, 4H), 7.73-7.69 (m, 4H), 7.60-7.45 (m, 6H), 7.37-7.30 (m, 4H), 7.18 (t, 2H)

3) Synthesis of Intermediate 1c 6.7 g (13.1 mmol) of Intermediate 1b, 3.65 g (14.4 mmol) of bis-(pinacolato)diboron, 3.86 g (39.3 mmol) of KOAc, and 0.32 g (0.39 mmol) of palladium(diphenyl phosphino-ferrocene)chloride was added in 250 mL flask, and then dissolved in 70 mL of dioxane, and heated under reflux at a temperature of about 80° C. for about 6 hours. After the reaction solution was cooled to room temperature, 50 mL of distilled water was added thereto, and extracted with methylene chloride (50 mL×3). An organic layer was collected and dried using magnesium sulfate, and the residual obtained by evaporating the solvent was washed with ethanol and dried to obtain 6.24 g of Intermediate 1c (Yield: 88%). The obtained compound was identified by $^1$H NMR and MS/FAB ($C_{40}H_{33}BO_2$: calc. 541.23. found 541.21).

$^1$H NMR (CDCl$_3$, 400 MHz) δ 8.76 (d, 1H), 8.59 (d, 1H), 8.38 (d, 1H), 7.87-7.82 (m, 4H), 7.77 (d, 1H), 7.72-7.68 (m, 5H), 7.58 (d, 1H), 7.45 (d, 1H), 7.37-7.31 (m, 4H), 7.15 t, 2H), 1.32 (s, 6H), 1.29 (s, 6H)

4) Intermediate of Intermediate 1d 5.96 g (11.0 mmol) of Intermediate 1c, 2.60 g (20.2 mmol) of 1,4-dibromobenzene, 0.64 g (0.55 mmol) of Pd(PPh$_3$)$_4$, and 4.56 g (33.0 mmol) of K$_2$CO$_3$ was dissolved in 60 mL of THF and 30 mL of H$_2$O, and was stirred at a temperature of about 80° C. for about 12 hours. The reaction solution was cooled to room temperature, and then, was extracted three times with 30 mL of water and 30 mL of ethyl acetate. An organic layer obtained therefrom was dried with magnesium sulfate and a solvent was evaporated and the residual was separation-purified by silicagel column chromatography to obtain 4.64 g (Yield: 72%) of Intermediate 1d. The obtained compound was identified by $^1$H NMR and MS/FAB ($C_{40}H_{25}Br$: calc. 584.11. found 584.12).

¹H NMR (CDCl₃, 400 MHz) δ 8.38 (d, 1H), 8.16 (d, 1H), 8.01 (d, 1H), 7.86-7.82 (m, 5H), 7.75-7.72 (m, 4H), 7.67-7.59 (m, 5H), 7.51 (d, 1H), 7.45 (d, 1H), 7.37-7.30 (m, 4H), 7.16 (t, 2H)

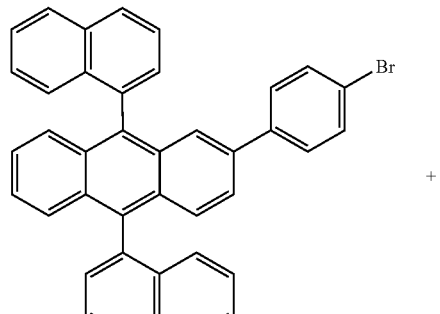

1d

+

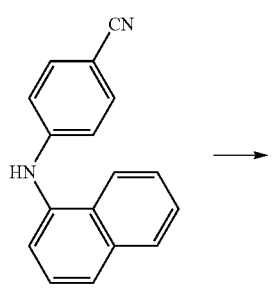

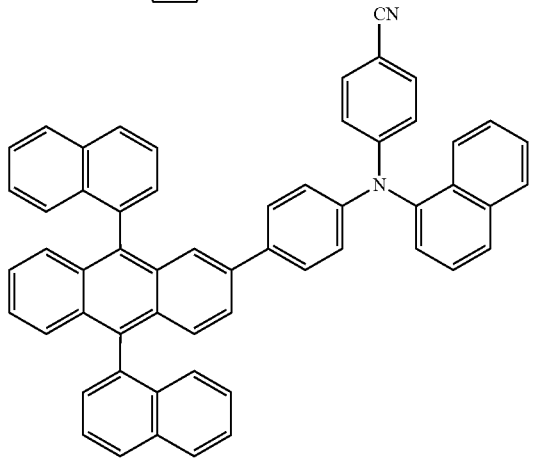

화합물 7

Synthesis of Compound 7

4.50 g (7.69 mmol) of Intermediate 1d, 1.88 g (7.69 mmol) of 4-(naphthalene-1-yl-amino)benzonitrile, 0.14 g (0.15 mmol) of Pd₂(dba)₃, 0.02 g (0.15 mmol) P(tBu)₃, and 1.10 g (11.5 mmol) of NaOtBu were dissolved in 70 mL of toluene, and then stirred at a temperature of about 80° C. for about 4 hours. The reaction solution was cooled to room temperature, and then, 40 mL of water was added thereto, and extracted three times with 50 mL of ethylether. An organic layer obtained therefrom was dried with magnesium sulfate and a solvent was evaporated and the residual was separation-purified by silicagel column chromatography to obtain 4.32 g (Yield: 75%) of Compound 7. The obtained compound was identified by ¹H NMR and MS/FAB (C₅₇H₃₆N₂: calc. 748.29. found 748.30).

Synthesis of Compound 20

4.30 g (Yield: 72%) of Compound 20 was synthesized in the same manner as used to synthesize Compound 7, except that 4-(4-pyridine-3-yl-phenylamino)benzonitrile was used instead of 4-(naphthalene-1-yl-amino)benzonitrile. The obtained compound was identified by ¹H NMR and MS/FAB (C₅₈H₃₇N₃: calc. 775.30. found 775.32).

Synthesis of Compound 25

4.21 g (Yield: 68%) of Compound 25 was synthesized in the same manner as used to synthesize Compound 7, except that 4-(dibenzothiophene-3-yl-amino)benzonitrile was used instead of 4-(naphthalene-1-yl-amino)benzonitrile. The obtained compound was identified by ¹H NMR and MS/FAB (C₅₉H₃₆N₂S: calc. 804.26. found 804.25).

Synthesis of Compound 28

4.60 g (Yield: 70%) of Compound 28 was synthesized in the same manner as used to synthesize Compound 7, except that 4-(4,6-diphenyl-[1,3,5]triazine-2-yl-amino)benzonitrile was used instead of 4-(naphthalene-1-yl-amino)benzonitrile. The obtained compound was identified by ¹H NMR and MS/FAB (C₆₂H₃₉N₅: calc. 853.32. found 853.33).

Synthesis of Compound 32

4.21 g (Yield: 73%) of Compound 32 was synthesized in the same manner as used to synthesize Compound 7, except that 4-(quinoline-6-yl-amino)benzonitrile was used instead of 4-(naphthalene-1-yl-amino)benzonitrile. The obtained compound was identified by ¹H NMR and MS/FAB (C₅₆H₃₅N₃: calc. 749.28. found 749.30).

Synthesis of Compound 45

4.34 g (Yield: 69%) of Compound 45 was synthesized in the same manner as used to synthesize Intermediate 1d, except that 4,4'-dibromo-biphenyl was used instead of 1,4-dibromobenzene, and to synthesize Compound 7, except that 4-fluoro-phenyl)naphthalene-2-ylamine was used instead of 4-(naphthalene-1-yl-amino)benzonitrile. The obtained compound was identified by ¹H NMR and MS/FAB (C₆₂H₄₀FN: calc. 817.31. found 817.30).

Synthesis of Compound 50

4.59 g (Yield: 67%) of Compound 50 was synthesized in the same manner as used to synthesize Compound 45, except that 4-(9,9-dimethyl-9H-fluorene-2-yl-amino)benzonitrile was used instead of (4-fluoro-phenyl)naphthalene-2-

Synthesis of Compound 60

4.39 g (Yield: 66%) of Compound 60 was synthesized in the same manner as used to synthesize Compound 45, except that 4-(dibenzofuran-2-yl-amino)benzonitrile was used instead of (4-fluoro-phenyl)naphthalene-2-ylamine. The obtained compound was identified by $^1$H NMR and MS/FAB ($C_{65}H_{40}N_2O$: calc. 864.31. found 864.32).

Synthesis of Compound 65

4.31 g (Yield: 68%) of Compound 65 was synthesized in the same manner as used to synthesize Intermediate 1d, except that 2,6-dibromo-naphthalene was used instead of 1,4-dibromobenzene, and to synthesize Compound 7, except that 4-(biphenyl-4-yl-amino)benzonitril was used instead of 4-(naphthalene-1-yl-amino)benzonitrile. The obtained compound was identified by $^1$H NMR and MS/FAB ($C_{63}H_{40}N_2$: calc. 824.32. found 824.33).

Synthesis of Compound 72

4.00 g (Yield: 63%) of Compound 72 was synthesized in the same manner as used to synthesize Compound 65, except that 4-(4-pyridine-4-yl-phenylamino)benzonitrile was used instead of 4-(biphenyl-4-yl-amino)benzonitrile. The obtained compound was identified by $^1$H NMR and MS/FAB ($C_{62}H_{39}N_3$: calc. 825.31. found 825.30).

Synthesis of Compound 81

4.70 g (Yield: 65%) of Compound 81 was synthesized in the same manner as used to synthesize Compound 65, except that 4-[4-(1-phenyl-1H-benzoimidazole-2-yl)phenylamino]benzonitrile was used instead of 4-(biphenyl-4-yl-amino)benzonitrile. The obtained compound was identified by $^1$H NMR and MS/FAB ($C_{70}H_{44}N_4$: calc. 940.36. found 940.39).

Synthesis of Compound 103

4.05 g (Yield: 68%) of Compound 103 was synthesized in the same manner as used to synthesize Intermediate 1d, except that 1,4-dibromo-naphthalene was used instead of 1,4-dibromobenzene, and to synthesize Compound 7, except that bis-(4-cyano-phenyl)amine was used instead of 4-(naphthalene-1-yl-amino)benzonitrile. The obtained compound was identified by $^1$H NMR and MS/FAB ($C_{58}H_{35}N_3$: calc. 773.28. found 773.30).

Synthesis of Compound 114

4.79 g (Yield: 72%) of Compound 114 was synthesize in the same manner as used to synthesize Intermediate 1d, except that 2,7-dibromo-9,9-dimethyl-9H-fluorene was used instead of 1,4-dibromobenzene, and to synthesize Compound 7, except that 4-(naphthalene-1-ylamino)benzonitrile was used instead of 4-(naphthalene-1-yl-amino)benzonitrile. The obtained compound was identified by $^1$H NMR and MS/FAB ($C_{66}H_{44}N_2$: calc. 864.35. found 864.33).

Synthesis of Compound 125

4.03 g (Yield: 70%) Compound 125 was synthesized in the same manner as used to synthesize Intermediate 1b, except that 1-bromonaphthalene was used instead of 2-bromonaphthalene, and to synthesize Compound 7, except that 4-(naphthalene-2-yl-amino)benzonitril was used instead of 4-(naphthalene-1-yl-amino)benzonitrile. The obtained compound was identified by $^1$H NMR and MS/FAB ($C_{57}H_{36}N_2$: calc. 748.29. found 748.31).

Synthesis of Compound 132

3.91 g (Yield: 63%) of Compound 132 was synthesized in the same manner as used to synthesize Compound 125, except that 9,9-dimethyl-9H-fluorene-2-yl-(4-fluoro-phenyl)amine was used instead of 4-(naphthalene-2-yl-amino)benzonitril. The obtained compound was identified by $^1$H NMR and MS/FAB ($C_{61}H_{42}FN$: calc. 807.33. found 807.30).

Synthesis of Compound 140

4.24 g (Yield: 65%) of Compound 140 was synthesized in the same manner as used to synthesize Intermediate 1b, except that 9-bromophenanthrene was used instead of 2-bromonaphthalene, and to synthesize Compound 7, except that 4-(naphthalene-2-ylamine)benzonitrile was used instead of 4-(naphthalene-1-yl-amino)benzonitrile. The obtained compound was identified by $^1$H NMR and MS/FAB ($C_{65}H_{40}N_2$: calc. 848.32. found 848.33).

Synthesis of Compound 149

3.86 g (Yield: 62%) of Compound 149 was synthesized in the same manner as used to synthesize Compound 140, except that bis-(4-fluoro-phenyl)amine was used instead of 4-(naphthalene-2-ylamine)benzonitrile. The obtained compound was identified by $^1$H NMR and MS/FAB ($C_{60}H_{37}F_2N$: calc. 809.29. found 809.27).

Synthesis of Compound 159

4.67 g (Yield: 67%) of Compound 159 was synthesized in the same manner as used to synthesize Intermediate 1b, except that 2-bromo-9,9-dimethyl-9H-fluorene was used instead of 2-bromonaphthalene, and to synthesize Compound 7, except that 4-(bisphenyl-4-yl-amino)benzonitrile was used instead of 4-(naphthalene-1-yl-amino)benzonitrile. The obtained compound was identified by $^1$H NMR and MS/FAB ($C_{69}H_{50}N_2$: calc. 906.40. found 906.42).

Synthesis of Compound 162

4.77 g (Yield: 66%) of Compound 162 was synthesized in the same manner as used to synthesize Compound 159, except that 9,9-dimethyl-9H-fluorene-2-yl-(4-fluoro-phenyl)amine was used instead of 4-(bisphenyl-4-yl-amino)benzonitrile. The obtained compound was identified by ¹H NMR and MS/FAB ($C_{71}H_{54}FN$: calc. 939.42. found 939.43).

Synthesis of Compound 170

3.23 g (Yield: 60%) of Compound 170 was synthesized in the same manner as used to synthesize Intermediate 1b, except that 3-bromo-pyridine was used instead of 1 equivalent of 2-bromonaphthalene, and to synthesize Compound 7, except that 4-(naphthalene-2-yl-amino)benzonitrile was used instead of 4-(naphthalene-1-yl-amino)benzonitrile. The obtained compound was identified by ¹H NMR and MS/FAB ($C_{52}H_{33}N_3$: calc. 699.27. found 699.26).

By using the same method of the synthetic methods above, and suitable Intermediate materials, other additional compounds may be formed. Results of ¹H NMR and MS/FAB of the obtained compounds are shown in Table 1 below.

In addition to the compounds shown in Table 1, it would be obvious to those of ordinary skill in the art to easily recognize the same method and materials as those described above.

TABLE 1

| Compound | ¹H NMR (CDCl₃, 400 MHz) |
|---|---|
| 7 | δ = 8.38 (d, 1H), 8.16 (d, 2H), 7.89-7.76 (m, 7H), 7.72-7.69 (m, 4H), 7.58 (d, 1H), 7.51-7.30 (m, 13H), 7.23 (t, 1H), 7.15 (t, 2H), 7.03-7.00 (m, 2H), 6.93 (d, 1H), 6.86-6.83 (m, 2H) |
| 20 | δ = 8.90 (d, 1H), 8.60 (d, 1H), 8.38 (d, 1H), 8.16 (d, 1H), 7.92 (d, 1H), 7.89 (s, 1H), 7.82-7.77 (m, 5H), 7.73-7.69 (m, 4H), 7.58 (d, 1H), 7.54-7.25 (m, 13H), 7.16 (t, 2H), 7.05-7.02 (m, 2H), 6.97-6.96 (m, 2H), 6.91-6.88 (m, 2H) |
| 25 | δ = 8.38 (d, 1H), 8.19-8.12 (m, 3H), 7.90 (s, 1H), 7.86-7.80 (m, 6H), 7.75-7.71 (m, 4H), 7.58 (d, 1H), 7.56-7.33 (m, 12H), 7.25 (d, 1H), 7.17-7.12 (m, 5H), 7.05-7.02 (m, 2H) |
| 28 | δ = 8.70-8.68 (m, 4H), 8.38 (d, 1H), 8.16 (d, 1H), 7.90 (s, 1H), 7.85-7.72 (m, 11H), 7.59-7.56 (m, 5H), 7.52-7.31 (m, 12H), 7.26-7.23 (m, 2H), 7.13 (t, 2H) |
| 32 | δ = 8.91 (d, 1H), 8.39 (d, 1H), 8.15 (d, 1H), 8.10 (d, 1H), 8.05 (d, 1H), 7.92 (s, 1H), 7.83-7.77 (m, 5H), 7.73-7.70 (m, 4H), 7.57 (d, 1H), 7.53-7.31 (m, 13H), 7.17 (t, 2H), 7.13-7.10 (m, 2H), 7.01-6.98 (m, 2H) |
| 45 | δ = 8.37 (d, 1H), 8.17 (d, 1H), 7.91-7.76 (m, 9H), 7.72-7.64 (m, 7H), 7.59-7.32 (m, 13H), 7.18-7.12 (m, 5H), 7.03-6.99 (m, 2H), 6.95-6.92 (m, 2H) |
| 50 | δ = 8.38 (d, 1H), 8.16 (d, 1H), 7.92-7.80 (m, 8H), 7.18 (d, 1H), 7.72-7.67 (m, 6H), 7.60-7.49 (m, 6H), 7.46-7.39 (m, 6H), 7.26-7.22 (m, 7H), 7.17 (d, 1H), 7.06-7.03 (m, 2H), 6.97 (d, 1H), 1.61 (s, 6H) |
| 60 | δ = 8.39 (d, 1H), 8.15 (d, 1H), 7.91 (d, 1H), 7.89-7.81 (m, 8H), 7.75-7.67 (m, 7H), 7.60-7.32 (m, 15H), 7.22-7.18 (m, 3H), 7.13-7.10 (m, 2H), 7.03-6.98 (m, 2H) |
| 65 | δ = 8.47 (d, 1H), 8.38 (d, 1H), 8.21 (d, 1H), 8.16 (d, 1H), 7.90 (d, 1H), 7.85-7.80 (m, 6H), 7.73-7.70 (m, 5H), 7.67-7.33 (m, 17H), 7.23 (d, 1H), 7.17 (t, 2H), 7.06-7.02 (m, 2H), 6.98-6.95 (m, 2H) |
| 72 | δ = 8.72-8.70 (m, 2H), 8.47 (d, 1H), 8.38 (d, 1H), 8.21 (d, 1H), 8.16 (d, 1H), 7.90 (d, 1H), 7.85-7.81 (m, 6H), 7.72-7.69 (m, 5H), 7.60-7.52 (m, 7H), 7.43-7.35 (m, 7H), 7.27 (d, 1H), 7.16 (t, 2H), 7.07-7.02 (m, 4H) |
| 81 | δ = 8.47 (d, 1H), 8.38 (d, 1H), 8.21 (d, 1H), 8.17 (d, 1H), 7.91 (d, 1H), 7.87-7.82 (m, 9H), 7.77-7.74 (m, 5H), 7.70 (d, 1H), 7.62-7.55 (m, 5H), 7.46-7.30 (m, 11H), 7.23 (t, 1H), 7.15 (d, 1H), 7.10 (t, 2H), 7.01-6.97 (m, 4H) |
| 103 | δ = 8.54 (d, 1H), 8.38 (d, 1H), 8.27 (d, 1H), 7.90 (d, 1H), 7.85-7.82 (m, 5H), 7.73-7.70 (m, 4H), 7.58 (d, 1H), 7.53-7.47 (m, 5H), 7.43-7.35 (m, 8H), 7.16-7.12 (m, 4H), 7.03-6.99 (m, 4H) |
| 114 | δ = 8.41 (d, 1H), 8.39 (d, 1H), 8.13-8.11 (m, 2H), 7.87-7.67 (m, 12H), 7.62 (d, 1H), 7.58 (d, 1H), 7.52-7.30 (m, 13H), 7.15 (t, 2H), 7.07 (d, 1H), 7.00-6.96 (m, 3H), 6.92 (d, 1H), 1.63 (s, 6H) |
| 125 | δ = 8.06 (s, 1H), 7.99-7.97 (m, 2H), 7.93-7.88 (m, 8H), 7.78-7.74 (m, 3H), 7.71-7.55 (m, 12H), 7.41-7.33 (m, 5H), 7.26 (d, 1H), 7.20-7.16 (m, 2H), 7.12-7.08 (2H) |
| 132 | δ = 8.05 (s, 1H), 8.00-7.98 (m, 2H), 7.95-7.90 (m, 8H), 7.79-7.74 (m, 3H), 7.71-7.65 (m, 2H), 7.62-7.53 (m, 7H), 7.45-7.35 (m, 3H), 7.26-7.23 (m, 2H), 7.17-7.12 (m, 2H), 7.06 (d, 1H), 6.97-6.92 (m, 4H), 6.87 (d, 1H), 1.61 (s, 6H) |
| 140 | δ = 8.69 (d, 2H), 8.48 (d, 2H), 8.16 (d, 1H), 8.06 (d, 1H), 7.94 (d, 2H), 7.89 (d, 2H), 7.85-7.76 (m, 6H), 7.70-7.51 (m, 12H), 7.41-7.33 (m, 5H), 7.18 (t, 2H), 7.10 (d, 1H), 7.06-7.03 (m, 2H), 6.97-6.93 (m, 2H) |
| 149 | δ = 8.69 (d, 2H), 8.48 (d, 2H), 8.17 (d, 1H), 8.06 (d, 1H), 7.94 (d, 2H), 7.90 (d, 2H), 7.87-7.83 (m, 3H), 7.80 (d, 2H), 7.75-7.72 (m, 4H), 7.61-7.57 (m), 7.55-7.52 (m) (4H), 7.46-7.41 (m, 2H), 7.19 (t, 2H), 7.13-7.09 (m, 4H), 7.05-7.02 (m, 2H), 6.98-6.94 (m, 4H) |
| 159 | δ = 7.94-7.90 (m, 4H), 7.85 (s, 1H), 7.83-7.69 (m, 7H), 7.66-7.63 (m, 2H), 7.57-7.38 (m, 14H), 7.32-7.28 (m, 4H), 7.22-7.17 (m, 4H), 7.07-7.03 (m, 2H), 1.61 (s, 12H) |
| 162 | δ = 7.95-7.91 (m, 4H), 7.85-7.72 (m, 9H), 7.67-7.62 (m, 3H), 7.57 (d, 1H), 7.53-7.45 (m, 5H), 7.40-7.35 (m, 6H), 7.27-7.23 (m, 2H), 7.15 (d, 1H), 7.09-7.05 (m, 4H), 7.02 (d, 1H), 1.61 (s, 18H) |

TABLE 1-continued

| Compound | $^1$H NMR (CDCl$_3$, 400 MHz) |
|---|---|
| 166 | δ = 7.87-7.76 (m, 6H), 7.72-7.67 (m, 4H), 7.59 (d, 1H), 7.56-7.49 (m, 4H), 7.45-7.36 (m, 6H), 7.23-7.19 (m, 3H), 7.06 (t, 1H), 6.99-6.96 (m, 2H), 6.92 (t, 1H), 6.89-6.86 (m, 2H), 6.82-6.79 (m, 2H) |
| 167 | δ = 8.67 (d, 1H), 8.49 (d, 1H), 8.16 (d, 1H), 7.93 (d, 1H), 7.91-7.75 (m, 9H), 7.69-7.65 (m, 3H), 7.62 (t, 1H), 7.57-7.38 (m, 12H), 7.25 (t, 1H), 7.16 (t, 1H), 7.08-7.04 (m, 2H), 7.00 (d, 1H), 6.97-6.93 (m, 2H) |
| 170 | δ = 9.08 (d, 1H), 8.60 (d, 1H), 7.93-7.82 (m, 6H), 7.76-7.50 (m, 12H), 7.42-7.33 (m, 7H), 7.25-7.21 (m, 2H), 7.17-7.14 (m, 2H), 7.10-7.07 (m, 2H) |

Example 1

An anode was prepared by cutting a Corning 15 Ω/cm$^2$ (1200 Å) ITO glass substrate to a size of 50 mm×50 mm×0.7 mm, sonicated in isopropyl alcohol for about 5 minutes and in pure water for about 5 minutes, and then cleaned by irradiation of ultraviolet rays for about 30 minutes, and exposed to ozone. The resulting glass substrate was loaded into a vacuum deposition device.

2-TNATA was vacuum deposited on the anode to a thickness of about 600 Å to form an HIL, and 4'-bis[N-(1-naphthyl)-N-phenylamino]biphenyl (hereinafter, NPB) as a hole transporting compound was vacuum-deposited on the HIL to a thickness of about 300 Å.

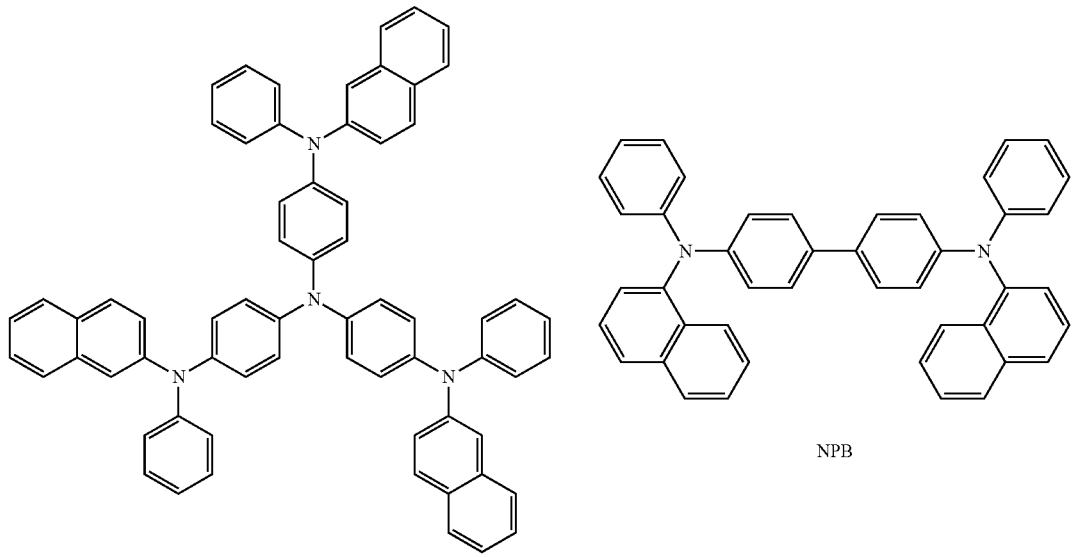

2-TNATA

NPB

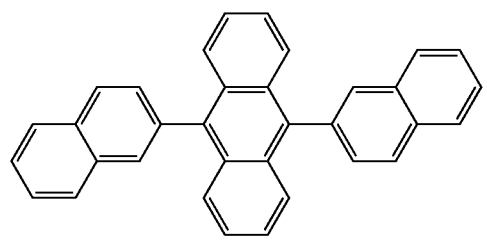

ADN

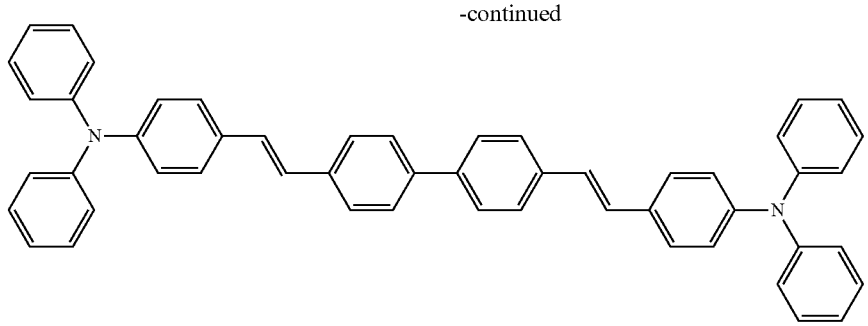

DPAVBi 9,10-di-naphthalene-2-yl-anthracene (hereinafter, ADN) as a known blue fluorescent host, and 4,4'-bis[2-(4-(N,N-diphenylamino)phenyl)vinyl]biphenyl (hereinafter, DPAVBi) as a known blue fluorescent dopant, were co-deposited at a weight ratio of about 98:2 on the HTL to form an EML having a thickness of 300 Å.

Next, Compound 7 of the present embodiments was deposited on the EML to form an ETL to a thickness of about 300 Å, and then LiF, which is a halogenated alkali metal, was deposited on the ETL to form an EIL to a thickness of about 10 Å. Then, AL was vacuum-deposited on the EIL to form a cathode having a thickness of about 3,000 Å, thereby forming a LiF/Al electrode and completing the manufacture of an OLED.

The OLED had a driving voltage of about 5.41 V at a current density of 50 mA/cm$^2$, a luminescent efficiency of 3,230 cd/m$^2$, and a half life-span (hr @100 mA/cm$^2$) of about 513 hours.

Example 2

An OLED was manufactured in the same manner as in Example 1, except that Compound 20 was used instead of Compound 7 to form the ETL.

The OLED had a driving voltage of about 5.32 V at a current density of 50 mA/cm$^2$, a luminosity of 3,165 cd/m$^2$, a luminescent efficiency of 6.33 cd/A, and a half life-span (hr @100 mA/cm$^2$) of about 397 hours.

Example 3

An OLED was manufactured in the same manner as in Example 1, except that Compound 25 was used instead of Compound 7 to form the ETL.

The OLED had a driving voltage of about 5.26 V at a current density of 50 mA/cm$^2$, a luminosity of 3,380 cd/m$^2$, a luminescent efficiency of 6.76 cd/A, and a half life-span (hr @100 mA/cm$^2$) of about 397 hours.

Example 4

An OLED was manufactured in the same manner as in Example 1, except that Compound 28 was used instead of Compound 7 to form the ETL.

The OLED had a driving voltage of about 5.03 V at a current density of 50 mA/cm$^2$, a luminosity of 2,960 cd/m$^2$, a luminescent efficiency of 5.92 cd/A, and a half life-span (hr @100 mA/cm$^2$) of about 238 hours.

Example 5

An OLED was manufactured in the same manner as in Example 1, except that Compound 32 was used instead of Compound 7 to form the ETL.

The OLED had a driving voltage of about 5.26 V at a current density of 50 mA/cm$^2$, a luminosity of 3,465 cd/m$^2$, a luminescent efficiency of 6.93 cd/A, and a half life-span (hr @100 mA/cm$^2$) of about 536 hours.

Example 6

An OLED was manufactured in the same manner as in Example 1, except that Compound 45 was used instead of Compound 7 to form the ETL.

The OLED had a driving voltage of about 5.21 V at a current density of 50 mA/cm$^2$, a luminosity of 3,505 cd/m$^2$, a luminescent efficiency of 7.01 cd/A, and a half life-span (hr @100 mA/cm$^2$) of about 564 hours.

Example 7

An OLED was manufactured in the same manner as in Example 1, except that Compound 50 was used instead of Compound 7 to form the ETL.

The OLED had a driving voltage of about 5.26 V at a current density of 50 mA/cm$^2$, a luminosity of 3,280 cd/m$^2$, a luminescent efficiency of 6.56 cd/A, and a half life-span (hr @100 mA/cm$^2$) of about 632 hours.

Example 8

An OLED was manufactured in the same manner as in Example 1, except that Compound 60 was used instead of Compound 7 to form the ETL.

The OLED had a driving voltage of about 5.41 V at a current density of 50 mA/cm$^2$, a luminosity of 3,260 cd/m$^2$, a luminescent efficiency of 6.52 cd/A, and a half life-span (hr @100 mA/cm$^2$) of about 431 hours.

Example 9

An OLED was manufactured in the same manner as in Example 1, except that Compound 65 was used instead of Compound 7 to form the ETL.

The OLED had a driving voltage of about 5.32 V at a current density of 50 mA/cm$^2$, a luminosity of 3,395 cd/m$^2$, a luminescent efficiency of 6.79 cd/A, and a half life-span (hr @100 mA/cm$^2$) of about 499 hours.

Example 10

An OLED was manufactured in the same manner as in Example 1, except that Compound 72 was used instead of Compound 7 to form the ETL.

The OLED had a driving voltage of about 5.31 V at a current density of 50 mA/cm$^2$, a luminosity of 3,435 cd/m$^2$, a luminescent efficiency of 6.87 cd/A, and a half life-span (hr @100 mA/cm$^2$) of about 524 hours.

Example 11

An OLED was manufactured in the same manner as in Example 1, except that Compound 81 was used instead of Compound 7 to form the ETL.

The OLED had a driving voltage of about 5.26 V at a current density of 50 mA/cm$^2$, a luminosity of 3,580 cd/m$^2$, a luminescent efficiency of 7.16 cd/A, and a half life-span (hr @100 mA/cm$^2$) of about 532 hours.

Example 12

An OLED was manufactured in the same manner as in Example 1, except that Compound 103 was used instead of Compound 7 to form the ETL.

The OLED had a driving voltage of about 5.24 V at a current density of 50 mA/cm$^2$, a luminosity of 3,515 cd/m$^2$, a luminescent efficiency of 7.03 cd/A, and a half life-span (hr @100 mA/cm$^2$) of about 582 hours.

Example 13

An OLED was manufactured in the same manner as in Example 1, except that Compound 114 was used instead of Compound 7 to form the ETL.

The OLED had a driving voltage of about 5.31 V at a current density of 50 mA/cm$^2$, a luminosity of 3,605 cd/m$^2$, a luminescent efficiency of 7.21 cd/A, and a half life-span (hr @100 mA/cm$^2$) of about 529 hours.

Example 14

An OLED was manufactured in the same manner as in Example 1, except that Compound 125 was used instead of Compound 7 to form the ETL.

The OLED had a driving voltage of about 5.79 V at a current density of 50 mA/cm$^2$, a luminosity of 3,015 cd/m$^2$, a luminescent efficiency of 6.03 cd/A, and a half life-span (hr @100 mA/cm$^2$) of about 273 hours.

Example 15

An OLED was manufactured in the same manner as in Example 1, except that Compound 132 was used instead of Compound 7 to form the ETL.

The OLED had a driving voltage of about 5.32 V at a current density of 50 mA/cm$^2$, a luminosity of 3,460 cd/m$^2$, a luminescent efficiency of 6.92 cd/A, and a half life-span (hr @100 mA/cm$^2$) of about 543 hours.

Example 16

An OLED was manufactured in the same manner as in Example 1, except that Compound 140 was used instead of Compound 7 to form the ETL.

The OLED had a driving voltage of about 5.43 V at a current density of 50 mA/cm$^2$, a luminosity of 3,445 cd/m$^2$, a luminescent efficiency of 6.89 cd/A, and a half life-span (hr @100 mA/cm$^2$) of about 469 hours.

Example 17

An OLED was manufactured in the same manner as in Example 1, except that Compound 149 was used instead of Compound 7 to form the ETL.

The OLED had a driving voltage of about 5.62 V at a current density of 50 mA/cm$^2$, a luminosity of 3,070 cd/m$^2$, a luminescent efficiency of 6.14 cd/A, and a half life-span (hr @100 mA/cm$^2$) of about 322 hours.

Example 18

An OLED was manufactured in the same manner as in Example 1, except that Compound 159 was used instead of Compound 7 to form the ETL.

The OLED had a driving voltage of about 5.43 V at a current density of 50 mA/cm$^2$, a luminosity of 3,445 cd/m$^2$, a luminescent efficiency of 6.89 cd/A, and a half life-span (hr @100 mA/cm$^2$) of about 469 hours.

Example 19

An OLED was manufactured in the same manner as in Example 1, except that Compound 162 was used instead of Compound 7 to form the ETL.

The OLED had a driving voltage of about 5.62 V at a current density of 50 mA/cm$^2$, a luminosity of 3,070 cd/m$^2$, a luminescent efficiency of 6.14 cd/A, and a half life-span (hr @100 mA/cm$^2$) of about 322 hours.

Example 20

An OLED was manufactured in the same manner as in Example 1, except that Compound 170 was used instead of Compound 7 to form the ETL.

The OLED had a driving voltage of about 5.57 V at a current density of 50 mA/cm$^2$, a luminosity of 3,350 cd/m$^2$, a luminescent efficiency of 6.72 cd/A, and a half life-span (hr @100 mA/cm$^2$) of about 423 hours.

Example 21

An OLED was manufactured in the same manner as in Example 1, except that Compound 7 was used instead of ADN that was used as a host to form the EML, and the known Alq3 was used instead of Compound 7 to form the ETL.

The OLED had a driving voltage of about 6.82 V at a current density of 50 mA/cm$^2$, a luminosity of 2,240 cd/m$^2$, a luminescent efficiency of 4.48 cd/A, and a half life-span (hr @100 mA/cm$^2$) of about 193 hours.

Example 22

An OLED was manufactured in the same manner as in Example 1, except that Compound 32 was used instead of Compound 7 to form the EML.

The OLED had a driving voltage of about 6.73 V at a current density of 50 mA/cm$^2$, a luminosity of 2,130 cd/m$^2$, a luminescent efficiency of 4.26 cd/A, and a half life-span (hr @100 mA/cm$^2$) of about 186 hours.

Example 23

An OLED was manufactured in the same manner as in Example 1, except that Compound 20 was used instead of DPAVBi as a dopant and the known AND was used as a host, Alq3 was used to form ETL instead of Compound 7.

The OLED had a driving voltage of about 6.86 V at a current density of 50 mA/cm$^2$, a luminosity of 2,190 cd/m$^2$, a luminescent efficiency of 4.38 cd/A, and a half life-span (hr @100 mA/cm$^2$) of about 1216 hours.

Example 24

An OLED was manufactured in the same manner as in Example 1, except that Compound 103 was used instead of DPAVBi as a dopant and known AND was used as a host and Alq3 was used to form ETL instead of Compound 7.

The OLED had a driving voltage of about 6.97 V at a current density of 50 mA/cm$^2$, a luminosity of 2,260 cd/m$^2$, a luminescent efficiency of 4.52 cd/A, and a half life-span (hr @100 mA/cm$^2$) of about 238 hours.

Comparative Example 1

An OLED was manufactured in the same manner as in Example 1, except that the known Alq$_3$ was used instead of Compound 7 to form the ETL.

The OLED had a driving voltage of about 7.35 V at a current density of 50 mA/cm$^2$, a luminosity of 2,065 cd/m$^2$, a luminescent efficiency of 4.13 cd/A, and a half life-span (hr @100 mA/cm$^2$) of about 145 hours.

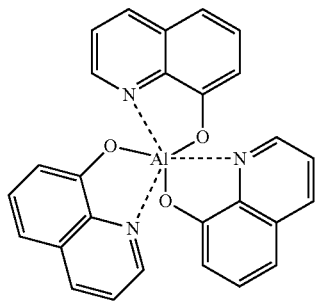

Alq$_3$

Comparative Example 2

An OLED was manufactured in the same manner as in Example 1, except that Compound 300 was used instead of Compound 7 to form the ETL.

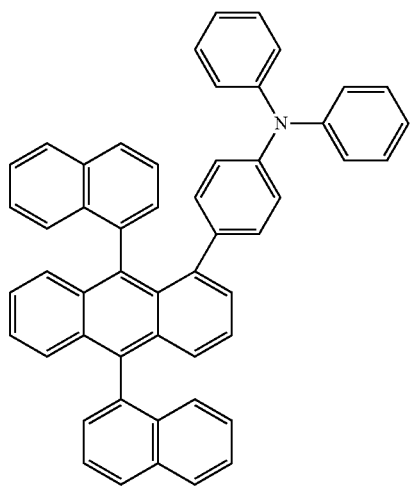

300

The OLED had a driving voltage of about 6.02 V at a current density of 50 mA/cm$^2$, a luminosity of 2,765 cd/m$^2$, a luminescent efficiency of 5.82 cd/A, and a half life-span (hr @100 mA/cm$^2$) of about 256 hours.

The arylamine compound of Formula 1 according to the present embodiments was evaluated as an electron-transporting material, and as a host and a dopant of the EML in the OLED. When the compound was used as the electron-transporting material, compared to the known Alq$_3$, the OLED including the compound had a driving voltage, which was decreased by more than 1 V, and showed excellent I-V-L characteristics with greatly improved efficiency, in particularly with regard to lifetime improvement. When the compound was used as the host and dopant, the OLED including the compound showed slightly improved IV and efficiency characteristics as well as lifetime that was slightly increased. As a result, it was confirmed that the arylamine compound including anthracene according to the present embodiments has an excellent effect as an electron-transporting material. Results of Examples and representative lifetimes thereof are summarized and shown in Table 2 below:

TABLE 2

| | Electron-transporting material or a light-emitting layer material | Driving voltage (V) | Current density (mA/cm2) | Brightness (cd/m2) | Efficiency (cd/A) | Luminescence color | Half-life lifetime (hr @100 mA/cm$^2$) |
|---|---|---|---|---|---|---|---|
| Example 1 | Compound 7 | 5.41 | 50 | 3,230 | 6.46 | Blue | 513 hr |
| Example 2 | Compound 20 | 5.32 | 50 | 3,165 | 6.33 | Blue | 397 hr |
| Example 3 | Compound 25 | 5.26 | 50 | 3,380 | 6.76 | Blue | 487 hr |
| Example 4 | Compound 28 | 5.03 | 50 | 2,960 | 5.92 | Blue | 238 hr |
| Example 5 | Compound 32 | 5.26 | 50 | 3,465 | 6.93 | Blue | 536 hr |
| Example 6 | Compound 45 | 5.21 | 50 | 3,505 | 7.01 | Blue | 564 hr |
| Example 7 | Compound 50 | 5.26 | 50 | 3,280 | 6.56 | Blue | 632 hr |
| Example 8 | Compound 60 | 5.41 | 50 | 3,260 | 6.52 | Blue | 431 hr |
| Example 9 | Compound 65 | 5.32 | 50 | 3,395 | 6.79 | Blue | 499 hr |
| Example 10 | Compound 72 | 5.31 | 50 | 3,435 | 6.87 | Blue | 524 hr |
| Example 11 | Compound 81 | 5.26 | 50 | 3,580 | 7.16 | Blue | 532 hr |
| Example 12 | Compound 103 | 5.24 | 50 | 3,515 | 7.03 | Blue | 582 hr |
| Example 13 | Compound 114 | 5.31 | 50 | 3,605 | 7.21 | Blue | 529 hr |
| Example 14 | Compound 125 | 5.79 | 50 | 3,015 | 6.03 | Blue | 273 hr |
| Example 15 | Compound 132 | 5.32 | 50 | 3,460 | 6.92 | Blue | 543 hr |
| Example 16 | Compound 140 | 5.43 | 50 | 3,445 | 6.89 | Blue | 469 hr |
| Example 17 | Compound 149 | 5.62 | 50 | 3,070 | 6.14 | Blue | 322 hr |
| Example 18 | Compound 159 | 5.43 | 50 | 3,445 | 6.89 | Blue | 469 hr |
| Example 19 | Compound 162 | 5.62 | 50 | 3,070 | 6.14 | Blue | 322 hr |
| Example 20 | Compound 170 | 5.57 | 50 | 3,350 | 6.72 | Blue | 423 hr |
| Example 21 | Compound 7 | 6.82 | 50 | 2,240 | 4.48 | Blue | 193 hr |
| Example 22 | Compound 32 | 6.73 | 50 | 2,130 | 4.26 | Blue | 186 hr |
| Example 23 | Compound 20 | 6.86 | 50 | 2,190 | 4.38 | Blue | 216 hr |
| Example 24 | Compound 103 | 6.97 | 50 | 2,260 | 4.52 | Blue | 238 hr |
| Comparative Example 1 | Alq$_3$ | 7.35 | 50 | 2,065 | 4.13 | Blue | 145 hr |
| Comparative Example 2 | Compound 300 | 6.02 | 50 | 2,565 | 5.57 | Blue | 236 hr |

As described above, a novel arylamine compound represented by Formula 1 above has an improved light-emitting capability and charge transporting capability, and thus may be used as a charge injecting material or a charge transporting material that is suitable for any fluorescent and phosphorescent devices of any color of red, green, blue, or white. The compound is particularly suitable as a light-emitting material for fluorescent device of green, blue, and white. Therefore, an organic light-emitting device having high efficiency, low driving voltages, high luminance, and long lifetime may be manufactured using the compound.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:
1. A compound represented by Formula 1 below:

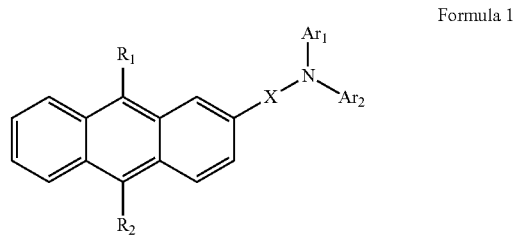

Formula 1 wherein, in Formula 1, $R_1$ and $R_2$ are each independently a substituted or unsubstituted $C_6$-$C_{60}$ aryl group, a substituted or unsubstituted $C_2$-$C_{60}$ heteroaryl group, or a substituted or unsubstituted $C_6$-$C_{60}$ condensed polycyclic group;

$Ar_1$ is a $C_6$-$C_{60}$ aryl group substituted with CN or F, a substituted or unsubstituted $C_2$-$C_{60}$ heteroaryl group (excluding a substituted or unsubstituted pyridyl group and a substituted or unsubstituted isoquinolyl group), or a substituted $C_6$-$C_{60}$ condensed polycyclic group;

$Ar_2$ is a substituted or unsubstituted $C_6$-$C_{60}$ aryl group, a substituted or unsubstituted $C_2$-$C_{60}$ heteroaryl group (excluding a substituted or unsubstituted pyridyl group), or a substituted or unsubstituted $C_6$-$C_{60}$ condensed polycyclic group; and X is a substituted or unsubstituted $C_6$-$C_{60}$ aryl group, a substituted or unsubstituted $C_2$-$C_{60}$ heteroaryl group, a substituted or unsubstituted $C_6$-$C_{60}$ condensed polycyclic group, or a divalent linking group with at least two of the aryl group, the heteroaryl group, and the condensed polycyclic group linked together.

2. The compound of claim 1, wherein $R_1$ and $R_2$ are identical to each other.

3. The compound of claim 1, wherein $R_1$ and $R_2$ are each independently one of the following compounds represented by Formulas 2a to 2f below:

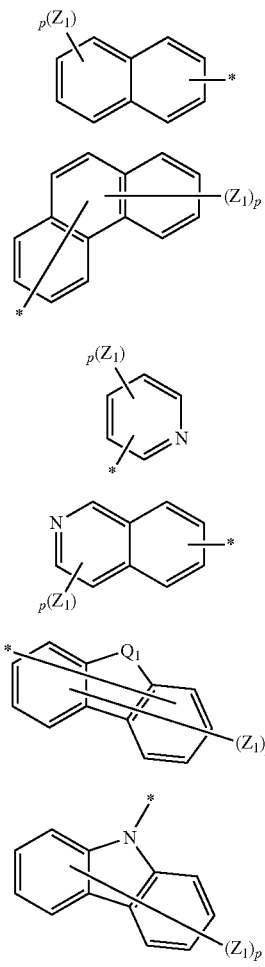

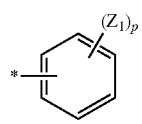

wherein, in Formulas 2a to 2e, $Q_1$ is a linking group represented by —C($R_{30}$)($R_{31}$)— or —N($R_{32}$)—;

$Z_1$, $R_{30}$, $R_{31}$, and $R_{32}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano atom, a nitro group, a hydroxyl group, or a carboxyl group;

p is an integer from 1 to 9; and

* is a binding site.

4. The compound of claim 1, wherein $Ar_2$ is a linking group with at least one of the following groups represented by Formulas 3a to 3e below:

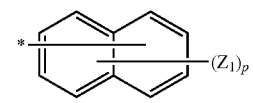

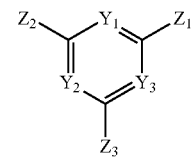

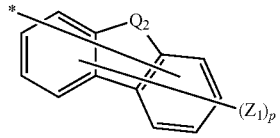

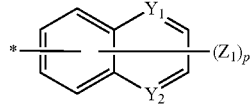

wherein, in Formulas 3a to 3e, $Y_1$ and $Y_2$ are each independently a linking group represented by —N= or —C($R_{21}$)=;

$Q_2$ is a linking group represented by —C($R_{30}$)($R_{31}$)—, —N($R_{32}$)—, —S—, or —O—;

$Z_1$, $Z_2$, $R_{21}$, $R_{30}$, $R_{31}$, and $R_{32}$ are each independently a hydrogen group, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group; and

* is a binding site.

5. The compound of claim 1, wherein X in Formula 1 is one of the following compounds represented by Formulas 4a to 4d below:

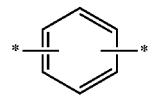

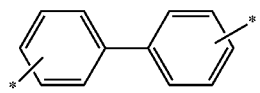

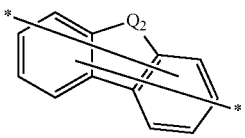

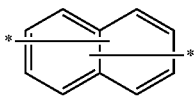

wherein, in Formulas 4a to 4d, $Q_3$ is a linking group represented by —C($R_{30}$)($R_{31}$)— or —S—;

$R_{30}$ and $R_{31}$ are each independently a hydrogen group, a deuterium atom, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, a substituted or unsubstituted $C_6$-$C_{20}$ condensed polycyclic group, a halogen atom, a cyano group, a nitro group, a hydroxyl group, or a carboxyl group; and

* is a binding site.

6. A compound represented by one of the following structures

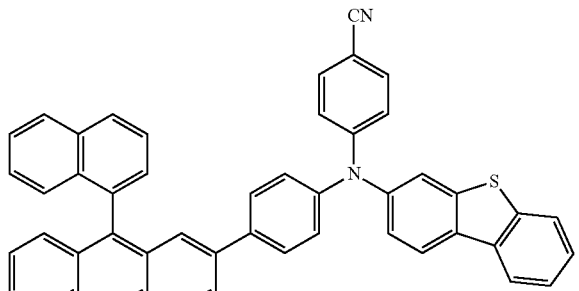

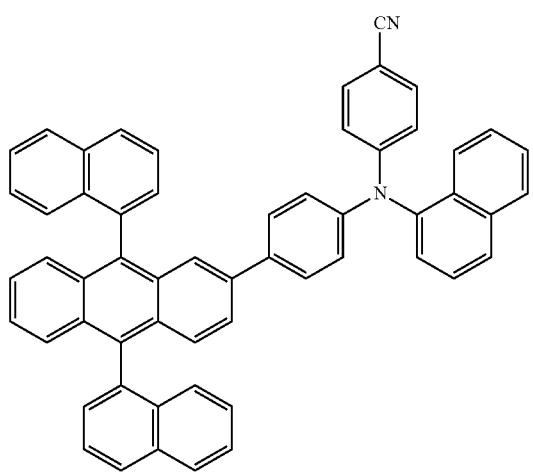

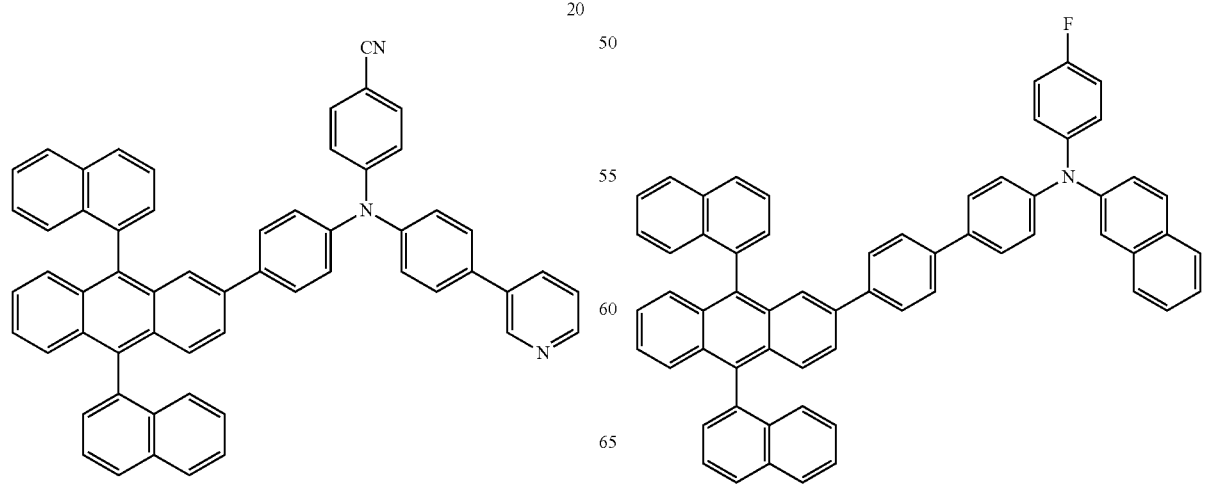

135
-continued
50
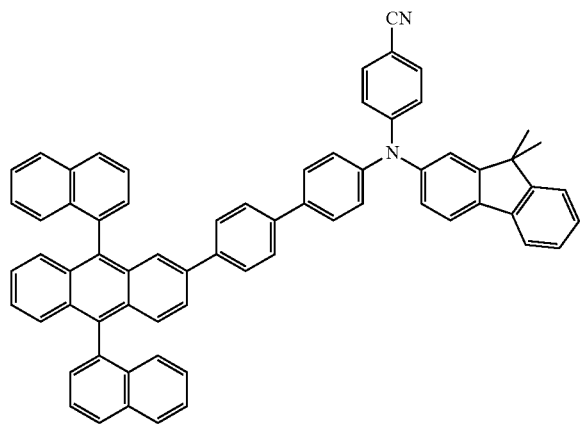
60
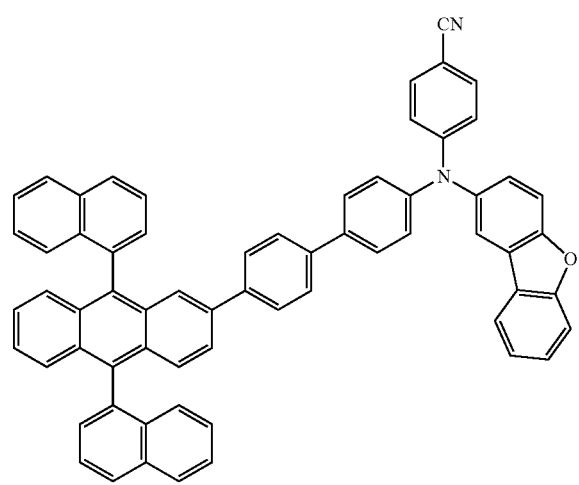
65
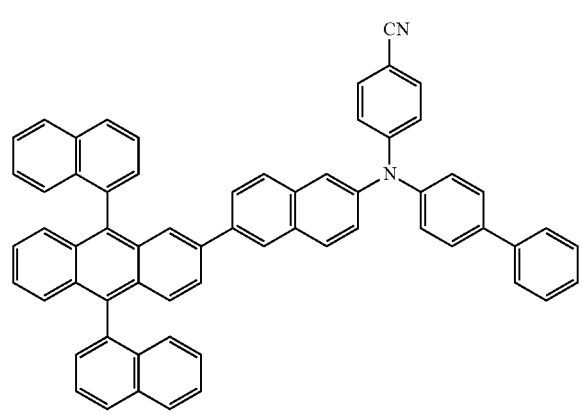
136
-continued
72
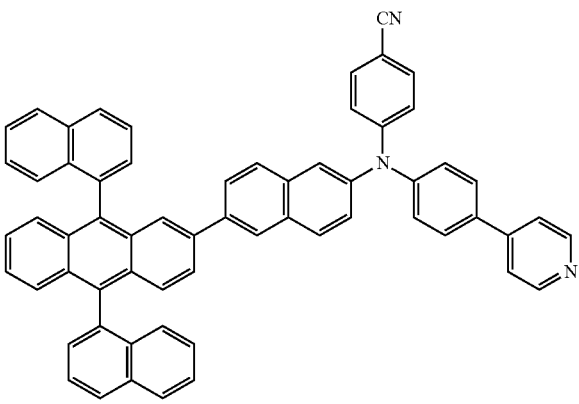
81
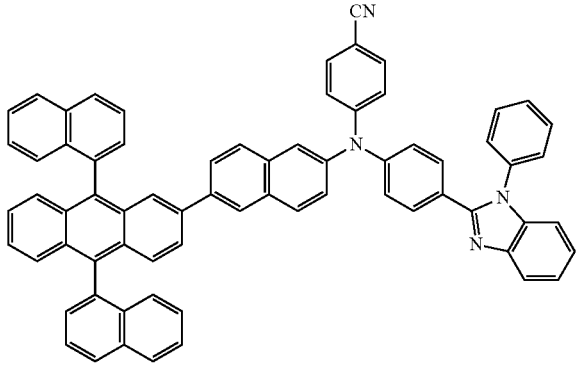
103
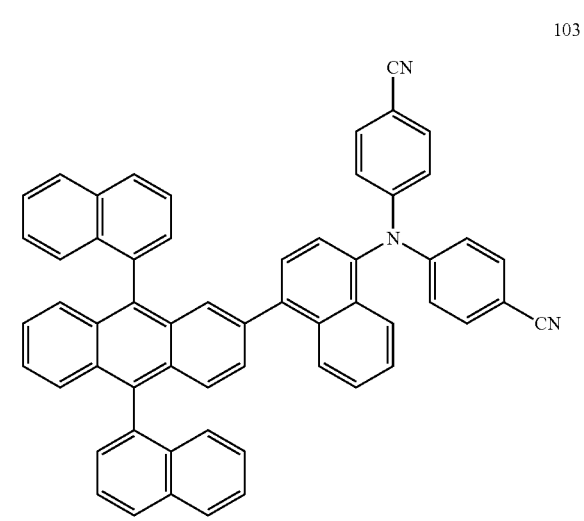

114
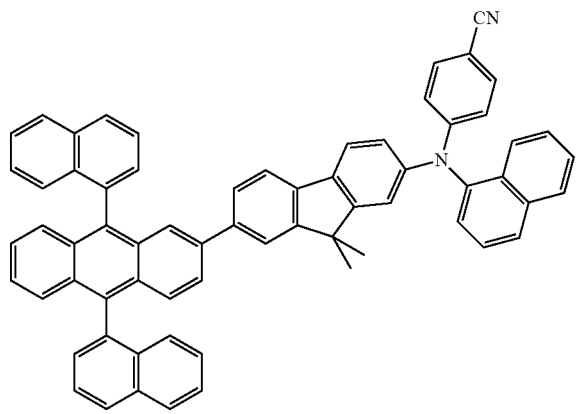
125
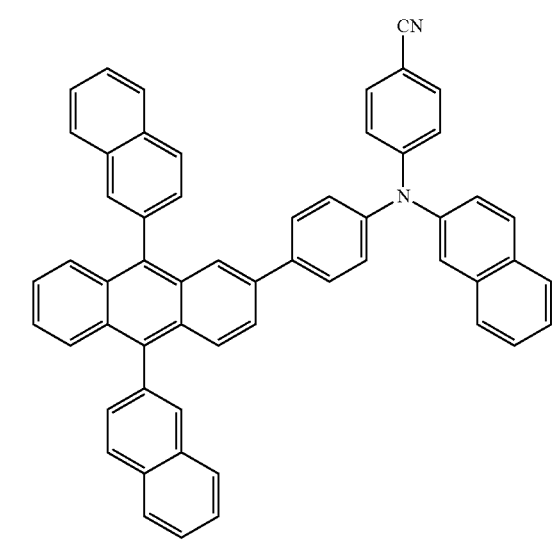
132
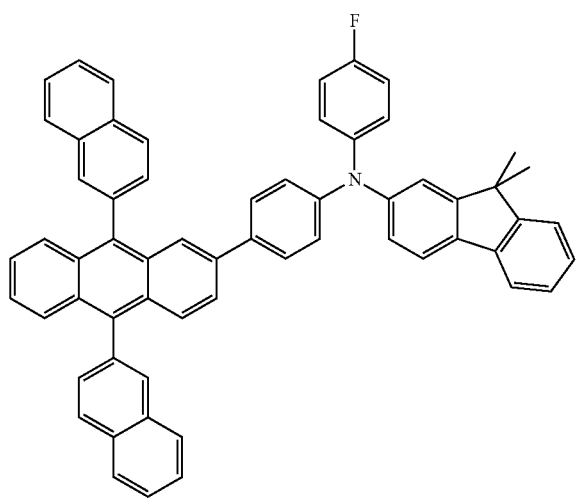
140
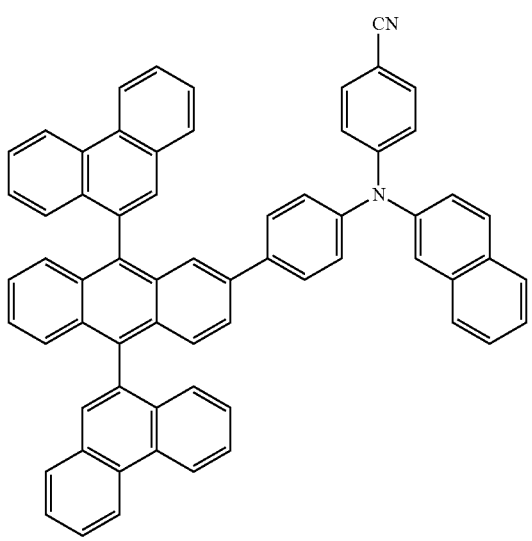
149
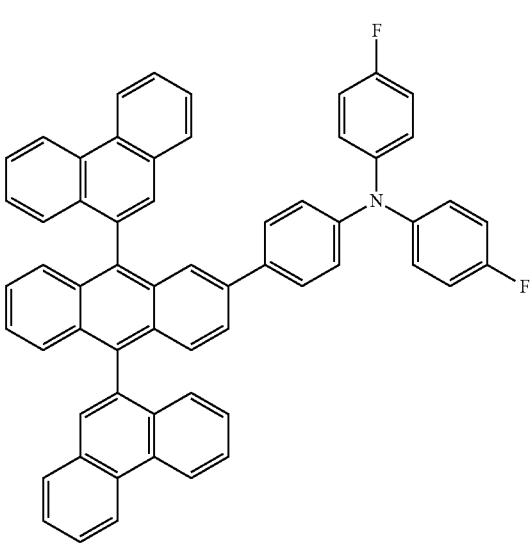
159
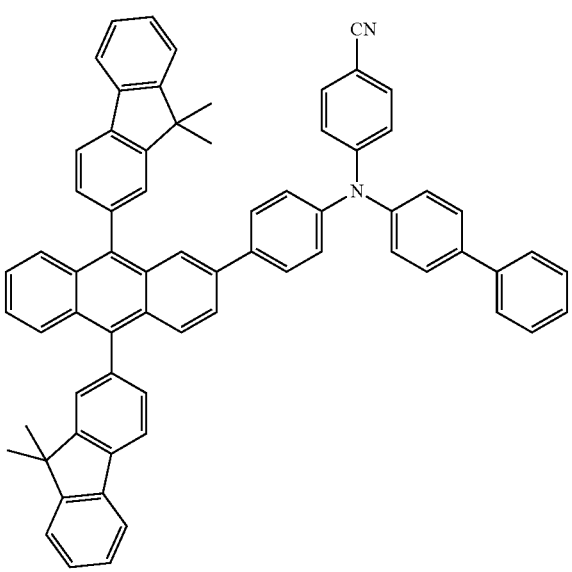

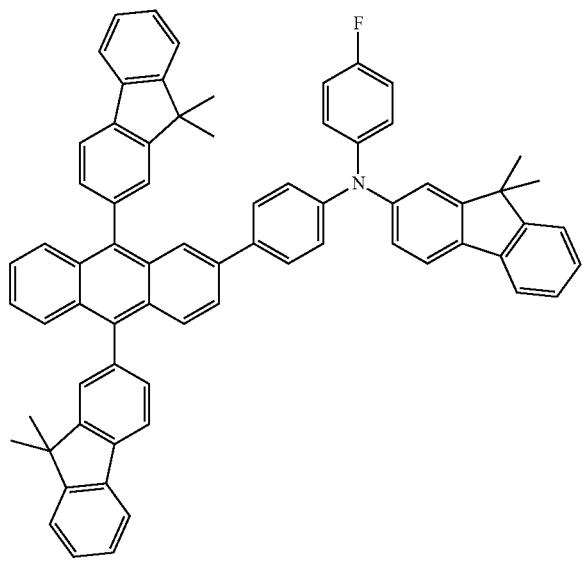

162

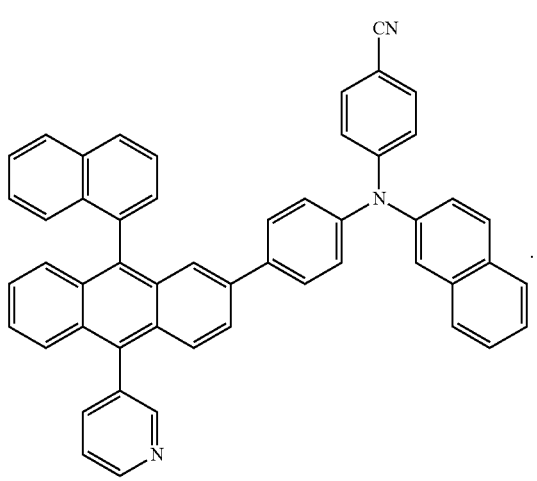

170

7. An organic light-emitting diode (OLED) comprising:
a first electrode;
a second electrode; and
an organic layer that is disposed between the first electrode and the second electrode, and includes the compound of claim 1.

8. The OLED of claim 7, wherein the organic layer is an emission layer, and the compound is used as a fluorescent host, a phosphorescent host, or a fluorescent dopant.

9. The OLED of claim 7, wherein the organic layer includes an electron injection layer, an electron transport layer, or a functional layer having both electron injection and electron transport capabilities.

10. The OLED of claim 7, wherein the organic layer is a blue emission layer.

11. The OLED of claim 7, wherein the organic layer is a blue layer, and the compound of Formula 1 is used as a blue fluorescent host or a dopant.

12. The OLED of claim 7 comprising an emission layer, an electron injection layer, an electron transport layer, a functional layer having both electron injection and electron transport capabilities, a hole injection layer, a hole transport layer, or a functional layer having both hole injection and hole transport capabilities,
wherein the emission layer, the electron injection layer, the electron transport layer, or the functional layer having both electron injection and electron transport capabilities comprises the compound of claim 1, and
the emission layer further comprises an anthracene-based compound, an arylamine-based compound, or a styryl-based compound.

13. The OLED of claim 7 comprising an emission layer, an electron injection layer, an electron transport layer, a functional layer having both electron injection and electron transport capabilities, a hole injection layer, a hole transport layer, or a functional layer having both hole injection and hole transport capabilities,
wherein the electron injection layer, the electron transport layer, or the functional layer having both electron injection and electron transport capabilities comprises a compound represented by Formula 1,
wherein at least one of a red emission layer, a green emission layer, a blue emission layer, and a white emission layer of the emission layer comprises a phosphorescent compound.

14. The OLED of claim 13, wherein the hole injection layer, the hole transport layer, or the functional layer having both hole injection and hole transport capabilities comprises a charge-generating material.

15. The OLED of claim 14, wherein the charge-generating material is a p-dopant.

16. The OLED of claim 15, wherein the p-dopant is a quinone derivative, a metal oxide, or a cyano group-containing compound.

17. The OLED of claim 7, wherein the organic layer comprises an electron transport layer, and the electron transport layer further comprises a metal complex.

18. The OLED of claim 17, wherein the metal complex is a lithium (Li) complex.

19. The OLED of claim 7, wherein the organic layer is comprises the compound of claim 1 by using a wet process.

20. A flat panel display device comprising the OLED of claim 7,
wherein the first electrode of the OLED is electrically connected to a source electrode or a drain electrode in a thin film transistor (TFT).

* * * * *